(12) United States Patent
Jayasinghe et al.

(10) Patent No.: US 12,679,872 B2
(45) Date of Patent: Jul. 14, 2026

(54) TRANSMEMBRANE PORE CONSISTING OF TWO CSGG PORES

(71) Applicants:Oxford Nanopore Technologies PLC, Oxford (GB); VIB VZW, Ghent (BE); Vrije Universiteit Brussel, Brussels (BE)

(72) Inventors: Lakmal Nishantha Jayasinghe, Oxford (GB); Elizabeth Jayne Wallace, Oxford (GB); Pratik Raj Singh, Oxford (GB); Richard George Hambley, Oxford (GB); Michael Robert Jordan, Oxford (GB); Han Remaut, Roosbeek (BE)

(73) Assignees: Oxford Nanopore Technologies PLC, Oxford (GB); VIB VZW, Ghent (BE); Vrije Universiteit Brussel, Brussels (BE)

( * ) Notice: Subject to any disclaimer, the term of this patent is extended or adjusted under 35 U.S.C. 154(b) by 0 days.

(21) Appl. No.: 18/668,987

(22) Filed: May 20, 2024

(65) Prior Publication Data

US 2025/0042952 A1    Feb. 6, 2025

Related U.S. Application Data

(63) Continuation of application No. 16/610,895, filed as application No. PCT/GB2018/051191 on May 3, 2018, now Pat. No. 12,024,541.

(30) Foreign Application Priority Data

May 4, 2017    (GB) ..................................... 1707122

(51) Int. Cl.
*C12Q 1/68* (2018.01)
*C07K 14/245* (2006.01)
(Continued)

(52) U.S. Cl.
CPC .......... *C07K 14/245* (2013.01); *C12Q 1/6869* (2013.01); *G01N 27/44791* (2013.01); *G01N 33/48721* (2013.01)

(58) Field of Classification Search
None
See application file for complete search history.

(56) References Cited

U.S. PATENT DOCUMENTS

| 5,795,782 A | 8/1998 | Church et al. |
| 6,015,714 A | 1/2000 | Baldarelli et al. |

(Continued)

FOREIGN PATENT DOCUMENTS

| CA | 2381139 A1 | 3/2001 |
| CN | 102116783 A | 7/2011 |

(Continued)

OTHER PUBLICATIONS

Pud et al. (2016), Mechanical Trapping of DNA in a Double-Nanopore System, American Chemical Society, 16, 8021-8028.*

(Continued)

*Primary Examiner* — Jehanne S Sitton
(74) *Attorney, Agent, or Firm* — Wolf, Greenfield & Sacks, P.C.

(57) ABSTRACT

Provided is a method of characterising a polynucleotide using a transmembrane pore, wherein the pore is a double pore comprising a first Csg G pore, or a homologue thereof, and a second CsgG pore, or a homologue thereof.

15 Claims, 17 Drawing Sheets

Specification includes a Sequence Listing.

Two reader-heads membrane

(51) Int. Cl.
　　　*C12Q 1/6869* 　　(2018.01)
　　　*G01N 27/447* 　　(2006.01)
　　　*G01N 33/487* 　　(2006.01)

(56) 　　　　　References Cited

U.S. PATENT DOCUMENTS

| | | | |
|---|---|---|---|
| 6,114,121 | A | 9/2000 | Fujiwara et al. |
| 6,150,112 | A | 11/2000 | Weissman et al. |
| 6,362,002 | B1 | 3/2002 | Denison et al. |
| 6,426,231 | B1 | 7/2002 | Bayley et al. |
| 6,627,067 | B1 | 9/2003 | Branton et al. |
| 6,824,659 | B2 | 11/2004 | Bayley et al. |
| 6,863,833 | B1 | 3/2005 | Bloom et al. |
| 6,916,665 | B2 | 7/2005 | Bayley et al. |
| 6,927,070 | B1 | 8/2005 | Bayley et al. |
| 7,189,503 | B2 | 3/2007 | Akeson et al. |
| 8,105,846 | B2 | 1/2012 | Bayley et al. |
| 8,785,211 | B2 | 7/2014 | Bayley et al. |
| 8,822,160 | B2 | 9/2014 | Bayley et al. |
| 8,828,208 | B2 | 9/2014 | Canas et al. |
| 9,073,990 | B2 | 7/2015 | Paas et al. |
| 9,127,313 | B2 | 9/2015 | Brown et al. |
| 9,222,082 | B2 | 12/2015 | Jayasinghe et al. |
| 9,447,152 | B2 | 9/2016 | Clarke et al. |
| 9,562,887 | B2 | 2/2017 | Maglia et al. |
| 9,580,480 | B2 | 2/2017 | Lu et al. |
| 9,588,079 | B2 | 3/2017 | Gundlach et al. |
| 9,732,381 | B2 | 8/2017 | Stoddart et al. |
| 9,751,915 | B2 | 9/2017 | Clarke et al. |
| 9,777,049 | B2 | 10/2017 | Bruce et al. |
| 10,006,905 | B2 | 6/2018 | Maglia et al. |
| 10,167,503 | B2 | 1/2019 | Clarke et al. |
| 10,266,885 | B2 | 4/2019 | Jayasinghe et al. |
| 10,385,389 | B2 | 8/2019 | Heron et al. |
| 10,400,014 | B2 | 9/2019 | Howorka et al. |
| 10,443,097 | B2 | 10/2019 | Jayasinghe et al. |
| 10,472,673 | B2 | 11/2019 | Maglia et al. |
| 10,480,026 | B2 | 11/2019 | Garalde et al. |
| 10,514,378 | B2 | 12/2019 | Maglia et al. |
| 10,669,581 | B2 | 6/2020 | Stoddart et al. |
| 10,802,015 | B2 | 10/2020 | Maglia et al. |
| 10,844,432 | B2 | 11/2020 | Jayasinghe et al. |
| 10,882,889 | B2 | 1/2021 | Bruce et al. |
| 10,975,428 | B2 | 4/2021 | Jayasinghe et al. |
| 10,976,300 | B2 | 4/2021 | Maglia et al. |
| 10,976,311 | B2 | 4/2021 | Maglia et al. |
| 10,995,372 | B2 | 5/2021 | Jayasinghe et al. |
| 11,021,747 | B2 | 6/2021 | Garalde et al. |
| 11,034,734 | B2 | 6/2021 | Howorka et al. |
| 11,104,709 | B2 | 8/2021 | Maglia et al. |
| 11,169,138 | B2 | 11/2021 | Maglia et al. |
| 11,186,868 | B2 | 11/2021 | Jayasinghe et al. |
| 11,307,192 | B2 | 4/2022 | Jayasinghe et al. |
| 11,572,387 | B2 | 2/2023 | Remaut et al. |
| 11,597,970 | B2 | 3/2023 | Jayasinghe et al. |
| 11,685,949 | B2 | 6/2023 | Jayasinghe et al. |
| 11,725,235 | B2 | 8/2023 | Heron et al. |
| 11,739,377 | B2 | 8/2023 | Jayasinghe et al. |
| 11,761,956 | B2 | 9/2023 | Maglia et al. |
| 11,845,780 | B2 | 12/2023 | Bruce et al. |
| 11,939,359 | B2 | 3/2024 | Jayasinghe et al. |
| 11,945,840 | B2 | 4/2024 | Remaut et al. |
| 12,018,326 | B2 | 6/2024 | Jayasinghe et al. |
| 12,024,541 | B2 | 7/2024 | Remaut et al. |
| 12,084,477 | B2 | 9/2024 | Remaut et al. |
| 12,129,518 | B2 | 10/2024 | Garalde et al. |
| 12,173,364 | B2 | 12/2024 | Stoddart et al. |
| 12,227,800 | B2 | 2/2025 | Jayasinghe et al. |
| 12,258,375 | B2 | 3/2025 | Bruce et al. |
| 12,275,761 | B2 | 4/2025 | Howorka et al. |
| 2001/0044137 | A1 | 11/2001 | Heyman et al. |
| 2002/0028458 | A1 | 3/2002 | Lexow |
| 2002/0094526 | A1 | 7/2002 | Bayley et al. |
| 2002/0197614 | A1 | 12/2002 | Mosaic |
| 2003/0044816 | A1 | 3/2003 | Denison et al. |
| 2003/0099951 | A1 | 5/2003 | Akeson et al. |
| 2003/0165936 | A1 | 9/2003 | Rabbani et al. |
| 2003/0211502 | A1 | 11/2003 | Sauer et al. |
| 2003/0215881 | A1 | 11/2003 | Bayley et al. |
| 2004/0209299 | A1 | 10/2004 | Pinter et al. |
| 2004/0214177 | A1 | 10/2004 | Bension |
| 2005/0053961 | A1 | 3/2005 | Akeson et al. |
| 2006/0063171 | A1 | 3/2006 | Akeson et al. |
| 2006/0105461 | A1 | 5/2006 | Tom-Moy et al. |
| 2007/0218471 | A1 | 9/2007 | Kim et al. |
| 2008/0121534 | A1 | 5/2008 | White et al. |
| 2008/0311582 | A1 | 12/2008 | Bayley et al. |
| 2009/0111115 | A1 | 4/2009 | Drmanac et al. |
| 2009/0256116 | A1 | 10/2009 | Shumaker-Parry et al. |
| 2009/0283412 | A1 | 11/2009 | Sansinena et al. |
| 2009/0298075 | A1 | 12/2009 | Travers et al. |
| 2009/0298188 | A1 | 12/2009 | Peti-Peterdi |
| 2010/0075328 | A1 | 3/2010 | Bjornson et al. |
| 2010/0120098 | A1 | 5/2010 | Grunenwald et al. |
| 2010/0196203 | A1 | 8/2010 | Sanghera et al. |
| 2010/0297638 | A1 | 11/2010 | Bayley et al. |
| 2011/0120871 | A1 | 5/2011 | Reid et al. |
| 2011/0121840 | A1 | 5/2011 | Sanghera et al. |
| 2011/0177498 | A1 | 7/2011 | Clarke et al. |
| 2011/0229877 | A1 | 9/2011 | Jayasinghe et al. |
| 2011/0311965 | A1 | 12/2011 | Maglia et al. |
| 2012/0058468 | A1 | 3/2012 | Mckeown |
| 2012/0064599 | A1 | 3/2012 | Jayasinghe et al. |
| 2012/0100530 | A1 | 4/2012 | Moysey et al. |
| 2012/0107802 | A1 | 5/2012 | Stoddart et al. |
| 2012/0322679 | A1 | 12/2012 | Brown et al. |
| 2014/0051069 | A1 | 2/2014 | Jayasinghe et al. |
| 2014/0186823 | A1 | 7/2014 | Clarke et al. |
| 2014/0194324 | A1 | 7/2014 | Gormley et al. |
| 2014/0262784 | A1 | 9/2014 | Clarke et al. |
| 2014/0296083 | A1 | 10/2014 | Brown et al. |
| 2015/0008126 | A1 | 1/2015 | Maglia et al. |
| 2015/0031020 | A1 | 1/2015 | Jayasinghe et al. |
| 2015/0068904 | A1 | 3/2015 | Bruce et al. |
| 2015/0152495 | A1 | 6/2015 | Stava et al. |
| 2015/0175663 | A1 | 6/2015 | Yokoi et al. |
| 2015/0177237 | A1 | 6/2015 | Turner et al. |
| 2015/0191709 | A1 | 7/2015 | Heron et al. |
| 2015/0218629 | A1 | 8/2015 | Heron et al. |
| 2015/0346149 | A1 | 12/2015 | Brown et al. |
| 2016/0010147 | A1 | 1/2016 | Heron et al. |
| 2016/0053300 | A1 | 2/2016 | Maglia et al. |
| 2016/0370358 | A1 | 12/2016 | Maglia et al. |
| 2017/0058337 | A1 | 3/2017 | Clarke et al. |
| 2017/0058338 | A1 | 3/2017 | Jayasinghe et al. |
| 2017/0107569 | A1 | 4/2017 | Heron et al. |
| 2017/0233803 | A1 | 8/2017 | Stoddart et al. |
| 2017/0283470 | A1 | 10/2017 | Howorka et al. |
| 2017/0306398 | A1 | 10/2017 | Jayasinghe et al. |
| 2018/0030526 | A1 | 2/2018 | Brown et al. |
| 2018/0095066 | A1 | 4/2018 | Jayasinghe et al. |
| 2018/0148481 | A2 | 5/2018 | Howorka et al. |
| 2018/0208632 | A1 | 7/2018 | Bruce et al. |
| 2018/0209952 | A1 | 7/2018 | Maglia et al. |
| 2018/0334707 | A1 | 11/2018 | Stoddart et al. |
| 2018/0335425 | A1 | 11/2018 | Maglia et al. |
| 2018/0364214 | A1 | 12/2018 | Maglia et al. |
| 2019/0071721 | A1 | 3/2019 | Jayasinghe et al. |
| 2019/0202876 | A1 | 7/2019 | Jayasinghe et al. |
| 2019/0300582 | A1 | 10/2019 | Jayasinghe et al. |
| 2019/0330282 | A1 | 10/2019 | Jayasinghe et al. |
| 2019/0346431 | A1 | 11/2019 | Maglia et al. |
| 2020/0017556 | A1 | 1/2020 | Howorka et al. |
| 2020/0072824 | A1 | 3/2020 | Maglia et al. |
| 2020/0087724 | A1 | 3/2020 | Heron et al. |
| 2020/0224262 | A1 | 7/2020 | Jayasinghe et al. |
| 2020/0299336 | A9 | 9/2020 | Jayasinghe et al. |
| 2020/0299337 | A9 | 9/2020 | Jayasinghe et al. |
| 2020/0407785 | A1 | 12/2020 | Stoddart et al. |
| 2021/0139972 | A1 | 5/2021 | Jayasinghe et al. |
| 2021/0147486 | A1 | 5/2021 | Remaut et al. |
| 2021/0147490 | A1 | 5/2021 | Remaut et al. |
| 2021/0269872 | A1 | 9/2021 | Jayasinghe et al. |
| 2021/0284696 | A1 | 9/2021 | Remaut et al. |

(56) References Cited

U.S. PATENT DOCUMENTS

| | | |
|---|---|---|
| 2021/0292376 A1 | 9/2021 | Howorka et al. |
| 2021/0317520 A1 | 10/2021 | Jayasinghe et al. |
| 2021/0324020 A1 | 10/2021 | Bruce et al. |
| 2021/0395811 A1 | 12/2021 | Garalde et al. |
| 2021/0405039 A1 | 12/2021 | Maglia et al. |
| 2022/0024985 A9 | 1/2022 | Remaut et al. |
| 2022/0024994 A9 | 1/2022 | Jayasinghe et al. |
| 2022/0056517 A1 | 2/2022 | Remaut et al. |
| 2022/0064230 A1 | 3/2022 | Jayasinghe et al. |
| 2022/0091096 A1 | 3/2022 | Maglia et al. |
| 2022/0119879 A1 | 4/2022 | Jayasinghe et al. |
| 2022/0154269 A9 | 5/2022 | Jayasinghe et al. |
| 2022/0162264 A9 | 5/2022 | Remaut et al. |
| 2022/0283141 A1 | 9/2022 | Jayasinghe et al. |
| 2023/0079731 A1 | 3/2023 | Remaut et al. |
| 2023/0295715 A1 | 9/2023 | Jayasinghe et al. |
| 2024/0026441 A1 | 1/2024 | Heron et al. |
| 2024/0044881 A1 | 2/2024 | Maglia et al. |
| 2024/0060126 A1 | 2/2024 | Jayasinghe et al. |
| 2024/0117422 A1 | 4/2024 | Jayasinghe et al. |
| 2024/0199711 A1 | 6/2024 | Bruce et al. |
| 2024/0254172 A1 | 8/2024 | Maglia et al. |
| 2024/0345073 A9 | 10/2024 | Maglia et al. |
| 2024/0368683 A1 | 11/2024 | Jayasinghe et al. |
| 2025/0066424 A1 | 2/2025 | Remaut et al. |
| 2025/0283165 A1 | 9/2025 | Jayasinghe et al. |

FOREIGN PATENT DOCUMENTS

| | | | |
|---|---|---|---|
| CN | 102174554 A | 9/2011 | |
| CN | 102216783 A | 10/2011 | |
| CN | 102317310 A | 1/2012 | |
| CN | 103460040 A | 12/2013 | |
| CN | 102245760 A | 5/2014 | |
| CN | 113754743 A | 12/2021 | |
| CN | 113773373 A | 12/2021 | |
| CN | 113896776 A | 1/2022 | |
| CN | 113912683 A | 1/2022 | |
| EP | 2194123 B1 | 8/2012 | |
| EP | 2682460 A1 | 8/2013 | |
| GB | 2453377 A | 4/2009 | |
| GB | 1314695.6 | 8/2013 | |
| JP | H10-146190 A | 6/1998 | |
| JP | 2005-253427 A | 9/2005 | |
| JP | 2015-514128 A | 5/2015 | |
| WO | WO 1999/005167 A1 | 2/1999 | |
| WO | WO 2000/028312 A1 | 5/2000 | |
| WO | WO 2001/042782 A1 | 6/2001 | |
| WO | WO 2001/059453 A2 | 8/2001 | |
| WO | WO 2002/042496 A2 | 5/2002 | |
| WO | WO 2003/095669 A1 | 11/2003 | |
| WO | WO 2004/078097 A2 | 9/2004 | |
| WO | WO 2005/013666 A2 | 2/2005 | |
| WO | WO 2005/076010 A2 | 8/2005 | |
| WO | WO 2006/028508 A2 | 3/2006 | |
| WO | WO 2006/100484 A2 | 9/2006 | |
| WO | WO 2007/057668 A1 | 5/2007 | |
| WO | WO 2007/075987 A2 | 7/2007 | |
| WO | WO 2007/084103 A2 | 7/2007 | |
| WO | WO 2007/119880 A1 | 10/2007 | |
| WO | WO 2007/140618 A1 | 12/2007 | |
| WO | WO 2008/102120 A1 | 8/2008 | |
| WO | WO 2008/102121 A1 | 8/2008 | |
| WO | WO 2008/124107 A1 | 10/2008 | |
| WO | WO 2009/020682 A2 | 2/2009 | |
| WO | WO 2009/024775 A1 | 2/2009 | |
| WO | WO 2009/035647 A1 | 3/2009 | |
| WO | WO 2009/044170 A1 | 4/2009 | |
| WO | WO 2009/077734 A2 | 6/2009 | |
| WO | WO 2009/143425 A1 | 11/2009 | |
| WO | WO 2010/004265 A1 | 1/2010 | |
| WO | WO 2010/004273 A1 | 1/2010 | |
| WO | WO 2010/034018 A2 | 3/2010 | |
| WO | WO 2010/055307 A1 | 5/2010 | |
| WO | WO 2010/086602 A1 | 8/2010 | |
| WO | WO 2010/086603 A1 | 8/2010 | |
| WO | WO 2010/086622 A1 | 8/2010 | |
| WO | WO 2010/122293 A1 | 10/2010 | |
| WO | WO 2010/148126 A1 | 12/2010 | |
| WO | WO 2011/067559 A1 | 6/2011 | |
| WO | WO 2012/005857 A1 | 1/2012 | |
| WO | WO 2012/042226 A1 | 4/2012 | |
| WO | WO 2012/107778 A2 | 8/2012 | |
| WO | WO 2012/164270 A1 | 12/2012 | |
| WO | WO 2013/014451 A1 | 1/2013 | |
| WO | WO 2013/041878 A1 | 3/2013 | |
| WO | WO 2013/057495 A1 | 4/2013 | |
| WO | WO 2013/098561 A1 | 7/2013 | |
| WO | WO 2013/098562 A1 | 7/2013 | |
| WO | WO 2013/109970 A1 | 7/2013 | |
| WO | WO 2013/121224 A1 | 8/2013 | |
| WO | WO 2013/123379 A2 | 8/2013 | |
| WO | WO 2013/153359 A1 | 10/2013 | |
| WO | WO 2014/078489 A1 | 10/2013 | |
| WO | WO 2014/006442 A1 | 1/2014 | |
| WO | WO 2014/013259 A1 | 1/2014 | |
| WO | WO 2014/013260 A1 | 1/2014 | |
| WO | WO 2014/013262 A1 | 1/2014 | |
| WO | WO 2014/064443 A1 | 5/2014 | |
| WO | WO 2014/064444 A1 | 5/2014 | |
| WO | WO 2014/122654 A2 | 8/2014 | |
| WO | WO 2014/135838 A1 | 9/2014 | |
| WO | WO 2014/142850 A1 | 9/2014 | |
| WO | WO 2014/153047 A1 | 9/2014 | |
| WO | WO 2014/153625 A1 | 10/2014 | |
| WO | WO 2014/187924 A1 | 11/2014 | |
| WO | WO 2015/022544 A1 | 2/2015 | |
| WO | WO 2015/051378 A1 | 4/2015 | |
| WO | WO 2015/055981 A1 | 4/2015 | |
| WO | WO 2015/097289 A1 | 7/2015 | |
| WO | WO 2015/110777 A1 | 7/2015 | |
| WO | WO 2015/124935 A1 | 8/2015 | |
| WO | WO 2015/140535 A1 | 9/2015 | |
| WO | WO 2015/150786 A1 | 10/2015 | |
| WO | WO 2015/150787 A1 | 10/2015 | |
| WO | WO 2015/166275 A1 | 11/2015 | |
| WO | WO 2015/166276 A1 | 11/2015 | |
| WO | WO 2016/034591 A2 | 3/2016 | |
| WO | WO 2016/055777 A2 | 4/2016 | |
| WO | WO 2016/055778 A1 | 4/2016 | |
| WO | WO 2016/132123 A1 | 8/2016 | |
| WO | WO 2016/164422 A2 | 10/2016 | |
| WO | WO 2016/166232 A1 | 10/2016 | |
| WO | WO 2017/149316 A1 | 9/2017 | |
| WO | WO 2017/149317 A1 | 9/2017 | |
| WO | WO 2017/149318 A1 | 9/2017 | |
| WO | WO 2017/174990 A1 | 10/2017 | |
| WO | WO 2017/203267 A1 | 11/2017 | |
| WO | WO 2018/100370 A1 | 6/2018 | |
| WO | WO 2018/146491 A1 | 8/2018 | |
| WO | WO 2018/203084 A1 | 11/2018 | |
| WO | WO 2018/211241 A1 | 11/2018 | |
| WO | WO 2019/002893 A1 | 1/2019 | |
| WO | WO 2020/095052 A1 | 5/2020 | |
| WO | WO 2020/183172 A1 | 9/2020 | |
| WO | WO 2020/208357 A1 | 10/2020 | |
| WO | WO 2021/101378 A1 | 5/2021 | |
| WO | WO 2022/213253 A1 | 10/2022 | |
| WO | WO 2023/026056 A1 | 3/2023 | |
| WO | WO 2023/057432 A1 | 4/2023 | |
| WO | WO 2023/118404 A1 | 6/2023 | |
| WO | WO 2023/198911 A2 | 10/2023 | |
| WO | WO 2024/033421 A2 | 2/2024 | |
| WO | WO 2024/033422 A1 | 2/2024 | |
| WO | WO 2024/033443 A1 | 2/2024 | |
| WO | WO 2024/033447 A1 | 2/2024 | |
| WO | WO 2024/089270 A2 | 5/2024 | |

OTHER PUBLICATIONS

U.S. Appl. No. 18/665,109, filed May 15, 2024, Jayasinghe et al.
U.S. Appl. No. 18/797,277, filed Aug. 7, 2024, Remaut et al.

(56) References Cited

OTHER PUBLICATIONS

Extended European Search Report for Application No. EP21163695. 6, mailed Sep. 14, 2021.

International Search Report and Written Opinion for Application No. PCT/GB2018/051191, mailed Jul. 2, 2018.

International Preliminary Report on Patentability for Application No. PCT/GB2018/051191, mailed Nov. 14, 2019.

[No Author Listed] EBI Accession No. GSP:AXX09397. May 13, 2010.

[No Author Listed] EBI Accession No. A0A085GH19. Oct. 29, 2014.

[No Author Listed] EBI Accession No. A0A0DILDB9. Apr. 29, 2015.

[No Author Listed] EBI Accession No. EMBLCDS:ABV05494. Sep. 11, 2007.

[No Author Listed] Enterobacteria phage vB_EcoM-ACG-C40, complete genome. Genbank Acc. No. NC 019399.1. 2 pages. [97 pages in 70046US02].

[No Author Listed] Helicos BioSciences Corporation, "Helicos Genetic Analysis System," Specification Sheet retrieved online at: www.helicosbio.com/Portals/O/Documents/Helicos_SalesSpec. pdf, 4 pages (2008).

[No Author Listed] NCBI Genbank Accession No. ABV05494. Jan. 31, 2014, 1 page.

[No Author Listed] NexteraTM DNA Sample Preparation Kits (Illumina) Oct. 2011. (2 pages).

[No Author Listed] Oxford Nanopore "Product" brochure (2020) https://nanoporetech.com/sites/default/files/s3/literature/product-brochure.Pdf (36 pages).

[No Author Listed] Protein Databank entries of AlphaFold structure prediction for POAE98 and POA202, 2 pages.

[No Author Listed] Uniprot Accession No. A0A081NL13. Oct. 29, 2014. 4 pages.

[No Author Listed] Uniprot Accession No. A0A0P7DN88. Jan. 20, 2016. 3 pages.

[No Author Listed] Uniprot Accession No. POAE98 and POA202 search results, last accessed Mar. 29, 2022. 4 pages.

[No Author Listed] Uniprot Accession No. Q8Z727. Oct. 24, 2003. 4 pages.

[No Author Listed] UniProt, "SubName: Full=Curli production assembly/transport component {ECO:0000313:EMBL:CTR43957. 1};", XP002783536, retrieved from EBI accession No. UNIPROT:A0A0K3UZP3, Nov. 11, 2015.

[No Author Listed] UniprotKB Accession No. N2DXI0, Jun. 26, 2013, 1 page.

[No Author Listed], *Escherichia coli* HS curli production assembly/transport subunit. Accession No. ABV05494. Sep. 1, 20071. 2 pages.

Afonine et al., Real-space refinement in PHENIX for cryo-EM and crystallography. Acta Crystallogr D Struct Biol. 2018;74(Pt 6):531-544. doi:10.1107/S2059798318006551.

Ahern, Biochemical, reagents kits offer scientists good return on investment. The Scientist. Jul. 25, 1995;9(15):20.

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al. Basic local alignment search tool. J Mol Biol. Oct. 5, 1990;215(3):403-10. doi: 10.1016/S0022-2836(05)80360-2.

Altschul, A protein alignment scoring system sensitive at all evolutionary distances. J Mol Evol. Mar. 1993;36(3):290-300. doi: 10.1007/BF00160485.

Aoki et al., Single channel properties of lysenin measured in artificial lipid bilayers and their applications to biomolecule detection. Proc Jpn Acad Ser B Phys Biol Sci. 2010;86(9):920-5.

Aravind et al., The DNA-Repair Protein AlkB, EGL-9, and Leprecan Define New Families of 2-oxoglutarate-andIron-Dependent Dioxygenases. Genome Biology. 2001;2:1-8.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Ashton et al., MinION Nanopore Sequencing Identifies the Position and Structure of a Bacterial antibiotic Resistance Island. Nat Biotechnol. Mar. 2015;33(3):296-302.

Astier et al., Stochastic detection of motor protein-RNA complexes by single-channel current recording. Chemphyschem. Oct. 27, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Atkins et al., Structure-function relationships of a novel bacterial toxin, hemolysin E. The role of alpha G. J Biol Chem. Dec. 29, 2000;275(52):41150-5.

Avrameas, Coupling of enzymes to proteins with glutaraldehyde. Use of the conjugates for the detection of antigens and antibodies. Immunochemistry. Jan. 1969;6(1):43-52.

Ayub et al., Engineered transmembrane pores. Curr Opin Chem Biol. 2016;34:117-126. doi:10.1016/j.cbpa.2016.08.005. Author Manuscript, 16 pages.

Bayley et al., Stochastic sensors inspired by biology. Nature. Sep. 13, 2001;413(6852):226-30.

Bayley et al., Wrestling with native chemical ligation. ACS Chem Biol. Dec. 18, 2009;4(12):983-5. doi: 10.1021/cb900304p.

Bayley, Membrane-protein structure: Piercing insights. Nature. Jun. 4, 2009;459(7247):651-2. doi: 10.1038/459651a.

Bayley, Nanopore Sequencing: From Imagination to Reality. Clin Chem. 2015;61(1):25-31.

Bayley, Sequencing single molecules of DNA. Curr Opin Chem Biol. Dec. 2006;10(6):628-37. Epub Nov. 20, 2006.

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Bezrukov et al., Counting Polymers Moving Through a Single Ion Channel. Nature. Jul. 28, 1994;370:279-81.

Bianco et al., Helicase unwinding: active or merely perfect? J Mol Biol. Jul. 13, 2012;420(3):139-40. doi: 10.1016/j.jmb.2012.04.030. Epub May 2, 2012.

Bleijlevens et al., Changes in Protein Dynamics of the DNA Repair Dioxygenase AlkB Upon Binding of FE2+ and 2-Oxoglutarate. Biochemistry. Mar. 26, 2012;51:3334-41.

Bleijlevens et al., Dynamic States of the DNA Repair Enzyme AlkB regulate Product Release. Eur Mol Biol Org. Jul. 11, 2008;9(9):872-77.

Boersma et al., Continuous stochastic detection of amino acid enantiomers with a protein nanopore. Angew Chem Int Ed Engl. Sep. 17, 2012;51(38):9606-9. doi: 10.1002/anie.201205687. Epub Aug. 29, 2012.

Bourdon et al., Molecular cloning and sequence analysis of a chondroitin sulfate proteoglycan cDNA. Proc Natl Acad Sci U S A. Mar. 1985;82(5):1321-5.

Braha et al., Carriers versus adapters in stochastic sensing. Chemphyschem. May 2005;6(5):889-92.

Braha et al., Designed protein pores as components for biosensors. Chem Biol. Jul. 1997;4(7):497-505.

Branton et al., The potential and challenges of nanopore sequencing. Nat Biotechnol. Oct. 2008;26(10):1146-53. doi:10.1038/nbt.1495.

Braslavsky et al., Sequence information can be obtained from single DNA molecules. Proc Natl Acad Sci U S A. Apr. 1, 2003;100(7):3960-4. Epub Mar. 21, 2003.

Brown et al., Tools for macromolecular model building and refinement into electron cryo-microscopy reconstructions. Acta Crystallogr D Biol Crystallogr. 2015;71(Pt 1):136-153. doi:10.1107/S1399004714021683.

(56)          References Cited

OTHER PUBLICATIONS

Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.

Butler et al., Determination of RNA orientation during translocation through a biological nanopore. Biophys J. Jan. 1, 2006;90(1): 190-9. Epub Oct. 7, 2005.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Byrd et al., Dda helicase tightly couples translocation on single-stranded DNA to unwinding of duplex DNA: Dda is an optimally active helicase. J Mol Biol. Jul. 13, 2012;420(3):141-54. doi: 10.1016/j.jmb.2012.04.007. Epub Apr. 11, 2012.

Cao et al., Mapping the sensing spots of aerolysin for single oligonucleotides analysis. Nat Commun. Jul. 19, 2018;9(1):2823. doi: 10.1038/s41467-018-05108-5. 9 pages.

Cao et al., Structure of the nonameric bacterial amyloid secretion channel. Proc Natl Acad Sci USA. Dec. 16, 2014;111(50):E5439-44. doi: 10.1073/pnas.1411942111. Epub Dec. 1, 2014.

Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.

Chan, Advances in sequencing technology. Mutat Res. Jun. 3, 2005;573(1-2):13-40.

Chapman et al., Role of *Escherichia coli* curli operons in directing amyloid fiber formation. Science. 2002;295(5556):851-855. doi:10. 1126/science.1067484. Author Manuscript, 9 pages.

Cheley et al., A functional protein pore with a "retro" transmembrane domain. Protein Sci. Jun. 1999;8(6):1257-67.

Cheley et al., A genetically encoded pore for the stochastic detection of a protein kinase. Chembiochem. Dec. 2006;7(12):1923-7.

Cheley et al., Spontaneous oligomerization of a staphylococcal alpha-hemolysin conformationally constrained by removal of residues that form the transmembrane beta-barrel. Protein Eng. Dec. 1997;10(12):1433-43.

Chen et al., Atomic Layer Deposition to Fine-Tune the Surface Properties and Diameters of Fabricated Nanopores. Nano Lett. Jun. 2, 20045;4(7):1333-1337.

Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.

Cheng et al., Design and testing of aptamer-based electrochemical biosensors for proteins and small molecules. Bioelectrochemistry. Nov. 2009;77(1):1-12. doi: 10.1016/j.bioelechem.2009.04.007. Epub May 5, 2009.

Chin et al., Addition of a photocrosslinking amino acid to the genetic code of *Escherichiacoli*. Proc Natl Acad Sci U S A. Aug. 20, 2002;99(17):11020-4. doi: 10.1073/pnas.172226299. Epub Aug. 1, 2002.

Chin et al., The Metabolite alpha-Ketoglutarate Extends Lifespan by Inhibiting ATP Synthase and TOR. Nature. Jul. 19, 2014;510:397-401.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.

Colas et al., Microscopical investigations of nisin-loaded nanoliposomes prepared by Mozafari method and their bacterial targeting. Micron. 2007;38(8):841-7. doi: 10.1016/j.micron.2007.06.013. Epub Jul. 3, 2007.

Comai et al., Protein engineering modulates the transport properties and ion selectivity of the pores formed by staphylococcal gamma-haemolysins in lipid membranes. Mol Microbiol. Jun. 2002;44(5):1251-67.

Dani et al., MspA Porin-Gold Nanoparticle Assemblies: Enhanced Binding through a Controlled Cysteine Mutation. Nano Lett. Apr. 2008;8(4):1229-36. doi: 10.1021/nl072658h. Epub Mar. 5, 2008.

De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.

Deamer et al., Characterization of nucleic acids by nanopore analysis. Acc Chem Res. Oct. 2002;35(10):817-25.

Deamer et al., Nanopores and nucleic acids: prospects for ultrarapid sequencing. Trends Biotechnol. Apr. 2000;18(4):147-51.

Derrington et al., A Novel DNA Sensing Technique Using Nanopore MSPA. 54th Annual Meeting of the Biophysical Society, Poster 2182-Plat, 2 pages (2010).

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Desvaux et al., Secretion and subcellular localizations of bacterial proteins: a semantic awareness issue. Trends Microbiol. Apr. 2009;17(4):139-45. doi: 10.1016/j.tim.2009.01.004. Epub Mar. 18, 2009.

Desvaux et al., The general secretory pathway: a general misnomer? Trends Microbiol. Jul. 2004;12(7):306-9.

Devereux et al., A comprehensive set of sequence analysis programs for the VAX. Nucleic Acids Res. Jan. 11, 1984;12(1 Pt 1):387-95. doi: 10.1093/nar/12.1part1.387.

Devos et al., Practical limits of function prediction. Proteins. Oct. 1, 2000;41(1):98-107.

Dong et al., Oroxylin A inhibits hemolysis via hindering the self-assembly of α-hemolysin heptameric transmembrane pore. PLoS Comput Biol. 2013;9(1):e1002869. doi: 10.1371/journal.pcbi. 1002869. Epub Jan. 17, 2013.

Dorre et al., Techniques for single molecule sequencing. Bioimaging, vol. 5:139-152 (1997).

Eid et al., Real-time DNA sequencing from single polymerase molecules. Science. Jan. 2, 2009;323(5910):133-8. doi:10.1126/science.1162986. Epub Nov. 20, 2008.

Eifier et al., Cytotoxin ClyA from *Escherichia coli* assembles to a 13-meric pore independent of its redox-state. EMBO J. Jun. 7, 2006;25(11):2652-61. doi: 10.1038/sj.emboj.7601130. Epub May 11, 2006.

Eliseev et al., Aminocyclodextrins as Selective Hosts with Several Binding Sites for Nucleotides. Angew. Chem. Int. Ed. Engl., vol. 32(9):1331-1333 (1993).

Eliseev et al., Molecular Recognition of Nucleotides, Nucleosides, and Sugars by Aminocyclodextrins. J. Am. Chem. Soc., vol. 116:6081-6088 (1994).

Engelhardt et al., A tetrameric porin limits the cell wall permeability of Mycobacterium smegmatis. J Biol Chem. Oct. 4, 2002;277(40):37567-72. Epub Jul. 18, 2002.

Epstein, Assembly, Spatial Distribution, and Secretion Activity of the Curlin Secretion Lipoprotein, CsgG. Dissertation. The University of Michigan. 2008. 167 pages.

Ergel et al., Protein Dynamics Control the Progression and Efficiency of the Catalytic Reaction Cycle of the *Escherichia coli* DNA-Repair Enzyme AlkB. J Biol Chem. Oct. 24, 2014;289(43):29584-601.

Fahie et al., Resolved Single-Molecule Detection of Individual Species Within a Mixture of Anti-Biotin Antibodies Using an Engineered Monometric Nanopore. Am Chem Soc. Jan. 9, 2015;9(2):1089-98.

Fiaschi et al., Auto-Assembling Detoxified Staphylococcus aureus Alpha-Hemolysin Mimicking the Wild-Type Cytolytic Toxin. Clin Vaccine Immunol. Jun. 6, 2016;23(6):442-50. doi: 10.1128/CVI. 00091-16.

Fiume et al., Savant: genome browser for high-throughput sequencing data. Bioinformatics. Aug. 15, 2010;26(16):1938-44. doi: 10.1093/bioinformatics/btq332. Epub Jun. 20, 2010.

Fleckenstein et al., "UPI0002CA1AFE" Uniprot Accession Number, https://www.uniprot.org/uniparc/UPI0002CA1AFE, Jun. 26, 2013 (Jun. 26, 2013).

(56)     References Cited

OTHER PUBLICATIONS

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Fologea et al., Potential analytical applications of lysenin channels for detection of multivalent ions. Anal Bioanal Chem. Oct. 2011;401(6):1871-9. doi:10.1007/s00216-011-5277-8. Epub Aug. 5, 2011.

Franceschini et al., A nanopore machine promotes the vectorial transport of DNA across membranes. Sep. 2013; Nat Commun. 2013;4:2415. doi: 10.1038/ncomms3415.

Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano. 6b03159. Epub Aug. 15, 2016.

Freedman et al., Single Molecule Unfolding and Stretching of Protein Domains Inside a Solid-State Nanopore by Electric Field. Scientific Reports. Apr. 10, 2013;3(1638):1-8.

Galenkamp et al., Direct electrical quantification of glucose and asparagine from bodily fluids using nanopores. Nat Commun. 2018;9(1):4085. Published Oct. 5, 2018. doi:10.1038/s41467-018-06534-1.

Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghanem et al., Chimeric mutants of staphylococcal hemolysin, which act as both one-component and two-component hemolysin, created by grafting the stem domain. Febs J. Jun. 2022;289(12):3505-3520. doi: 10.1111/febs.16354. Epub Feb. 16, 2022.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gibson et al., AgfC and AgfE facilitate extracellular thin aggregative fimbriae synthesis in *Salmonella enteritidis*. Microbiology. Apr. 2007;153(Pt 4):1131-1140. doi: 10.1099/mic.0.2006/000935-0.

Gilbert et al., Two Structural Transitions in Membrane Pore Formation by Pneumolysin, the Pore-Forming Toxin of *Streptococcus pneumoniae*. Cell. May 2, 19998;97:647-655.

Goedhart et al., Quantitative co-expression of proteins at the single cell level—application to a multimeric FRET sensor. PLoS One. 2011;6(11):e27321. doi: 10.1371/journal.pone.0027321. Epub Nov. 17, 2011.

González-Pérez et al., Biomimetic triblock copolymer membrane arrays: a stable template for functional membrane proteins. Langmuir. Sep. 15, 2009;25(18):10447-50. doi: 10.1021/la902417m.

Goryshin et al., Tn5 in vitro transposition. J Biol Chem. Mar. 27, 1998;273(13):7367-74. doi: 10.1074/jbc.273.13.7367.

Gouridis et al., Conformational Dynamics in Substrate-Binding Domains Influences Transport in the ABC Importer GinPQ. Nat Stuct Mol Biol. Dec. 8, 2014;22(1):57-66.

Goyal et al., Crystallization and preliminary X-ray crystallographic analysis of the curli transporter CsgG. Acta Crystallographica Section F: Structural Biology and Crystallization Communications. Dec. 1, 2013;69(12):1349-53.

Goyal et al., Structural and mechanistic insights into the bacterial amyloid secretion channel CsgG. Nature. Dec. 11, 2014;516(7530):250-3 with Supplemental Information. doi: 10.1038/nature13768. Epub Sep. 14, 2014.

Gu et al., Capture of a single molecule in a nanocavity. Science. Jan. 26, 2001;291(5504):636-40.

Gu et al., Electroosmotic enhancement of the binding of a neutral molecule to a transmembrane pore. Proc Natl Acad Sci U S A. Dec. 23, 2003;100(26):15498-503. Epub Dec. 15, 2003.

Gu et al., Interaction of the noncovalent molecular adapter, beta-cyclodextrin, with the staphylococcal alpha-hemolysin pore. Biophys J. Oct. 2000;79(4):1967-75.

Gu et al., Prolonged residence time of a noncovalent molecular adapter, beta-cyclodextrin, within the lumen of mutant alpha-hemolysin pores. J Gen Physiol. Nov. 2001;118(5):481-94.

Gu et al., Reversal of charge selectivity in transmembrane protein pores by using noncovalent molecular adapters. Proc Natl Acad Sci U S A. Apr. 11, 2000;97(8):3959-64.

Gu et al., Stochastic sensing of organic analytes by a pore-forming protein containing a molecular adapter. Nature. Apr. 22, 1999;398(6729):686-90.

Guan et al., Stochastic sensing of TNT with a genetically engineered pore. Chembiochem. Oct. 2005;6(10):1875-81.

Guasch et al., Detailed architecture of a DNA translocating machine: the high-resolution structure of the bacteriophage phi29 connector particle. J Mol Biol. Jan. 25, 2002;315(4):663-76.

Guo et al., Nanopore sensor for copper ion detection using a polyamine decorated ß-cyclodextrin as the recognition element. RSC Adv. 2017;7:15315. doi: 10.1039/c7ra00454k. 6 pages.

Hall et al., Hybrid pore formation by directed insertion of α-haemolysin into solid-state nanopores. Nat Nanotechnol. Dec. 2010;5(12):874-7. doi: 10.1038/nnano.2010.237. Epub Nov. 28, 2010.

Hammar et al., Expression of two csg operons is required for production of fibronectin- and congo red-binding curli polymers in *Escherichia coli* K-12. Mol Microbiol. Nov. 1995; 18(4):661-70. doi: 10.1111/j.1365-2958.1995.mmi_18040661.x.

Han et al., Characterization and optimization of an entropic trap for DNA separation. Anal Chem. Jan. 15, 2002;74(2):394-401.

Han et al., RecJ exonuclease: substrates, products and interaction with SSB. Nucleic Acids Res. Feb. 18, 2006;34(4):1084-91. Print 2006.

Haque et al., DNA-associated click chemistry. Science China Chemistry. Feb. 2014;57(2):215-231. doi:10.1007/s11426-013-5035-1.

Haque et al., Solid-State and Biological Nanopore for Real-Time Sensing of Single Chemical and Sequencing of DNA. Nano Today. Feb. 2013;8(1):56-74.

He et al. 2012; The T4 phage SF1 B helicase dda is structurally optimized to perform DNA strand separation. Structure. 20:1189-1200.

Heng et al., Sizing DNA using a nanometer-diameter pore. Biophys J. Oct. 2004;87(4):2905-11. doi: 10.1529/biophysj.104.041814. Epub Aug. 23, 2004.

Henrickson et al., Driven DNA transport into an asymmetric nanometer-scale pore. Phys Rev Lett. Oct. 2, 2000;85(14):3057-60.

Heron et al., Direct detection of membrane channels from gels using water-in-oil droplet bilayers. J Am Chem Soc. Dec. 2, 2007;129(51):16042-7. Epub Dec. 1, 2007.

Higgins et al., DNA-joining enzymes: a review. Methods Enzymol. 1979;68:50-71. doi: 10.1016/0076-6879(79)68006-0.

Ho et al., Engineering a nanopore with co-chaperonin function. Sci Adv. Dec. 11, 2015;1(11):e1500905. doi: 10.1126/sciadv.1500905. 9 pages.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

Howorka et al., DNA Duplex Formation of Individual DNA Strands within a Single Protein Pore. Biophysical Journal, vol. 82{ 1, pt. 2):508a, No. 2482-Plat (2002).

Howorka et al., Kinetics of duplex formation for individual DNA strands within a single protein nanopore. Proc Natl Acad Sci U S A. Nov. 6, 2001;98(23):12996-3001. Epub Oct. 23, 2001.

Howorka et al., Nanopore Analytics: Sensing of Single Molecules. The Royal Society of Chemistry. Jun. 15, 2009;38:2360-84.

Howorka et al., Nanopores as protein sensors. Nat Biotechnol. Jun. 7, 2012;30(6):506-7. doi: 10.1038/nbt.2264.

(56) References Cited

OTHER PUBLICATIONS

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.

Hwang et al., Electrical behavior of droplet interface bilayer networks: experimental analysis and modeling. J Am Chem Soc. Sep. 26, 2007;129(38):11854-64. Epub Sep. 1, 2007.

Iacovache et al., Structure and assembly of pore-forming proteins. Curr Opin Struct Biol. Apr. 2010;20(2):241-6. doi:10.1016/j.sbi.2010.01.013. Epub Feb. 19, 2010.

Ivanov et al., DNA tunneling detector embedded in a nanopore. Nano Lett. Jan. 12, 2011;11(1):279-85. doi: 10.1021/nl103873a. Epub Dec. 6, 2010.

Ivanov et al., DNA tunneling detector embedded in a nanopore. Nano Lett. Jan. 1, 20112;11(1):279-85. doi: 10.1021/nl103873a. Epub Dec. 6, 2010.

Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17 (1):256.

Jayasinghe et al., The leukocidin pore: evidence for an octamer with four LukF subunits and four LukS subunits alternating around a central axis. Protein Sci. Oct. 2005;14(10):2550-61.

Johnston et al., Coexpression of proteins in bacteria using T7-based expression plasmids: expression of heteromeric cell-cycle and transcriptional regulatory complexes. Protein Expr Purif. Dec. 2000;20(3):435-43.

Juncker et al., Prediction of lipoprotein signal peptides in Gram-negative bacteria. Protein Sci. 2003;12(8):1652-1662. doi:10.1110/ps.0303703.

Jung et al., The internal cavity of the staphylococcal alpha-hemolysin pore accommodates approximately 175 exogenous amino acid residues. Biochemistry. Jun. 28, 2005;44(25):8919-29.

Kalli et al., Conformational changes in talin on binding to anionic phospholipid membranes facilitate signaling by integrin transmembrane helices. PLoS Comput Biol. Oct. 2013;9(10):e1003316. doi:10.1371/journal.pcbi.1003316.

Kanaan et al., UPF1-like helicase grip on nucleic acids dictates processivity. Nat Commun. Sep. 14, 2018;9(1):3752. doi: 10.1038/s41467-018-06313-y.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Khulbe et al., DNA translocation through a-hemolysin nanopores with potential application to macromolecular data storage. Journal Applied Physics, vol. 97(104317):1-7 (2005).

Kimanius et al., Accelerated cryo-EM structure determination with parallelisation using GPUs in RELION-2. Elife. 2016;5:e18722. Published Nov. 15, 2016. doi: 10.7554/eLife.18722. 21 pages.

Kisselev, Polypeptide release factors in prokaryotes and eukaryotes: same function, different structure. Structure. Jan. 2002;10(1):8-9. doi: 10.1016/s0969-2126(01)00703-1.

Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.

Kobayashi et al., Comparative Physiology and Biochemistry, 2005, vol. 22, No. 3-4, pp. 139-148.

Kolinko et al., Single-cell genomics reveals potential for magnetite and greigite biomineralization in an uncultivated multicellular magnetotactic prokaryote. Environ Microbiol Rep. Oct. 2014;6(5):524-31. doi: 10.1111/1758-2229.12198. Epub Aug. 28, 2014. Abstract Only.

Krylova et al., DNA aptamers for as analytical tools for the quantitative analysis of DNA-dealkylating enzymes. Anal Biochem. 2011;414(2):261-265. doi:10.1016/j.ab.2011.03.010.

Kumar et al., PEG-labeled nucleotides and nanopore detection for single molecule DNA sequencing by synthesis. Sci Rep. 2012;2:684. Epub Sep. 21, 2012.

Langecker et al., Synthetic lipid membrane channels formed by designed DNA nanostructures. Science. Nov. 16, 2012;338(6109):932-6. doi: 10.1126/science.1225624.

Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.

Li et al., ChIA-PET tool for comprehensive chromatin interaction analysis with paired-end tag sequencing. Genome Biol. 2010;11(2):R22. doi: 10.1186/GB-2010-11-2-r22. Epub Feb. 25, 2010.

Li et al., Different Anomeric Sugar Bound States of Maltose Binding Protein Resolved by a Cytolysin A Nanopore Tweezer. ACS Nano. 2020;14(2):1727-1737. doi:10.1021/acsnano.9b07385.

Li et al., DNA molecules and configurations in a solid-state nanopore microscope. Nat Mater. Sep. 2003;2(9):611-5. Epub Aug. 24, 2003.

Li, Minimap2: pairwise alignment for nucleotide sequences. Bioinformatics. 2018;34(18):3094-3100. doi: 10.1093/bioinformatics/bty191.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Loferer et al., Availability of the fibre subunit CsgA and the nucleator protein CsgB during assembly of fibronectin-binding curli is limited by the intracellular concentration of the novel lipoprotein CsgG. Mol Microbiol. 1997;26(1):11-23. doi:10.1046/j.1365-2958.1997.5231883.x.

Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.

Lu et al., Expression, purification and structural analysis of csgF gene of curli systems from *Escherichia coli* CFT073. Microbiol China. 2016, 43(9):2063-2071. doi:10.13344/j.microbiol.china.150752.

Lu et al., Protein Motion and Configurations in a Form-Fitting Nanopore: Avidin in ClyA. Biophys J. Sep. 4, 2018; 115(5):801-808. Epub Aug. 4, 2018. doi: 10.1016/j.bpj.2018.07.024.

Luchian et al., Single-Molecule Covalent Chemistry with Spatially Separated Reactants. Angew. Chem. Int. Ed. 2003;42:3766-771.

Ludtke, Single-Particle Refinement and Variability Analysis in EMAN2.1. Methods Enzymol. 2016;579:159-89. doi: 10.1016/bs.mie.2016.05.001. Epub Jul. 1, 2016.

Ludwig et al., Analysis of the SlyA-Controlled Expression, Subcellular Localization and Pore-Forming Activity of a 34 kDa Haemolysin (ClyA) from *Escherichia coli* K-12. Mol Microbiol. 1999;31(2):557-67.

Luo et al., Influence of polymer-pore interactions on translocation. Phys Rev Lett. Oct. 5, 2007;99(14):148102. Epub Oct. 1, 2007.

Maglia et al., DNA strands from denatured duplexes are translocated through engineered protein nanopores at alkaline pH. Nano Lett. Nov. 2009;9(11):3831-6. doi: 10.1021/nl9020232.

Maglia et al., Engineering a Biomimetic Biological Nanopore to Selectively Capture Folded Target Proteins. Biophysical J. Feb. 5, 2013;104(2):518a.

Maglia et al., Enhanced translocation of single DNA molecules through alpha-hemolysin nanopores by manipulation of internal charge. Proc Natl Acad Sci U S A. Dec. 16, 2008;105(50):19720-5. doi: 10.1073/pnas.0808296105. Epub Dec. 5, 2008.

Makaram et al., Trends in Nanomaterial-Based Non-Invasive Diabetes Sensing Technologies. Diagnostics. Apr. 21, 2014;4:27-46.

(56)           References Cited

OTHER PUBLICATIONS

Manrao et al., Nucleotide Discrimination with DNA Immobilized in the MspA Nanopore. PLoS One, vol. 6(10):e25723, 7 pages (2011).

Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.

Manrao et al., Single Nucleotide Discrimination in Single Stranded DNA Immobilized within Biological Nanopre MSPA. 54th Annual Meeting of the Biophysical Society, 3 pages (2010).

Martin et al., Nanoscale protein pores modified with PAMAM dendrimers. J Am Chem Soc. Aug. 8, 2007;129(31):9640-9. Epub Jul. 18, 2007.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Mikheyev et al., A First Look at the Oxford Nanopore MinION Sequencer. Mol Ecol Res. 2014;14:1097-1102.

Miles et al., The Staphylococcal Leukocidin Bicomponent Toxin Forms Large Ionic Channels. Biochemistry. Jun. 28, 2001;40:8514-522.

Mitchell et al., Chemical tags facilitate the sensing of individual DNA strands with nanopores. Angew Chem Int Ed Engl. 2008;47(30):5565-8. doi:10.1002/anie.200800183.

Miyazaki et al., MEGAWHOP Cloning: A Method of Creating Random Mutagenesis Libraries via Megaprimer PCR of Whole Plasmids. Methods in Enzymology. 2011;498:399-406.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Moreau et al., Coupling ion channels to receptors for biomolecule sensing. Nat Nanotechnol. Oct. 2008;3(10):620-5. doi: 10.1038/nnano.2008.242. Epub Sep. 7, 2008.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Moyer et al., Correlation Between Sweat Glucose and Blood Glucose in Subjects with Diabetes. Diabetes Technol Ther. 2012;14(5):398-402.

Mueller et al., RCSB Protein Data Bank No. 2WCD. Mar. 11, 2009. doi: 10.2210/pdb2WCD/pdb. 5 pages.

Mueller et al., The Structure of Cytolytic alpha-Helical Toxin Pore Reveals its Assembly Mechanism. Nature. Jun. 4, 2009;459:726-731.

Mueller et al., The Structure of Cytolytic alpha-Helical Toxin Pore Reveals its Assembly Mechanism. Nature. Jun. 4, 2009;459:Supplemental Information.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Mund et al., LEGO-NMR spectroscopy: a method to visualize individual subunits in large heteromeric complexes. Angew Chem Int Ed Engl. Oct. 18, 2013;52(43):11401-5. doi: 10.1002/anie.201304914. Epub Aug. 14, 2013.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R 1365-R1393 (2003).

Niedzwiecki et al., Inspection of the Engineered FhuA deltaC/delta4L Protein Nanopore by Polymer Exclusion. Biophys J. Nov. 2012;103:2115-124.

Nikolaidou et al., alpha-Ketoglutarate: Biological Effects of a Novel Biomarker of Heart Failure. Heart. Sep. 2010;96(17). 2 pages.

Nivala et al., Unfoldase-mediated protein translocation through an a-hemolysin nanopore. Nat Biotechnol. Mar. 2013;31(3):247-50. doi: 10.1038/nbt.2503. Epub Feb. 3, 2013. Author Manuscript, 10 pages.

Notice of Opposition for European Patent No. EP3097210 dated Aug. 12, 2019.

Ogasawara et al., Determination of Reduced Nicotinamide Adenine Dinucleotid Phosphate Concentration Using High-Performance Liquid Chromatography with Fluorescence Detection: Ratio of the Reduced Form as a Biomarker of Oxidative Stress. Biol Pharm Bull. Nov. 2009;32(11):1819-18223.

Oukhaled et al., Dynamics of Completely Unfolded and Native Proteins through Solid-State Nanopores as a Function of Electric Driving Force. Am Chem Soc. Arp. 8, 2011;5(5):3628-38.

Pavlenok et al., Hetero-oligomeric MspA pores in *Mycobacterium smegmatis*. FEMS Microbiol Lett. Apr. 2016;363(7). pii: fnw046. doi:10.1093/femsle/fnw046. Epub Feb. 23, 2016.

Pavlenok et al., MspA nanopores from subunit dimers. PLoS One. 2012;7(6):e38726. doi: 10.1371/journal.pone.0038726. Epub Jun. 18, 2012.

Peabody et al., Type II protein secretion and its relationship to bacterial type IV pili and archaeal flagella. Microbiology. Nov. 2003; 149(Pt 11):3051-3072. doi: 10.1099/mic.0.26364-0.

Pfeiffer et al., Bivalent cholesterol-based coupling of oligonucleotides to lipid membrane assemblies. J Am Chem Soc. Aug. 25, 2004;126(33):10224-5.

Plesa et al., Fast Translocation of Proteins through Solid State Nanopores. Nano Lett. Jan. 23, 2013:13:658-663.

Pud et al., Mechanical Trapping of DNA in a Double-Nanopore System. Nano Lett. 2016;16(12):8021-8028. doi:10.1021/acs.nanolett.6b04642.

Purnell et al., Nucleotide identification and orientation discrimination of DNA homopolymers immobilized in a protein nanopore. Nano Lett. Sep. 2008;8(9):3029-34. doi: 10.1021/nl802312f. Epub Aug. 13, 2008.

Quick et al., A reference Bacterial Genome Dataset Generated on the MinION Portable Single-Molecule Nanopore Sequencer. GigaScience. 2014;3(22):1-6.

Rajagopalan et al., Interaction of Dihydrofolate Reductase with Methotrexate: Ensemble and Single-Molecule Kinetics. PNAS. Oct. 15, 2002:99(21):13481-6.

Rasko et al., The pangenome structure of *Escherichia coli:* comparative genomic analysis of *E. coli* commensal and pathogenic isolates. J Bacteriol. Oct. 2008;190(20):6881-93. doi:10.1128/JB.00619-08. Epub Aug. 1, 2008.

Reznikoff, Tn5 as a model for understanding DNA transposition. Mol Microbiol. Mar. 2003;47(5):1199-206. doi: 10.1046/j.1365-2958.2003.03382.x.

Rhee et al., Comprehensive genome-wide protein-DNA interactions detected at single-nucleotide resolution. Cell. Dec. 9, 2011;147(6):1408-19. doi: 10.1016/j.cell.2011.11.013.

Rhee et al., Nanopore sequencing technology: research trends and applications. Trends Biotechnol. Dec. 2006;24(12):580-6. Epub Oct. 19, 2006.

(56) References Cited

OTHER PUBLICATIONS

Robinson et al., Secretion of curli fibre subunits is mediated by the outer membrane-localized CsgG protein. Mol Microbiol. Feb. 2006;59(3):870-81. doi: 10.1111/j.1365-2958.2005.04997.x.

Rodriguez-Gallego et al., Mapping of the Circulating Metabolome Reveals alpha-Ketoglutarate as a Predictor of Morbid Obesity-Associated Non-Alcoholic Fatty Liver Disease. Int J of Obesity. 2015;39:279-287.

Rohou et al., CTFFIND4: Fast and accurate defocus estimation from electron micrographs. J Struct Biol. Nov. 2015;192(2):216-21. doi: 10.1016/j.jsb.2015.08.008. Epub Aug. 13, 2015.

Rotem et al., Protein detection by nanopores equipped with aptamers. J Am Chem Soc. Feb. 8, 2012;134(5):2781-7. doi:10.1021/ja2105653. Epub Jan. 26, 2012.

Rucker et al., Recombinant ferritin: modulation of subunit stoichiometry in bacterial expression systems. Protein Eng. 1997;10(8):967-973. doi:10.1093/protein/10.8.967.

Russo et al., Reversible permeabilization of plasma membranes with an engineered switchable pore. Nat Biotechnol. Mar. 1997;15(3):278-82.

Saariaho et al., Characteristics of MuA transposase-catalyzed processing of model transposon end DNA hairpin substrates. Nucleic Acids Res. Jun. 6, 2006;34(10):3139-49.

Sanchez-Quesada et al., Cyclic Peptides as Molecular Adapters for a Pore-Forming Protein. Journal American Chemical Society, vol. 122(48):11757-11766 (2000).

Sanchez-Quesada et al., Single DNA rotaxanes of a transmembrane pore protein. Angew Chem Int Ed Engl. Jun. 7, 2004;43(23):3063-7.

Sanderson, Personal genomes: Standard and pores. Nature. Nov. 6, 2008;456(7218):23-5. doi: 10.1038/456023a.

Sauer-Budge et al., Unzipping kinetics of double-stranded DNA in a nanopore. Phys Rev Lett. Jun. 13, 2003;90(23):238101. Epub Jun. 9, 2003.

Scheres, Relion: implementation of a Bayesian approach to cryo-EM structure determination. J Struct Biol. Dec. 2012;180(3):519-30. doi: 10.1016/j.jsb.2012.09.006. Epub Sep. 19, 2012.

Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.

Sivanathan et al., Generating extracellular amyloid aggregates using E. coli cells. Genes Dev. Dec. 1, 2012;26(23):2659-67. doi: 10.1101/gad.205310.112. Epub Nov. 19, 2012.

Skocaj et al., The sensing of membrane microdomains based on pore-forming toxins. Curr Med Chem. 2013;20(4):491-501.

Smeets et al., Salt dependence of ion transport and DNA translocation through solid-state nanopores. Nano Lett. Jan. 2006;6(1):89-95.

Soni et al., Synchronous optical and electrical detection of biomolecules traversing through solid-state nanopores. Rev Sci Instrum. Jan. 2010;81(1):014301. doi: 10.1063/1.3277116.

Soskine et al., An engineered ClyA nanopore detects folded target proteins by selective external association and pore entry. Nano Lett. Sep. 12, 2012;12(9):4895-900. doi:10.1021/nl3024438. Epub Aug. 6, 2012. Author Manuscript, 13 pages.

Soskine et al., Single-Molecule Analyte Recognition with ClyA Nanopores Equipped with Internal Protein Adaptors. J Am Chem Soc. 2015;137:5793-97.

Soskine et al., Tuning the size and properties of ClyA nanopores assisted by directed evolution. J Am Chem Soc. Sep. 11, 2013;135(36):13456-63. doi: 10.1021/ja4053398. Epub Aug. 27, 2013.

Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Sutherland et al., An analysis of mismatched duplex DNA unzipping through a bacterial nanopore. Biochem Cell Biol. Jun. 2004;82(3):407-12.

Taylor et al., Atomic resolution insights into curli fiber biogenesis. Structure. Sep. 7, 2011;19(9):1307-16. doi: 10.1016/j.str.2011.05.015.

Taylor et al., New insight into the molecular control of bacterial functional amyloids. Front Cell Infect Microbiol. Apr. 8, 2015;5:33. doi: 10.3389/fcimb.2015.00033.

Third Party Observation for Application No. EP 15759438.3, mailed Oct. 20, 2022. 11 pages.

Third Party Observation for Application No. EP 15759438.3, mailed Sep. 17, 2021. 21 pages.

Third Party Observation for Application No. EP 18734933.7, mailed Apr. 11, 2022. 14 pages.

Third Party Observation for European Application No. EP18734933.7, mailed Sep. 27, 2021.

Trewick et al., Oxidative Demethylation by Escherichia coli AlkB Directly Reverts DNA Base Damage. Nature. Sep. 12, 2002;419:174-78.

Tuteja et al., Helicases as molecular motors: An insight. Physica A. Dec. 1, 2006;372(1):70-83. doi: 10.1016/j.physa.2006.05.014. Epub Jun. 5, 2006.

Van De Goor, Nanopore Detection: Threading DNA Through a Tiny Hole. PharmaGenomics, vol. 4 (3):28-30 (2004).

Van Der Verren et al., A dual-constriction biological nanopore resolves homonucleotide sequences with high fidelity. Nat Biotechnol. Dec. 2020;38(12):1415-1420. doi: 10.1038/s41587-020-0570-8. Epub Jul. 6, 2020. Author Manuscript, 25 pages.

Van Gerven et al., Bacterial amyloid formation: structural insights into curli biogenesis. Trends Microbiol. Nov. 2015; 23(11):693-706. EPub Oct. 1, 2015. doi: 10.1016/j.tim.2015.07.010. Author Manuscript, 24 pages.

Van Gerven et al., Secretion and functional display of fusion proteins through the curli biogenesis pathway. Mol Microbiol. Mar. 2014;91(5):1022-35. doi:10.1111/mmi.12515. Epub Feb. 12, 2014.

Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f. Author Manuscript, 16 pages.

Van Meervelt et al., Detection of Two Isomeric Binding Configurations in a Protein-Aptamer Complex with a Biological Nanopore. Am Chem Soc. Dec. 10, 2014;8(12):12826-35.

Van Meervelt et al., Real-Time Conformational Changes and Controlled Orientation of Native Proteins Inside a Protein Nanoreactor. J Am Chem Soc. Dec. 27, 2017; 139(51): 18640-18646. EPub Dec. 5, 2017. doi: 10.1021/jacs.7b10106.

Walker et al., Assembly of the oligomeric membrane pore formed by Staphylococcal alpha-hemolysin examined by truncation mutagenesis. J Biol Chem. Oct. 25, 1992;267(30):21782-6.

Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.

Wallace et al., E. coli hemolysin E (HlyE, ClyA, SheA): X-ray crystal structure of the toxin and observation of membrane pores by electron microscopy. Cell. Jan. 21, 2000;100(2):265-76.

Wang et al., Engineering of protein nanopores for sequencing, chemical or protein sensing and disease diagnosis. Curr Opin Biotechnol. Jun. 2018;51:80-89. doi: 10.1016/j.copbio.2017.11.006. Epub Dec. 10, 2017.

Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.

Wang et al., Nanopores with a spark for single-molecule detection. Nat Biotechnol. Jul. 2001;19(7):622-3.

Wang et al., Protein engineering with non-natural amino acids. InTechOpen; Feb. 24, 2012. DOI: 10.5772/28719.

(56) References Cited

OTHER PUBLICATIONS

Wanunu et al., DNA translocation governed by interactions with solid-state nanopores. Biophys J. Nov. 15, 2008;95(10):4716-25. doi: 10.1529/biophysj.108.140475. Epub Aug. 15, 2008.

Wanunu, Nanopores: A journey towards DNA sequencing. Phys Life Rev. Jun. 2012;9(2):125-58. doi:10.1016/j.plrev.2012.05.010. Epub May 18, 2012.

Welford et al., The Selectivity and Inhibition of AlkB. J. Biol. Chem. Mar. 21, 2003;278(12):10157-161.

Wendell et al., Translocation of double-stranded DNA through membrane-adapted phi29 motor protein nanopores. Nat Nanotechnol. 2009;4(11):765-772. doi:10.1038/nnano.2009.259.

Whisstock et al., Prediction of protein function from protein sequence and structure. Q Rev Biophys. Aug. 2003;36(3):307-40. doi: 10.1017/s0033583503003901.

White et al., Single Ion-Channel Recordings Using Glass Nanopore Membranes. J Am Chem Soc. 2007;129:11766-775.

Wiedmann et al., Ligase chain reaction (LCR)—overview and applications. PCR Methods Appl. Feb. 1994;3(4):S51-64. doi: 10.1101/gr.3.4.s51.

Wilkinson et al., Bacterial DNA ligases. Mol Microbiol. Jun. 2001;40(6):1241-8. doi: 10.1046/j.1365-2958.2001.02479.x.

Willems et al., Single-molecule nanopore enzymology. Philos Trans R Soc Lond B Biol Sci. Aug. 5, 2017;372(1726):20160230. doi: 10.1098/rstb.2016.0230. 11 pages.

Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

Wolfe et al., Catalyzing the translocation of polypeptides through attractive interactions. J Am Chem Soc. Nov. 14, 2007;129(45): 14034-41. Epub Oct. 19, 2007.

Wong et al., Polymer capture by electro-osmotic flow of oppositely charged nanopores. J Chem Phys. Apr. 28, 2007;126(16):164903.

Wu et al., Protein nanopores with covalently attached molecular adapters. J Am Chem Soc. Dec. 26, 2007;129(51): 16142-8. Epub Nov. 30, 2007.

Wu et al., Sequence-specific capture of protein-DNA complexes for mass spectrometric protein identification. PLoS One. 2011;6(10):e26217. doi: 10.1371/journal.pone.0026217. Epub Oct. 20, 2011.

Wu et al., Single-molecule detection of nitrogen mustards by covalent reaction within a protein nanopore. J Am Chem Soc. May 28, 2008;130(21):6813-9. doi: 10.1021/ja8004607. Epub Apr. 30, 2008.

Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.

Yoo et al., Glucose Biosensors: An Overview of Use in Clinical Practice. Sensores. May 4, 2010;10:4558-4576.

Zernia et al., Current Blockades of Proteins inside Nanopores for Real-Time Metabolome Analysis. ACS Nano. Feb. 25, 2020; 14(2): 2296-2307. EPub Jan. 31, 2020. doi: 10.1021/acsnano.9b09434.

Zernia et al., Current Blockades of Proteins inside Nanopores for Real-Time Metabolome Analysis. ACS Nano. Feb. 25, 2020; 14(Supplemental Information). EPub Jan. 31, 2020. doi: 10.1021/acsnano. 9b09434. 19 pages.

Zheng et al., MotionCor2: anisotropic correction of beam-induced motion for improved cryo-electron microscopy. Nat Methods. Apr. 2017;14(4):331-332. doi: 10.1038/nmeth.4193. Epub Feb. 27, 2017.

Zhou et al., Ion Channel Probes for Scanning Ion Conductance Microscopy. Langmuir. Nov. 25, 2014;30:15351-355.

[No Author Listed] BIAcore—Concentration Analysis Handbook, BR-1005-12 Edition AB, GE Healthcare, (2001), Dec. 1, 2001.

[No Author Listed] EMBL Accession No. VEG07918, Mycobacteroides chelonae MspA protein; Pathogen Informatics, Dec. 19, 2018. 1 page.

[No Author Listed] UniParc, UPI0021C2482E, Sep. 29, 2022. 2 pages.

Abbasov et al., A proteome-wide atlas of lysine-reactive chemistry. Nat Chem. Nov. 2021;13(11):1081-1092. doi: 10.1038/s41557-021-00765-4. Epub Sep. 9, 2021.

Baggio et al., Aryl-fluorosulfate-based Lysine Covalent Pan-Inhibitors of Apoptosis Protein (IAP) Antagonists with Cellular Efficacy. J Med Chem. Oct. 24, 2019;62(20):9188-9200. doi: 10.1021/acs.jmedchem.9b01108. Epub Oct. 8, 2019. Author Manuscript, 28 pages.

Berezovski et al., Non-SELEX selection of aptamers. J Am Chem Soc. Feb. 8, 2006;128(5):1410-1. doi: 10.1021/ja056943j.

Bird et al., Single-chain antigen-binding proteins. Science. Oct. 21, 1988;242(4877):423-6. doi: 10.1126/science.3140379.

Bock et al., Selection of single-stranded DNA molecules that bind and inhibit human thrombin. Nature. Feb. 6, 1992;355(6360):564-6. doi: 10.1038/355564a0.

Camacho et al., BLAST+: architecture and applications. BMC Bioinformatics. Dec. 15, 2009;10:421. doi: 10.1186/1471-2105-10-421.

Eilers et al., Internal packing of helical membrane proteins. Proc Natl Acad Sci U S A. May 23, 2000;97(11):5796-801. doi: 10.1073/pnas.97.11.5796.

Gambini et al., Covalent Inhibitors of Protein-Protein Interactions Targeting Lysine, Tyrosine, or Histidine Residues. J Med Chem. Jun. 13, 2019;62(11):5616-5627. doi: 10.1021/acs.jmedchem. 9b00561. Epub May 29, 2019. Author Manuscript, 26 pages.

Gilbert et al., Profiling Sulfur(VI) Fluorides as Reactive Functionalities for Chemical Biology Tools and Expansion of the Ligandable Proteome. ACS Chem Biol. Feb. 17, 2023;18(2):285-295. doi: 10.1021/acschembio.2c00633. Epub Jan. 17, 2023.

Hayes et al., Approaches for peptide and protein cyclisation. Org Biomol Chem. May 12, 2021;19(18):3983-4001. doi: 10.1039/dlob00411e.

Hoppmann et al., Proximity-enabled bioreactivity to generate covalent peptide inhibitors of p53-Mdm4. Chem Commun (Camb). Apr. 14, 2016;52(29):5140-3. doi: 10.1039/c6cc01226d. Epub Mar. 21, 2016 with Supporting Information, 7 pages.

Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83. doi: 10.1073/pnas.85.16.5879.

Leaver-Fay et al., ROSETTA3: an object-oriented software suite for the simulation and design of macromolecules. Methods Enzymol. 2011;487:545-74. doi: 10.1016/B978-0-12-381270-4.00019-6.

McGuffin et al., The PSIPRED protein structure prediction server. Bioinformatics. Apr. 2000;16(4):404-5. doi: 10.1093/bioinformatics/16.4.404.

Powl et al., Chimeric bacterial-human NaV1. 7 sodium channels expressed in *E. coli*. Biophysical Journal. Feb. 1, 2009;96(3):13a.

Remaut et al., Protein-protein interaction through beta-strand addition. Trends Biochem Sci. Aug. 2006;31(8):436-44. Epub Jul. 7, 2006.

Shannon et al., Covalent protein modification: the current landscape of residue-specific electrophiles. Curr Opin Chem Biol. Feb. 2015;24:18-26. doi: 10.1016/j.cbpa.2014.10.021. Epub Nov. 11, 2014.

Shiraiwa et al., Chemical Tools for Endogenous Protein Labeling and Profiling. Cell Chem Biol. Aug. 20, 2020;27(8):970-985. doi: 10.1016/j.chembiol.2020.06.016. Epub Jul. 16, 2020.

Stoddart et al., Nucleobase recognition in ssDNA at the central constriction of the alpha-hemolysin pore. Nano Lett. Sep. 8, 2010;10(9):3633-7. doi: 10.1021/nl101955a.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009. Supplementary Information, 9 pages.

Stoltenburg et al., SELEX—a (r)evolutionary method to generate high-affinity nucleic acid ligands. Biomol Eng. Oct. 2007;24(4):381-403. doi: 10.1016/j.bioeng.2007.06.001. Epub Jun. 16, 2007.

Tamura et al., Chemistry for Covalent Modification of Endogenous/Native Proteins: From Test Tubes to Complex Biological Systems. J Am Chem Soc. Feb. 20, 2019;141(7):2782-2799. doi: 10.1021/jacs.8b11747. Epub Jan. 8, 2019.

(56)                    References Cited

OTHER PUBLICATIONS

Tuerk et al., Systematic evolution of ligands by exponential enrichment: RNA ligands to bacteriophage T4 DNA polymerase. Science. Aug. 3, 1990;249(4968):505-10. doi: 10.1126/science.2200121.

Walther et al., Principles of helix-helix packing in proteins: the helical lattice superposition model. J Mol Biol. Jan. 26, 1996;255(3):536-53. doi: 10.1006/jmbi.1996.0044.

Ward et al., Binding activities of a repertoire of single immunoglobulin variable domains secreted from *Escherichia coli*. Nature. Oct. 12, 1989;341(6242):544-6. doi: 10.1038/341544a0.

Wen et al., A Guide to Signal Processing Algorithms for Nanopore Sensors. ACS Sens. Oct. 22, 2021;6(10):3536-3555. doi: 10.1021/acssensors.1c01618. Epub Oct. 4, 2021.

White et al., Generation of species cross-reactive aptamers using "toggle" SELEX. Mol Ther. Dec. 2001;4(6):567-73. doi: 10.1006/mthe.2001.0495.

Yamini et al., Hydrophobic Gating and 1/f Noise of the Anthrax Toxin Channel. J Phys Chem B. Jun. 3, 2021;125(21):5466-5478. doi: 10.1021/acs.jpcb.0c10490. Epub May 20, 2021.

Yan et al., Assembly and substrate recognition of curli biogenesis system. Nat Commun. Jan. 13, 2020;11(1):241. doi: 10.1038/s41467-019-14145-7.

Zhang et al., Cryo-EM structure of the nonameric CsgG-CsgF complex and its implications for controlling curli biogenesis in Enterobacteriaceae. PLoS Biol. Jun. 19, 2020;18(6):e3000748. doi: 10.1371/journal.pbio.3000748.

Zhou et al., Rapid search for tertiary fragments reveals protein sequence-structure relationships. Protein Sci. Apr. 2015;24(4):508-24. doi: 10.1002/pro.2610. Epub Dec. 31, 2014.

* cited by examiner

Two reader-heads membrane current leakage here

- CP1-(AQ-R97C-StrepII(C))9
- CP1-(AQ-I107C-StrepII(C))9
- CP1-(AQ-R110C-StrepII(C))9
- CP1-(AQ-Q100C-StrepII(C))9
- CP1-(AQ-E101C-StrepII(C))9
- CP1-(AQ-N102C/L113C-StrepII(C))9
- CP1-(AQ-R97C/N102C-StrepII(C))9
- CP1-(AQ-R97C/E101C-StrepII(C))9

Dimer
From the x-structure

Monomer
From the prepore

F56Q/N55/Y51A

N55V

A51Q

Q56V

TRANSMEMBRANE PORE CONSISTING OF TWO CSGG PORES

RELATED APPLICATIONS

This Application is a continuation of U.S. application Ser. No. 16/610,895, filed Nov. 4, 2019, which is a national stage filing under 35 U.S.C. 371 of international application number PCT/GB2018/051191, filed May 3, 2018, which claims the benefit of United Kingdom application number 1707122.6, filed May 4, 2017, each of which is incorporated by reference it its entirety.

REFERENCE TO AN ELECTRONIC SEQUENCE LISTING

The contents of the electronic sequence listing (0036670092US01-SEQ-LJG.xml; Size: 33,200 bytes; and Date of Creation: May 17, 2024) is herein incorporated by reference in its entirety.

FIELD

The invention relates to CsgG pores and to methods of analyte detection and characterisation using CsgG pores.

BACKGROUND

Nanopore sensing is an approach to sensing that relies on the observation of individual binding or interaction events between analyte molecules and a receptor. Nanopore sensors can be created by placing a single pore of nanometer dimensions in an insulating membrane and measuring voltage-driven ionic transport through the pore in the presence of analyte molecules. The identity of an analyte is revealed through its distinctive current signature, notably the duration and extent of current block and the variance of current levels. Such nanopore sensors are commercially available, such as the MinION™ device sold by Oxford Nanopore Technologies Ltd, comprising an array of nanopores integrated with an electronic chip. Nanopore sensing has the potential to provide rapid and cheap nucleic acid sequencing by reducing the quantity of nucleotide and reagents required.

Two of the essential components of sequencing nucleic acids using nanopore sensing are (1) the control of nucleic acid movement through the pore and (2) the discrimination of nucleotides as the nucleic acid polymer is moved through the pore.

CsgG is a pore from *Escherichia coli* that has been proposed for use as a nanopore for detecting and characterising analytes. Mutations to the wild-type CgG pore that improve the properties of the pore in this context have also been disclosed (WO2016/034591).

SUMMARY

The inventors have demonstrated that double pores consisting of two CsgG pores in series can be used to detect and characterise analytes, such as polynucleotides. The double pores may be used in particular to facilitate characterization of polynucleotides that contain at least one homopolymeric stretch, i.e. several consecutive copies of the same nucleotide. Such double pores are provided, as are novel monomers that may be used to produce double pores for use in such methods. The monomers comprise amino acid residues that when assembled into a double pore strengthen the interactions between the two pores, amino acid residues that inhibit ions from exiting the pore at the junction between the two pores, amino acid residues that facilitate interaction of a negatively charged analyte, such as a polynucleotide, with one or both of the barrel regions of the pore and/or amino acid residues that increase the length of one or both of the two narrowest parts of the double pore, i.e. the constrictions in the barrels of the double pore. Also provided are CsgG pores comprising the novel monomers and the use of such pores in methods of characterising analytes.

Previously, several mutations in CsgG pores have sharpened the reader head in order to call bases accurately with available algorithms and analysis tools. Advancements in the algorithms and analysis tools means, we are not restricted to sharp reader heads anymore. The inventors have recognised that new algorithms can deal with longer reader heads which provide additional information that may be lacking in short sharp reader heads. Therefore, the inventors have reengineered the CsgG constriction to elongate the reader head. This may also help to call homopolymers with better accuracies.

In particular, the following are provided:

A method of characterising a polynucleotide using a transmembrane pore, wherein the pore is a double pore comprising a first CsgG pore, or a homologue thereof, and a second CsgG pore, or a homologue thereof.

A double pore comprising a first CsgG pore, or a homologue thereof, and a second CsgG pore, or a homologue thereof, wherein:

(i) the first CsgG pore, or homologue thereof, is a homooligomer and the second CsgG pore, or homologue thereof, is a homooligomer, and the first CsgG pore, or homologue thereof, comprises monomers that have a different amino acid sequence from the monomers of which the second CsgG pore, or homologue thereof, is comprised;

(ii) the first CsgG pore, or homologue thereof, is a homooligomer and the second CsgG pore, or homologue thereof, is a homooligomer, and the first CsgG pore, or homologue thereof, and/or the second CsgG pore, or homologue thereof is not a wild-type pore;

(iii) the first CsgG pore, or homologue thereof, is a heterooligomer and the second CsgG pore, or homologue thereof, is a homooligomer;

(iv) the first CsgG pore, or homologue thereof, is a homooligomer and the second CsgG pore, or homologue thereof, is a heterooligomer; or (v) the first CsgG pore, or homologue thereof, is a heterooligomer and the second CsgG pore, or homologue thereof, is a heterooligomer.

A CsgG monomer, or a monomer of a CsgG homologue, comprising:

(i) a cysteine residue at a position corresponding to R97, I107, R110, Q100, E101, N102 and or L113 of SEQ ID NO: 2;

(ii) a residue at a position corresponding to any one or more of R97, Q100, I107, R110, E101, N102 and L113 of SEQ ID NO: 2, which residue is more hydrophobic than the residue present at the corresponding position of SEQ ID NO: 2, or in the amino acid sequence of a wild type CsgG homologue, wherein the residue at the position corresponding to R97 and/or I107 is M, the residue at the position corresponding to R110 is I, L, V, M, W or Y, and/or the residue at the position corresponding to E101 or N102 is V or M;

(iii) a residue at a position corresponding to any one or more of A98, A99, T104, V105, L113, Q114 and S115 of SEQ ID NO: 2 which is bulkier than the residue present at the corresponding position of SEQ ID NO: 2, or in the amino acid sequence of a wild type CsgG homologue, wherein the residue at the position corresponding to T104 is L, M, F, W, Y, N, Q, D or E, the residue at the position corresponding to L113 is M, F, W, Y, N, G, D or E and/or the residue at the position corresponding to S115 is M, F, W, Y, N, Q or E; and/or (iv) a residue in the barrel region of the pore at a position corresponding to any one or more of D149, E185, D195, E210 and E203 which has less negative charge than the residue present at the corresponding position in the wild type CsgG monomer, or the wild type CsgG homologue monomer, wherein the residue at the position corresponding to D149, E185, D195 and/or E203 is K.

A construct comprising two or more covalently attached CsgG monomers, wherein at least one of the monomers is a monomer as disclosed herein;

A polynucleotide which encodes a monomer as disclosed herein or a construct as disclosed herein.

A pore comprising at least one monomer as disclosed herein or a construct as disclosed herein.

A method for determining the presence, absence or one or more characteristics of a target analyte, comprising: contacting the target analyte with a double pore as disclosed herein or a pore as disclosed herein such that the target analyte moves with respect to the pore; and taking one or more measurements as the analyte moves with respect to the pore and thereby determining the presence, absence or one or more characteristics of the analyte.

Use of a double pore as disclosed herein or a pore as disclosed herein to determine the presence, absence or one or more characteristics of a target analyte.

A kit for characterising a target analyte comprising (a) a double pore as disclosed herein or a pore as disclosed herein and (b) the components of a membrane.

An apparatus for characterising target analytes in a sample, comprising an array of double pores as disclosed herein or an array of pores as disclosed herein in a plurality of membranes.

A method of producing a monomer as disclosed hereinor a construct as disclosed herein, comprising expressing a polynucleotide as disclosed herein in a suitable host cell and thereby producing a monomer as disclosed hereinor a construct as disclosed herein.

DESCRIPTION OF THE FIGURES

FIG. 6A. Discrimination of bases against the reader head position. When dominant current level contributions are approximated to 5 bases within the reader head, middle base ($3^{rd}$) shows the major contribution to the signal whilst $1^{st}$, $2^{nd}$, $4^{th}$ and $5^{th}$ bases contribute at a relatively lower level ($1^{st}$ base is towards trans side of the pore and the $5^{th}$ base is towards the cis side of the pore). FIG. 6B. Separation of the four nucleotides at each reader head position when dominant current level contributions are approximated to 5 bases within the reader head. FIG. 6C. Example squiggle from the baseline pore.

FIG. 7A. Discrimination of bases against the reader head position. When dominant current level contributions are approximated to 5 bases within the reader head, $3^{rd}$ and $4^{th}$ bases show a major contribution to the signal whilst $1^{st}$, $2^{nd}$ and $5^{th}$ bases contribute at a relatively lower level ($1^{st}$ base is towards trans side and the $5^{th}$ base is towards the cis side). FIG. 7B. Separation of the four nucleotides at each reader head position when dominant current level contributions are approximated to 5 bases within the reader head. FIG. 7C. Example squiggle from the N55V pore.

FIG. 8A. Discrimination of bases against the reader head position. When dominant current level contributions are approximated to 5 bases within the reader head, $2^{nd}$ and $3^{rd}$ bases show the biggest contribution to the signal whilst $1^{st}$, $4^{th}$ and $5^{th}$ bases contribute at a relatively lower level ($1^{st}$ base is towards trans side of the pore and the $5^{th}$ base is towards the cis side of the pore). FIG. 8B. Separation of the four nucleotides at each reader head position when dominant current level contributions are approximated to 5 bases within the reader head. FIG. 8C. Example squiggle from the A51Q pore.

FIG. 9A. Discrimination of bases against the reader head position. When dominant current level contributions are approximated to 5 bases within the reader head, $2^{nd}$ and $3^{rd}$ bases show the biggest contribution to the signal whilst $1^{st}$, $4^{th}$ and $5^{th}$ bases contribute at a relatively lower level ($1^{st}$ base is towards trans side of the pore and the $5^{th}$ base is towards the cis side of the pore). FIG. 9B. Separation of the four nucleotides at each reader head position when dominant current level contributions are approximated to 5 bases within the reader head. FIG. 9C. Example squiggle from the Q56V pore.

DESCRIPTION OF THE SEQUENCE LISTING

Figure 1:
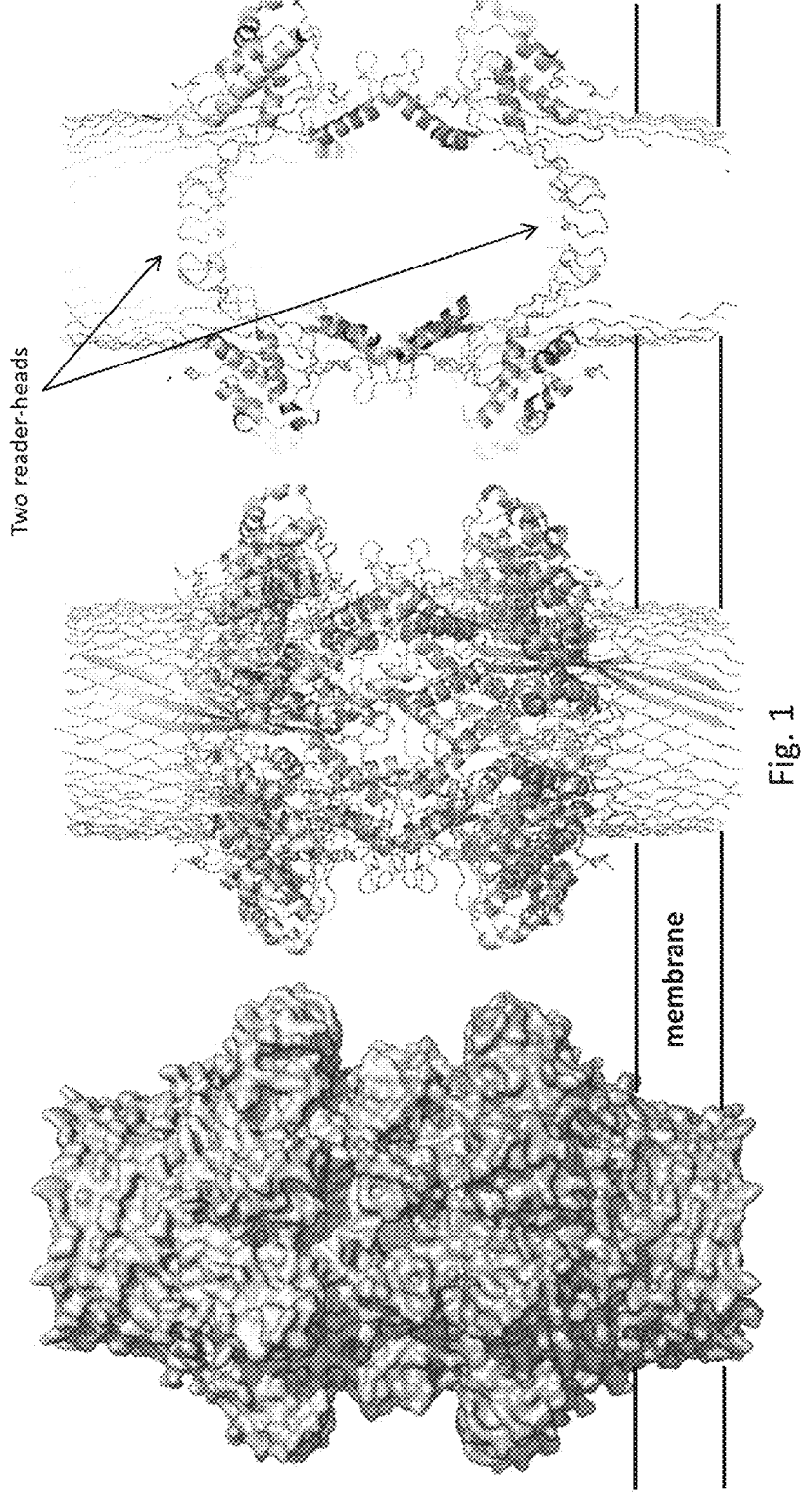
FIG. 1 shows the structure of a double pore comprising two CsgG pores in a tail to tail orientation. The two reader heads are indicated.
Figure 2:
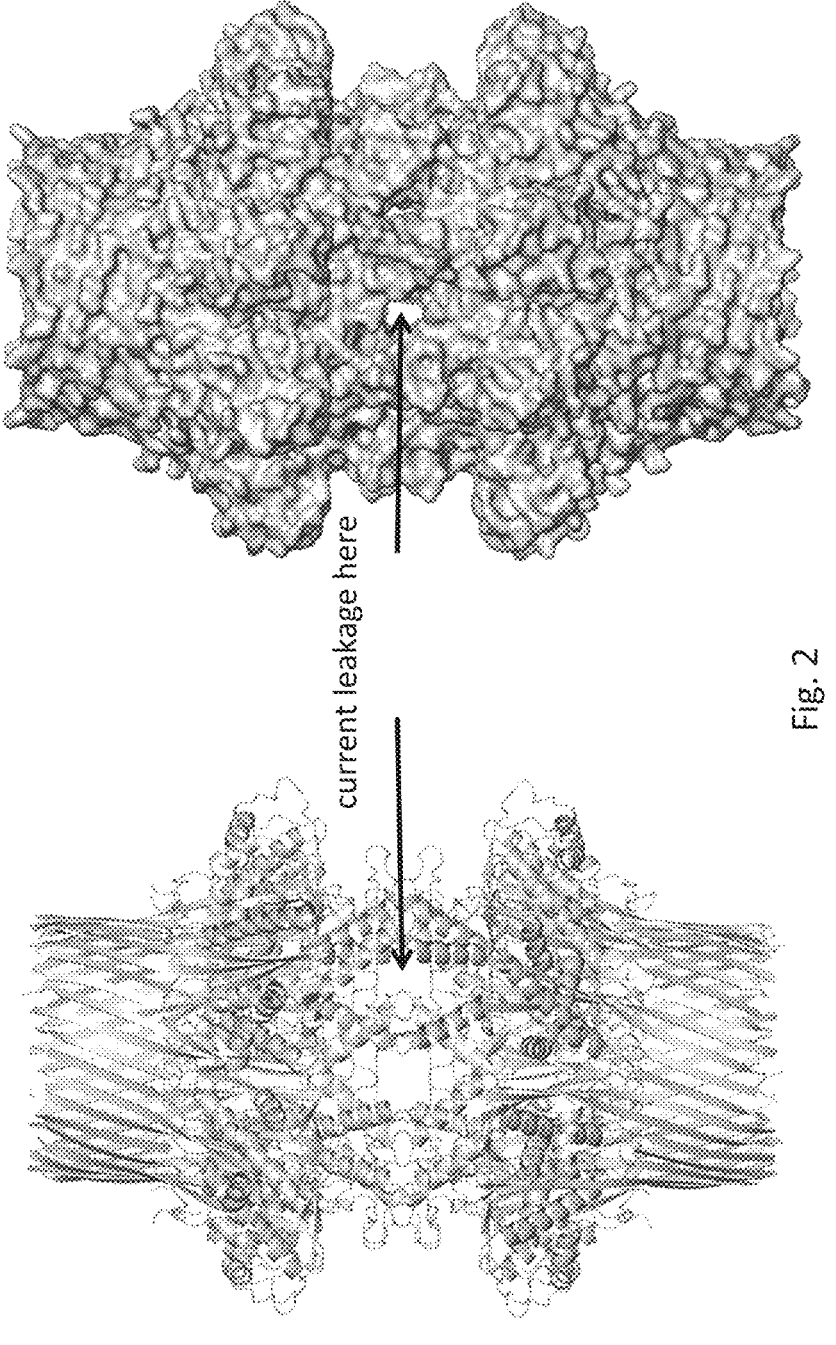
FIG. 2 shows holes in the walls of a CsgG double pore. The inventors have produced data suggesting that double pore current is less than half the single pore current (at higher voltages). The inventors have proposed that this could be due to current leak from side pockets at the interface of the two pores. These gaps can be filled in by changing one or more amino acid residues in this area to bulkier amino acid residues.
Figure 3:
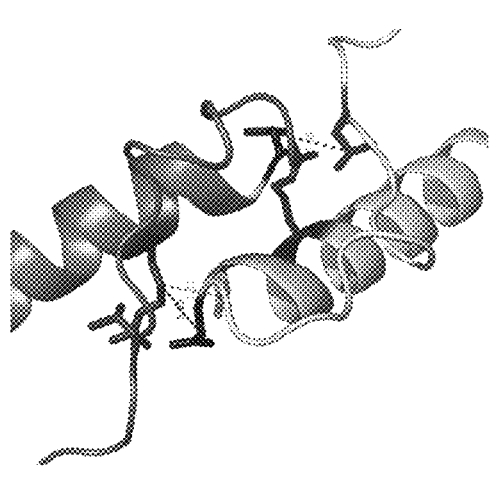
FIG. 3 shows the structure of part of the interface between two CsgG pores in a double pore (dimer). The mutations are shown in a pore that comprises Y51A and F56Q mutations (AQ=CP1-(WT-Y51A/F56Q-StrepU(C))9). The indicated Cys mutant pairs may form S—S bonds.
Figure 4:
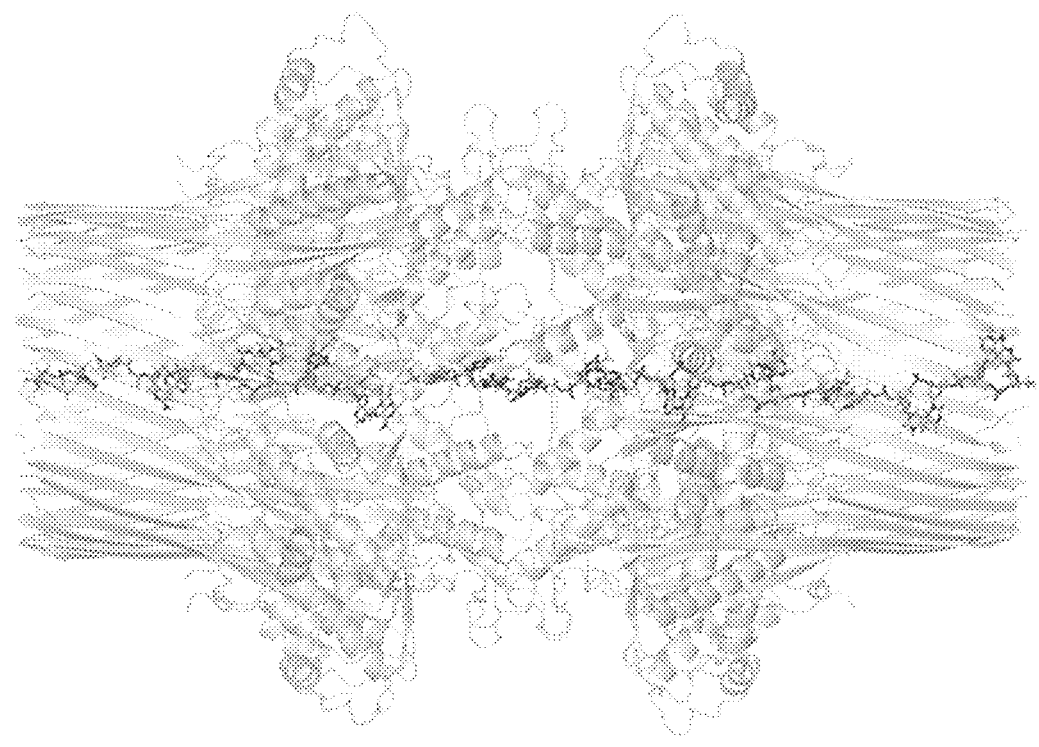
FIG. 4 shows the structure of part of a double pore with a single stranded DNA molecule inserted in the pore. There are approximately 15 nucleotides between the two constrictions (reader heads). The two reader-heads are separated by a non-DNA interacting region.
Figures 5A, 5B, 5C:
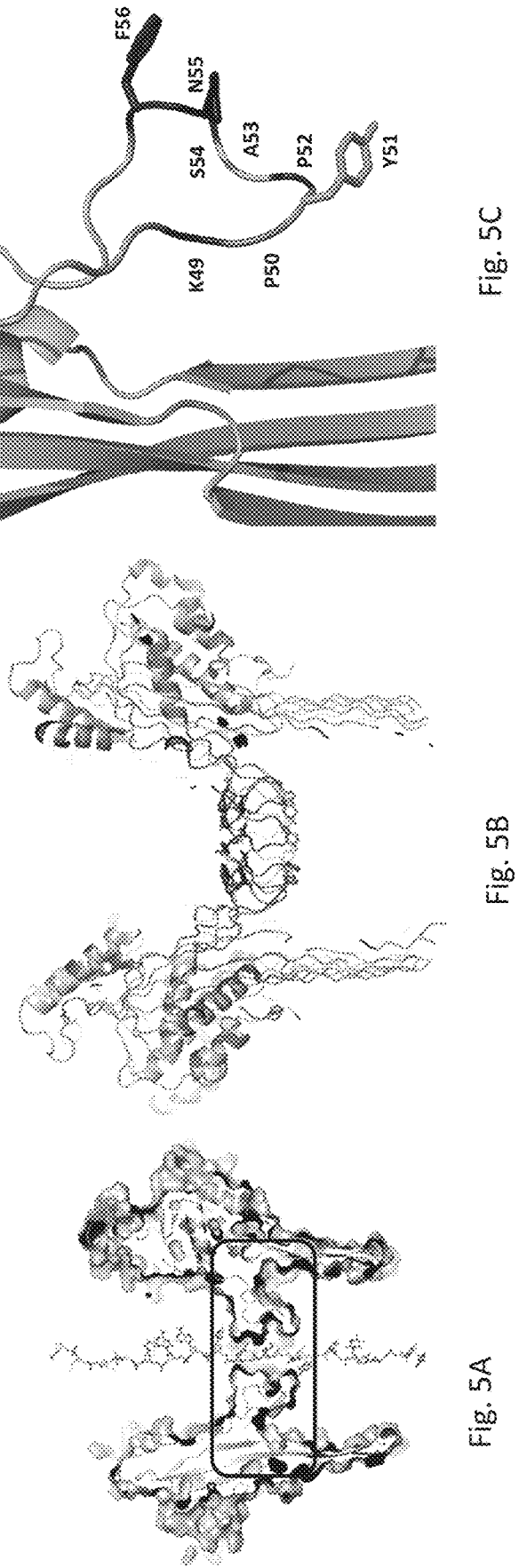
FIG. 5A shows the cross section of a CsgG pore showing the constriction (reader head) with a single stranded DNA inserted.
FIG. 5B shows the cross section of a wild type CsgG pore in which the three main amino acid residues, F56 (red), N55 (blue) and Y51 (green), are indicated. The constriction is located within the barrel (at the top) in a relatively unstructured loop. The reader head can be elongated either by mutations at existing positions or by inserting additional amino acid residues. For example, the reader head can be broadened by mutations at each of the three indicated positions and/or by mutations at the 52, 53 and 54 positions.
FIG. 5C shows the positions of the residues from K49 to F56 in a monomer of the CsgG pore. 51 can be moved further down by increasing the length of the loop in between 51 and 55. New amino acid residues can be inserted between 51 and 52, 52 and 53, 53 and 54 or 54 and 55. For example, 1, 2, 3 or more amino acid residues may be inserted. To keep the flexible nature of the loop, A/S/G/T can be inserted. To add a kink to the loop P can be inserted. New A amino acid residues could contribute to the signal (e.g. S/T/N/Q/M/F/W/Y/V/I). Similarly, new amino acids can be inserted between 55 and 56 (1 or 2 or more). They can be any of the above amino acids. Y51 can also move downwards by inserting amino acids to both sides of the loop above Y51. For example S or G or SG or SGG or SGS or GS or GSS or GSG or other suitable amino acid (1 or 2 or more) can be inserted (i) between (49 and 50) and between (52 and 53); (ii) between (50 and 51) and between (51 and 52); (iii) combinations of 1 and 2; or (iv) any of (i) to (iii) can be combined with other insertions (e.g. insertions between 55 and 56).

SEQ ID NO: 1 shows the codon optimised polynucleotide sequence encoding the wild-type CsgG monomer from *Escherchia coli* Str. K-12 substr. MC4100. This monomer lacks the signal sequence.

SEQ ID NO: 2 shows the amino acid sequence of the mature form of the wild-type CsgG monomer from *Escherchia coli* Str. K-12 substr. MC4100. This monomer lacks the signal sequence. The abbreviation used for this CsgG=CsgG-Eco.

SEQ ID NO: 3 shows the amino acid sequence of YP_001453594.1: 1-248 of hypothetical protein CKO_02032 [*Citrobacter koseri* ATCC BAA-895], which is 99% identical to SEQ ID NO: 2.

SEQ ID NO: 4 shows the amino acid sequence of WP_001787128.1: 16-238 of curli production assembly/ transport component CsgG, partial [*Salmonella enterica*], which is 98% to SEQ ID NO: 2.

SEQ ID NO: 5 shows the amino acid sequence of KEY44978.1|: 16-277 of curli production assembly/transport protein CsgG [*Citrobacter amalonaticus*], which is 98% identical to SEQ ID NO: 2.

SEQ ID NO: 6 shows the amino acid sequence of YP_003364699.1: 16-277 of curli production assembly/transport component [*Citrobacter rodentium* ICC168], which is 97% identical to SEQ ID NO: 2.

SEQ ID NO: 7 shows the amino acid sequence of YP_004828099.1: 16-277 of curli production assembly/transport component CsgG [*Enterobacter asburiae* LF7a], which is 94% identical to SEQ ID NO: 2.

SEQ ID NO: 8 shows the amino acid sequence of WP_006819418.1: 19-280 of transporter [*Yokenella regensburgei*], which is 91% identical to SEQ ID NO: 2.

SEQ ID NO: 9 shows the amino acid sequence of WP_024556654.1: 16-277 of curli production assembly/transport protein CsgG [*Cronobacter pulveris*], which is 89% identical to SEQ ID NO: 2.

SEQ ID NO: 10 shows the amino acid sequence of YP_005400916.1:16-277 of curli production assembly/transport protein CsgG [*Rahnella aquatilis* HX2], which is 84% identical to SEQ ID NO: 2.

SEQ ID NO: 11 shows the amino acid sequence of KFC99297.1: 20-278 of CsgG family curli production assembly/transport component [*Kluyvera ascorbata* ATCC 33433], which is 82% identical to SEQ ID NO: 2.

SEQ ID NO: 12 shows the amino acid sequence of KFC86716.1|:16-274 of CsgG family curli production assembly/transport component [*Hafnia alvei* ATCC 13337], which is 81% identical to SEQ ID NO: 2.

SEQ ID NO: 13 shows the amino acid sequence of YP_007340845.1|:16-270 of uncharacterised protein involved in formation of curli polymers [Enterobacteriaceae bacterium strain FGI 57], which is 76% identical to SEQ ID NO: 2.

SEQ ID NO: 14 shows the amino acid sequence of WP_010861740.1: 17-274 of curli production assembly/transport protein CsgG [*Plesiomonas shigelloides*], which is 70% identical to SEQ ID NO:2.

SEQ ID NO: 15 shows the amino acid sequence of YP_205788.1: 23-270 of curli production assembly/transport outer membrane lipoprotein component CsgG [*Vibrio fischeri* ES114], which is 60% identical to SEQ ID NO: 2.

SEQ ID NO: 16 shows the amino acid sequence of WP_017023479.1: 23-270 of curli production assembly protein CsgG [*Aliivibrio logei*], which is 59% identical to SEQ ID NO: 2.

SEQ ID NO: 17 shows the amino acid sequence of WP_007470398.1: 22-275 of Curli production assembly/transport component CsgG [*Photobacterium* sp. AK15], which is 57% identical to SEQ ID NO: 2.

SEQ ID NO: 18 shows the amino acid sequence of WP_021231638.1: 17-277 of curli production assembly protein CsgG [*Aeromonas veronii*], which is 56% identical to SEQ ID NO: 2.

SEQ ID NO: 19 shows the amino acid sequence of WP_033538267.1: 27-265 of curli production assembly/transport protein CsgG [*Shewanella* sp. ECSMB14101], which is 56% identical to SEQ ID NO: 2.

SEQ ID NO: 20 shows the amino acid sequence of WP_003247972.1: 30-262 of curli production assembly protein CsgG [*Pseudomonas putida*], which is 54% identical to SEQ ID NO: 2.

SEQ ID NO: 21 shows the amino acid sequence of YP_003557438.1: 1-234 of curli production assembly/transport component CsgG [*Shewanella violacea* DSS12], which is 53% identical to SEQ ID NO: 2.

SEQ ID NO: 22 shows the amino acid sequence of WP_027859066.1: 36-280 of curli production assembly/transport protein CsgG [*Marinobacterium jannaschii*], which is 53% identical to SEQ ID NO: 2.

SEQ ID NO: 23 shows the amino acid sequence of CEJ70222.1: 29-262 of Curli production assembly/transport component CsgG [*Chryseobacterium oranimense* G311], which is 50% identical to SEQ ID NO: 2.

SEQ ID NO: 24 shows the amino acid sequence of StrepII(C).

SEQ ID NO: 25 shows the DNA sequence encoding the polypeptide Pro-CP1-Eco-(Mutant-StrepII(C)).

SEQ ID NO: 26 shows the amino acid sequence of the polypeptide Pro-CP1-Eco-(Mutant-StrepII(C)).

DETAILED DESCRIPTION

It is to be understood that different applications of the disclosed products and methods may be tailored to the specific needs in the art. It is also to be understood that the terminology used herein is for the purpose of describing particular embodiments only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "a polynucleotide binding protein" includes two or more such proteins, reference to "a helicase" includes two or more helicases, reference to "a monomer" refers to two or more monomers, reference to "a pore" includes two or more pores and the like.

In all of the discussion herein, the standard one letter codes for amino acids are used. These are as follows: alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y) and valine (V). Standard substitution notation is also used, i.e. Q42R means that Q at position 42 is replaced with R.

In the paragraphs herein where different amino acids at a specific position are separated by the/symbol, the/symbol means "or". For instance, Q87R/K means Q87R or Q87K.

In the paragraphs herein where different positions are separated by the/symbol, the/symbol means "and" such that Y51/N55 is Y51 and N55.

All amino-acid substitutions, deletions and/or additions disclosed herein are with reference to a mutant CsgG monomer comprising a variant of the sequence shown in SEQ ID NO: 2, unless stated to the contrary.

Reference to a mutant CsgG monomer comprising a variant of the sequence shown in SEQ ID NO: 2 encompasses mutant CsgG monomers comprising variants of sequences as set out in the further SEQ ID NOS as disclosed below. Amino-acid substitutions, deletions and/or additions may be made to CsgG monomers comprising a variant of the sequence other than shown in SEQ ID NO:2 that are equivalent to those substitutions, deletions and/or additions disclosed herein with reference to a mutant CsgG monomer comprising a variant of the sequence shown in SEQ ID NO:2.

All publications, patents and patent applications cited herein, whether supra or infra, are hereby incorporated by reference in their entirety.

Double Pores

Provided is a double pore comprising a first CsgG pore, or a homologue thereof, and a second CsgG pore, or a homologue thereof.

The double pore may comprise a first CsgG pore, or homologue thereof, which is a homooligomer and a second CsgG pore, or homologue thereof, which is a homooligomer, wherein the first CsgG pore, or homologue thereof, comprises monomers that have a different amino acid sequence from the monomers of which the second CsgG pore, or homologue thereof, is comprised.

The double pore may comprise a first CsgG pore, or homologue thereof, which is a homooligomer and a second CsgG pore, or homologue thereof, which is a homooligomer, wherein the first CsgG pore, or homologue thereof, and/or the second CsgG pore, or homologue thereof, comprises monomers that comprises a non-naturally occurring amino acid sequence, i.e. wherein the sequence of the first pore and/or the second pore is not a wild-type sequence.

The double pore may comprise a first CsgG pore, or homologue thereof, which is a heterooligomer and a second CsgG pore, or homologue thereof, which is a homooligomer.

The double pore may comprise a first CsgG pore, or homologue thereof, which is a homooligomer and a second CsgG pore, or homologue thereof, which is a heterooligomer.

The double pore may comprise a first CsgG pore, or homologue thereof, which is a heterooligomer and a second CsgG pore, or homologue thereof, which is a heterooligomer.

The homooligomer may contain any number of monomers having identical amino acid sequences. The homooligomer typically comprises at least 7, at least 8, at least 9 or at least 10 identical mutant monomers, such as 7, 8, 9 or 10 mutant monomers. The homooligomer preferably comprises eight or nine identical monomers. One or more, such as 2, 3, 4, 5, 6, 7, 8, 9 or 10, of the monomers may be chemically modified as discussed herein. The homooligomer may comprise any of the modified monomers, such as a monomer of the invention, or wild type monomers. The monomers may have the amino acid sequence shown in any one of SEQ ID NOs: 2 to 23 or may be a variant of any one of these sequences. The variant may have any one or more of the mutations described herein. Where the homooligomer comprises wild type monomers, the double pore provided herein comprises only one such homooligomer. The homooligomer may be paired with a different homooligomer in the double pore, which may comprise wild type or mutant monomers, such as the modified monomers, such as a monomer of the invention. The homooligomer may be paired with a heterooligomer in the double pore.

The heterooligomer may contains any number of monomers sufficient to form a pore. The pore typically comprises at least 7, at least 8, at least 9 or at least 10 monomers, such as 7, 8, 9 or 10 monomers. The pore preferably comprises eight or nine monomers. The heterooligomer may comprises 2, 3, 4, 5, 6, 7, 8, 9 or 10 different monomers. At least one of the monomers in the heterooligomer differs from the others. All of the monomers in the heterooligomers may be different from one another. For example, each monomer may comprise a different mutation or group of mutations.

The heterooligomer may comprise at least one modified monomer, such as a monomer of the invention. All of the monomers (such as 10, 9, 8 or 7 of the monomers) may be monomers of the invention, wherein at least one of the monomers differs from the others. For example, the heterooligomer may comprise eight or nine monomers of the invention, wherein at least one of them differs from the others. They may all differ from one another.

At least one of the monomers may not be a monomer of the invention. For example, at least one of the monomers in the heterooligomer may be a mutant monomer which comprises mutations other than the mutations present in the monomers of the present invention. Suitable mutant monomers are known in the art, for example in WO2016/034591, PCT/GB2017/050569, PCT/GB2017/050570 and PCT/GB2017/050571. The mutant monomers disclosed in WO2016/034591, PCT/GB2017/050569, PCT/GB2017/050570 and PCT/GB2017/050571 are incorporated herein.

Any number of the monomers in the pore may not be a monomer of the invention, from 1, 2, 3, 4, 5, 6, 7, 8, 9 or 10 monomers. All of the monomers in at least one of the pores making up the double pore of the invention may not be monomers of the invention. The heterooligomer is preferably a nonomer that comprises seven or eight monomers of the invention, that may be the same or different, and one or two monomers which are not monomers of the invention, or is an octamer that comprises six or seven monomers of the invention, that may be the same or different, and one or two monomers which is not a monomer of the invention.

The heterooligomer may comprise roughly equal numbers of a first monomer and a second monomer, such as 5 of one and 4 of the other, 4 of each, or 3 of one and 4 of the other.

The first and second monomers may be different modified monomers, such as different monomers of the invention, only one of the first and second monomers may be a monomer of the invention, or both the first and second monomers may be monomers that are not monomers of the invention.

The monomers in the heterooligomer are preferably approximately the same length or are the same length. The barrels of the monomers of the invention in the pore are preferably approximately the same length or are the same length. Length may be measured in number of amino acids and/or units of length.

The pore may comprise one or more monomers which are not monomers of the invention. CsgG monomers, and monomers of CsgG homologues, which are not monomers of the invention include wild type monomers comprising the amino acid sequence shown in SEQ ID NO: 2 or in any one of SEQ ID NOs: 3 to 24. Variants of SEQ ID NOs: 2 to 23 may also be used. Such variants are typically at least 50% homologous to one or more of SEQ ID NOs: 2 to 23 over its entire sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 2 to 23 over the entire sequence.

One or more, such as 2, 3, 4, 5, 6, 7, 8, 9 or 10, of the monomers may be chemically modified.

The first and second pores in the double pore typically both comprise the same number of monomers. For example, where the first pore is nonomeric, the second pore is typically also nonomeric. The double pore may comprise two pores each comprising 2, 3, 4, 5, 6, 7, 8, 9 or 10 monomers, preferably 7, 8 or 10 monomers, more preferably 9 monomers.

The double pore is typically a transmembrane pore. The double pore may be associated with the membrane such the first pore and the second pore form a continuous channel through the membrane. Typically the first pore present in the double pore crosses the membrane and the second pore is located on the cis or trans side of the membrane. In this embodiment, the barrel of the first pore is typically inserted in the membrane and the tail of the first pore protrudes from the membrane. The first pore and the second pore may be orientated in opposite directions. The tail region of the first CsgG pore, or homologue thereof, may be adjacent to the tail region of the second CsgG pore, or homologue thereof. The tail of the first pore typically associates with the tail of the second pore.

In the double pore, the first CsgG pore, or homologue thereof, may be attached to the second CsgG pore, or homologue thereof, by hydrophobic interactions and/or by one or more disulphide bond. One or more, such as 2, 3, 4, 5, 6, 8, 9, for example all, of the monomers in the first pore and/or the second pore may be modified to enhance such interactions. This may be achieved in any suitable way.

At least one cysteine residue in the amino acid sequence of the first pore at the interface between the first and second pores may be disulphide bonded to at least one cysteine residue in the amino acid sequence of the second pore at the interface between the first and second pores. The cysteine residue in the first pore and/or the cysteine residue in the second pore may be a cysteine residue that is not present in the wild type CsgG monomer and/or in a wild type CsgG homologue monomer. Multiple disulphide bonds, such as from 2, 3, 4, 5, 6, 7, 8 or 9 to 16, 18, 24, 27, 32, 36, 40, 45, 48, 54, 56 or 63, may form between the two pores in the double pore. One or both the first or second pore may comprise at least one monomer, such as up to 8, 9 or 10 monomers, that comprises a cysteine residue at the interface between the first and second pores at a position corresponding to R97, 1107, R110, Q100, E101, N102 and/or L113 of SEQ ID NO: 2.

At least one monomer in the first pore and/or at least one monomer in the second pore may comprise at least one residue at the interface between the first and second pores, which residue is more hydrophobic than the residue present at the corresponding position in the wild type CsgG monomer, or the wild type CsgG homologue monomer. For example, from 2 to 10, such as 3, 4, 5, 6, 7, 8 or 9, residues in the first pore and/or the second pore may be more hydrophobic that the residues at the same positions in the corresponding wild type CsgG monomer, or wild type CsgG homologue. Such hydrophobic residues strengthen the interaction between the two pores in the double pore. The at least one residue at the interface between the first and second pores may be at a position corresponding to R97, 1107, R110, Q100, E101, N102 and or L113 of SEQ ID NO: 2. Where the residue at the interface in the wild type CsgG monomer, or the wild type CsgG homologue monomer is R, Q, N or E, the hydrophobic residue is typically I, L, V, M, F, W or Y. Where the residue at the interface in the wild type CsgG monomer, or the wild type CsgG homologue monomer is I, the hydrophobic residue is typically L, V, M, F, W or Y. Where the residue at the interface in the wild type CsgG monomer, or the wild type CsgG homologue monomer is L, the hydrophobic residue is typically I, V, M, F, W or Y.

The double pore may comprise one or more monomer that comprises one or more cysteine residue at the interface between the pores and one or more monomer that comprises one or more introduced hydrophobic residue at the interface between the pores, or may comprise one or more monomer that comprises such cysteine residues and such hydrophobic residues. For example, one or more, such as any 2, 3, or 4, of the positions in the monomer corresponding to the positions at R97, I107, R110, Q100, E101, N102 and or L113 of SEQ ID NO: 2 may comprise a cysteine (C) residue and one or more, such as any 2, 3 or 4, of the positions in the monomer corresponding to the positions at R97, I107, R110, Q100, E101, N102 and or L113 of SEQ ID NO: 2 may comprise a hydrophobic residue, such as I, L, V, M, F, W or Y.

The present inventors have identified holes in the join between two wild-type CsgG pores that assemble in a tail to tail orientation to form a double pore. The inventors have recognised that any gaps present between the first and second pore may allow current, i.e. ions, to pass into or out of the pore at the junction between the first and second pore. Such passage of ions would be detrimental when the pore is used to detect or characterise an analyte. Accordingly, these holes may be closed in a double pore, i.e. the double pore typically does not include any holes at the join between the first and second pore. The channel provided by the double pore typically does not leak ions. It is a channel with continuous walls. The structure of the double pore provides a solid wall around the channel formed by the first and second pores.

The double pore according may contain bulky residues at one or more, such as 2, 3, 4, 5, 6 or 7, positions in the tail region, which residues are typically at the interface between the first and second pores and are bulkier than the residues present at the corresponding positions in the wild type CsgG monomer, or the wild type CsgG homologue monomer. The bulk of these residues prevents holes from forming in the walls of the pore at the interface between the first and second pore in the double pore. The at least one bulky residue at the interface between the first and second pores is typically at a position corresponding to A98, A99, T104, V105, L113, Q114 or S115 of SEQ ID NO: 2. Where the residue at the interface in the wild type CsgG monomer, or the wild type CsgG homologue monomer is A, the bulky residue is typically I, L, V, M, F, W, Y, N, Q, S or T. Where the residue present at the interface in the wild type CsgG monomer, or the wild type CsgG homologue monomer is T, the bulky residue is typically L, M, F, W, Y, N, Q, R, D or E. Where the residue present at the interface in the wild type CsgG monomer, or the wild type CsgG homologue monomer is V, the bulky residue is typically I, L, M, F, W, Y, N, Q. Where the residue present at the interface in the wild type CsgG monomer, or the wild type CsgG homologue monomer is L, the bulky residue is typically M, F, W, Y, N, Q, R, D or E. Where the residue present at the interface in the wild type CsgG monomer, or the wild type CsgG homologue monomer is Q, the bulky residue is typically F, W or Y. Where the residue present at the interface in the wild type CsgG monomer, or the wild type CsgG homologue monomer is S, the bulky residue is typically M, F, W, Y, N, Q, E or R.

Particularly where the second pore is located outside the membrane, the second pore, and optionally the first pore, preferably comprises residues in the barrel region of the pore that reduce the negative charge inside the barrel compared to the charge in the barrel of the wild type CsgG pore, or homologue. These mutations make the barrel more hydrophilic. At least one monomer in the first pore and/or at least one monomer in the second pore of the double pore may comprise at least one residue in the barrel region of the pore, which residue has less negative charge than the residue present at the corresponding position in the wild type CsgG monomer, or the wild type CsgG homologue monomer. The charge inside the barrel is sufficiently neutral or positive such that negatively charged analytes, such as polynucleotides, are not repelled from entering the pore by electrostatic charges. At least one residue, such as 2, 3, 4 or 5 residues, in the barrel region of the pore at a position corresponding to D149, E185, D195, E210 and/or E203 of SEQ ID NO: 2 may be a neutral or positively charged amino acid. At least one residue, such as 2, 3, 4 or 5 residues, in the barrel region of the pore at a position corresponding to D149, E185, D195, E210 and/or E203 of SEQ ID NO: 2 is preferably N, Q, R or K.

Particular examples of charge-removing mutations in SEQ ID NO: 2 or SEQ ID NO: 26 include the following: E185N/E203N; D149N/E185R/D195N/E201R/E203N, D149N/E185R/D195N/E201N/E203N, D149R/E185N/ D195N/E201N/E203N, D149R/E185N/E201N/E203N, D149N/E185N/D195/E201N/E203N, D149N/E185N/ E201N/E203N, D149N/E185N/E203N, D149N/E185N/ E201N, D149N/E203N, D149N/E201N/D195N, D149N/ E201N, D195N/E201N/E203N, E201N/E203N, D195N/ E203, E203R, E203N, E201R, E201N, D195R, D195N, E185R, E185N, D149R and D149N.

At least one monomer in the first CsgG pore, or homologue thereof, may comprise at least one residue in the constriction of the barrel region of the first pore, which residue decreases, maintains or increases the length of the constriction compared to the wild type CsgG pore, or the wild type CsgG homologue pore, and/or at least one monomer in the second CsgG pore, or homologue thereof, may comprise at least one residue in the constriction of the barrel region of the second pore, which residue decreases, maintains or increases the length of the constriction compared to the wild type CsgG pore, or the wild type CsgG homologue pore. Preferably, the length of the constriction in the first pore and/or the length of the constriction in the second pore is at least as long as in the wild-type pore and more preferably longer.

The length of the pore may be increased by inserting residues into the region corresponding to the region between positions K49 and F56 of SEQ ID NO: 2. From 1 to 5, such as 2, 3, or 4 amino acid residues may be inserted at any one or more of the following positions defined by reference to SEQ ID NO: 2: K49 and P50, P50 and Y51, Y51 and P52, P52 and A53, A53 and S54, S54 and N55 and/or N55 and F56. Preferably from 1 to 10, such as 2 to 8, or 3 to 5 amino acid residues in total are inserted into the sequence of a monomer. Preferably, all of the monomers in the first pore and/or all of the monomers in the second pore have the same number of insertions in this region. The inserted residues may increase the length of the loop between the residues corresponding to Y51 and N55 of SEQ ID NO: 2. The inserted residues may be any combination of A, S, G or T to maintain flexibility; P to add a kink to the loop; and/or S, T, N, Q, M, F, W, Y, V and/or I to contribute to the signal produced when a analyte interacts with the barrel of the pore under an applied potential difference. The inserted amino acids may be any combination of S, G, SG, SGG, SGS, GS, GSS and/or GSG.

In the double pore, the constriction in the barrel of the first pore and/or the second pore may comprise at least one residue, such as 2, 3, 4 or 5 residues, which influences the properties of the pore when used to detect or characterise an analyte compared to when a first pore or a second pore with a wild-type constriction is used, wherein the at least one residue in the constriction of the barrel region of the pore is at a position corresponding to Y51, N55, Y51, P52 and/or A53 of SEQ ID NO: 2. The at least one residue may be Q or V at a position corresponding to F56 of SEQ ID NO: 2;

A or Q at a position corresponding to Y51 of SEQ ID NO: 2; and/or V at a position corresponding to N55 of SEQ ID NO: 2.

The double pore may comprise at least one monomer in the first CsgG pore, or homologue thereof, and/or at least one monomer in the second CsgG pore, or homologue thereof, which monomer comprises two or more of the mutations defined above.

Mutant CsgG Monomers

Provided are novel mutant CsgG monomers, and monomers of CsgG homologues. The monomer may be an isolated monomer. The mutant CsgG monomers may be used to form pores and double pores. A mutant CsgG monomer is a monomer whose sequence varies from that of a wild-type CsgG monomer and which retains the ability to form a pore. A mutant monomer of a CsgG homologue is a monomer whose sequence varies from that of a wild-type CsgG monomer and which retains the ability to form a pore. Methods for confirming the ability of mutant monomers to form pores are well-known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state.

Provided is a CsgG monomer, or a monomer of a CsgG homologue, comprising a cysteine residue at a position corresponding to R97, I107, R110, Q100, E101, N102 and or L113 of SEQ ID NO: 2.

Provided is a CsgG monomer, or a monomer of a CsgG homologue, comprising a residue at a position corresponding to any one or more of R97, Q100, I107, R110, E101, N102 and L113 of SEQ ID NO: 2, which residue is more hydrophobic than the residue present at the corresponding position of SEQ ID NO: 2, or in the amino acid sequence of a wild type CsgG homologue, such as the corresponding position of any one of SEQ ID NOs: 3 to 23, wherein the residue at the position corresponding to R97 and/or I107 is M, the residue at the position corresponding to R110 is I, L, V, M, W or Y, and/or the residue at the position corresponding to E101 or N102 is V or M. The residue at a position corresponding to Q100 is typically I, L, V, M, F, W or Y; and or the residue at a position corresponding to L113 is typically I, V, M, F, W or Y.

Particular monomers may have the sequence shown in SEQ ID NO 2 or SEQ ID NO: 26 comprising Y51A, F56Q substitutions and R97I/V/L/M/F/W/Y, I107L/V/M/F/W/Y, R110I/V/L/M/F/W/Y, Q100I/V/L/M/F/W/Y, E101I/V/L/M/F/W/Y, N102I/V/L/M/F/W/Y and L113CI/V/L/M/F/W/Y in combination, R97I/V/L/M/F/W/Y and N102I/V/L/M/F/W/Y in combination and/or R97I/V/L/M/F/W/Y and E101I/V/L/M/F/W/Y in combination. I107 may already form hydrophobic interactions between two pores.

Provided is a CsgG monomer, or a monomer of a CsgG homologue, comprising a residue at a position corresponding to any one or more of A98, A99, T104, V105, L113, Q114 and S115 of SEQ ID NO: 2 which is bulkier than the residue present at the corresponding position of SEQ ID NO: 2, or in the amino acid sequence of a wild type CsgG homologue, such as the corresponding position of any one of SEQ ID NOs: 3 to 23, wherein the residue at the position corresponding to T104 is L, M, F, W, Y, N, Q, D or E, the residue at the position corresponding to L113 is M, F, W, Y, N, G, D or E and/or the residue at the position corresponding to S115 is M, F, W, Y, N, Q or E. The residue at a position corresponding to A98 or A99, is typically I, L, V, M, F, W, Y, N, Q, S or T. The residue at a position corresponding to V105 is I, L, M, F, W, Y, N or Q. The residue at a position corresponding to Q114 is F, W or Y. The residue at a position corresponding to E210 is N, Q, R or K.

Particular monomers may have the sequence shown in SEQ ID NO 2 or SEQ ID NO: 26 comprising Y51A, F56Q substitutions and 1, 2, 3, 4, 5, 6 or all of the following substitutions: A98I/L/V/M/F/W/Y/N/Q/S/T; A99I/L/V/M/F/W/Y/N/Q/S/T; T104N/Q/L/R/D/E/M/F/W/Y; V105I/L/M/F/W/Y/N/Q; L113M/F/W/Y/N/Q/D/E/L/R; Q114Y/F/W; and S115N/Q/M/F/W/Y/E/R.

Provided is a CsgG monomer, or a monomer of a CsgG homologue, comprising a residue in the barrel region of the pore at a position corresponding to any one ore more of D149, E185, D195, E210 and E203 less negative charge than the residue present at the corresponding position of SEQ ID NO: 2, or in the amino acid sequence of a wild type CsgG homologue, such as the corresponding position of any one of SEQ ID NOs: 3 to 23, wherein the residue at the position corresponding to D149, E185, D195 and/or E203 is K.

Provided is a CsgG monomer, or a monomer of a CsgG homologue, wherein at least one monomer in the first CsgG pore, or homologue thereof, and/or at least one monomer in the second CsgG pore, or homologue thereof, comprises at least one residue in the constriction of the barrel region of the pore, which residue increases the length of the constriction compared to the wild type CsgG pore, or the wild type CsgG homologue pore. The at least one residue is additional to the residues present in the constriction of the wild type CsgG pore, or the wild type CsgG homologue pore.

The length of the pore may be increased by inserting residues into the region corresponding to the region between positions K49 and F56 of SEQ ID NO: 2. From 1 to 5, such as 2, 3, or 4 amino acid residues may be inserted at any one or more of the following positions defined by reference to SEQ ID NO: 2: K49 and P50, P50 and Y51, Y51 and P52, P52 and A53, A53 and S54, S54 and N55 and/or N55 and F56. Preferably from 1 to 10, such as 2 to 8, or 3 to 5 amino acid residues in total are inserted into the sequence of the monomer. The inserted residues may increase the length of the loop between the residues corresponding to Y51 and N55 of SEQ ID NO: 2. The inserted residues may be any combination of A, S, G or T to maintain flexibility; P to add a kink to the loop; and/or S, T, N, Q, M, F, W, Y, V and/or I to contribute to the signal produced when a analyte interacts with the barrel of the pore under an applied potential difference. The inserted amino acids may be any combination of S, G, SG, SGG, SGS, GS, GSS and/or GSG.

Provided is a CsgG monomer, or a monomer of a CsgG homologue, comprising at least one residue in the constriction of the barrel region of the pore at a position corresponding to N55, P52 and/or A53 of SEQ ID NO: 2 that is different from the residue present in the corresponding wild type monomer, wherein the residue at a position corresponding to N55 is V.

Any two or more of the above described residues may be present in the same monomer. In particular the monomer may comprise at least one said cysteine residue, at least one said hydrophobic residue, at least one said bulky residue, at least one said neutral or positively charged residue and/or at least one said residue that increases the length of the constriction.

The monomer may additionally comprise one or more, such as 2, 3, 4 or 5 residues, which influence the properties of the pore when used to detect or characterise an analyte compared to when a first pore or a second pore with a wild-type constriction is used, wherein the at least one residue in the constriction of the barrel region of the pore is at a position corresponding to Y51, N55, Y51, P52 and/or A53 of SEQ ID NO: 2. The at least one residue may be Q or V at a position corresponding to F56 of SEQ ID NO: 2; A or Q at a position corresponding to Y51 of SEQ ID NO: 2; and/or V at a position corresponding to N55 of SEQ ID NO: 2.

Methods for introducing or substituting naturally-occurring amino acids are well known in the art. For instance, methionine (M) may be substituted with arginine (R) by replacing the codon for methionine (ATG) with a codon for arginine (CGT) at the relevant position in a polynucleotide encoding the mutant monomer. The polynucleotide can then be expressed as discussed below.

Methods for introducing or substituting non-naturally-occurring amino acids are also well known in the art. For instance, non-naturally-occurring amino acids may be introduced by including synthetic aminoacyl-tRNAs in the IVTT system used to express the mutant monomer. Alternatively, they may be introduced by expressing the mutant monomer in *E. coli* that are auxotrophic for specific amino acids in the presence of synthetic (i.e. non-naturally-occurring) analogues of those specific amino acids. They may also be produced by naked ligation if the mutant monomer is produced using partial peptide synthesis.

Variants

In addition to the specific residues discussed above, the monomer may include other mutations of the wild type sequence.

The monomers, and at least one of the monomers in the pores and double pores, may comprise aspartic acid (D), glutamine (Q), phenylalanine (F), serine (S) or threonine (T) at a position corresponding to arginine (R) 192 of SEQ ID NO: 2. Such monomers, and in particular a monomer comprising a D at this position, are much easier to express than monomers comprising a R at a position corresponding to 192 of SEQ ID NO: 2.

The monomers, and at least one of the monomers in the pores and double pores, may comprise aspartic acid (N), glutamine (Q), arginine (R), phenylalanine (F), tyrosine (Y), tryptophan (W), leucine (L) or serine (S) in which the lysine (K) at a position corresponding to lysine (K) 192 of SEQ ID NO: 2. Such monomers, and in particular a monomer comprising a Q or N at this position, are less noisy than otherwise identical monomers that comprise a K at a position corresponding to 94 of SEQ ID NO: 2.

The monomers, and at least one of the monomers in the pores and double pores, may comprise cis and/or trans loop mutations. Such mutations may play a vital role in double pores, such as in facilitating pore-pore interactions (cis side) and/or pore-enzyme interactions (trans side).

The monomers, and at least one of the monomers in the pores and double pores, may comprise one or more of the following amino acid residues, wherein the position of the amino acid residue is defined by reference to SEQ ID NO: 2: D43S (a serine residue at the position corresponding to D43 of SEQ ID NO: 2), E44S (a serine residue at the position corresponding to E44 of SEQ ID NO: 2), F48S/N/Q/Y/W/I/V/H/R/K (a S, N, Q, Y, W, I, V, H, R or K residue at the position corresponding to F48 of SEQ ID NO: 2), Q87N/R/K (a N, R or K residue at the position corresponding to Q87 of SEQ ID NO: 2), N91K/R (a K or R residue at the position corresponding to N91 of SEQ ID NO: 2), K94N/Q/R/F/Y/W/L/S/N (a N, Q, R, F, Y, W, L, S or N residue at the position corresponding to K94 of SEQ ID NO: 2), R97F/Y/W/V/I/K/S/Q/H (a F. Y, W, V, I, K, S, Q or H residue at the position corresponding to R97 of SEQ ID NO: 2), E101I/L/A/H (a L, A or H residue at the position corresponding to E101 of SEQ ID NO: 2), N102K/Q/L/I/V/S/H, R110F/G/N (a K, Q, L, I, V, S or H residue at the position corresponding to N102 of SEQ ID NO: 2), Q114R/K (a R or K residue at the position corresponding to Q114 of SEQ ID NO: 2), R142Q/S (a Q or S residue at the position corresponding to R142 of SEQ ID NO: 2), T150Y/A/V/L/S/Q/N (a Y, A, V, L, S, Q or N residue at the position corresponding to T150 of SEQ ID NO: 2), R192D/Q/F/S/T (a D, Q, F, S or T residue at the position corresponding to R192 of SEQ ID NO: 2) and/or D248S/N/Q/K/R (a S, N, Q, K or R residue at the position corresponding to D248 of SEQ ID NO: 2).

The monomers, and at least one of the monomers in the pores and double pores, may comprise one or more of the following deletions, wherein the position of the deletion is defined by reference to SEQ ID NO: 2: one or more of the residues at positions corresponding to R192, F193, I194, D195, Y196, Q197, R198, L199, L200 and E201 of SEQ ID NO: 2 and/or deletion of one or more of the residues corresponding to V139, G140, D149, T150, V186, Q187, V204 and/or G205 of SEQ ID NO: 2, G137, G138, Q151, Y152, Y184, E185, Y206 and/or T207 of SEQ ID NO: 2 and/or A141, R142, G147, A148, A188, G189, G202 and/or E203 of SEQ ID NO: 2.

The monomers, and at least one of the monomers in the pores and double pores, may comprise:

a W residue at the position corresponding to R97 of SEQ ID NO: 2;

a D, Q, F, S or T residue at the position corresponding to R192 of SEQ ID NO: 2;

a Y residue at the position corresponding to R97 of SEQ ID NO: 2 and/or a W or Y residue at the position corresponding to R93 of SEQ ID NO: 2;

a Q or N residue at the position corresponding to K94 of SEQ ID NO: 2;

a K or R residue at the position corresponding to G103 and/or T104 of SEQ ID NO: 2; and/or a T residue at the position corresponding to F191 of SEQ ID NO: 2, deletion of the residues corresponding to V105, A106 and I107 of SEQ ID NO: 2 and/or deletion of the residues corresponding to F193, I194, D195, Y196, Q197, R198 and L199 of SEQ ID NO: 2.

The monomers, and at least one of the monomers in the pores and double pores, may comprise an A at the position corresponding to Y51 of SEQ ID NO: 2 and/or a Q at the position corresponding to F56Q of SEQ ID NO: 2.

The monomers, and at least one of the monomers in the pores and double pores, may comprise mutations corresponding to the following mutations in SEQ ID NO: 2:

(1) Y51A, F56Q and R192D;

(2) Y51A, F56Q and R97W.

(3) Y51A, F56Q, R192D and R97W;

(4) Y51A, F56Q, R192D and R93W;

(5) Y51A, F56Q, R192D, R93Y and R97Y; or (6) Y51A, F56Q, R192D and R93W.

(7) the mutations of any one of (1)-(6) and:

(a) deletion of V105, A106 and I107.

(b) K94Q or K94N;

(c) deletion of D195, Y196, Q197, R198 and L199 or deletion of F193, I194, D195, Y196, Q197, R198 and L199; and/or (d)F191T.

(8) the mutations of any one of (1)-(6) and:

(i) K94Q and deletion of V105, A106 and I107;

(ii) K94N and deletion of V105, A106 and I107;

(iii) F191T and deletion of V105, A106 and I107;

(iv) K94Q and F191T;

(v) K94N and F191T;

(vi) K94Q, F191T and deletion of V105, A106 and I107; or (vii) K94N, F191T and deletion of V105, A106 and I107.

(9) the mutations of any one of (1)-(8) and:

T104K or T104R;

L90R;

N91R;

I95R;

A99R;

E101K, E101N, E101Q, E101T or E101H;

E44N or E44Q; and/or

Q42K.

The monomer may be a variant of any one of SEQ ID NOs: 2 to 23, preferably of SEQ ID NO: 2. Over the entire length of the amino acid sequence of any one of SEQ ID NOs: 2 to 23, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NO: 2 to 23 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/).

SEQ ID NO: 2 is the amino acid sequence of the wild-type CsgG monomer from *Escherichia coli* Str. K-12 substr. MC4100. At least one of the monomers comprised in the pores or double pores may comprise the amino acid sequence shown in SEQ ID NO: 2. At least one of the monomers comprised in the pores or double pores may comprise the amino acid sequence shown in any one of SEQ ID NOs: 3 to 23.

The monomers, and at least one of the monomers comprised in the pores or double pores may comprise an amino acid sequence that is a variant of the amino acid sequence shown in SEQ ID NO: 2. The variant of SEQ ID NO: 2 may comprise any of the substitutions present in another CsgG homologue. Preferred CsgG homologues are shown in SEQ ID NOs: 3 to 23. The variant may comprise combinations of one or more of the substitutions present in SEQ ID NOs: 3 to 23 compared with SEQ ID NO: 2. For example, mutations may be made at any one or more of the positions in SEQ ID NO: 2 that differ between SEQ ID NO: 2 and any one of SEQ ID NOs: 3 to 23. Such a mutation may be a substitution of an amino acid in SEQ ID NO: 2 with an amino acid from the corresponding position in any one of SEQ ID NOs: 3 to 23. Alternatively, the mutation at any one of these positions may be a substitution with any amino acid, or may be a deletion or insertion mutation, such as deletion or insertion of 1 to 10 amino acids, such as of 2 to 8 or 3 to 6 amino acids. Other than the mutations disclosed herein, the amino acids that are conserved between SEQ ID NO: 2 and all of SEQ ID NOs: 3 to 23 are preferably present in a variant. However, conservative mutations may be made at any one or more of these positions that are conserved between SEQ ID NO: 2 and all of SEQ ID NOs: 3 to 23.

Provided is a pore-forming CsgG mutant monomer, or monomer of a CsgG homologue, that comprises any one or more of the amino acids described herein as being substituted into a specific position of SEQ ID NO: 2 at a position in the structure of the monomer that corresponds to the specific position in SEQ ID NO: 2. Corresponding positions may be determined by standard techniques in the art. For example, the PILEUP and BLAST algorithms mentioned above can be used to align the sequence of a CsgG monomer, or monomer of a CsgG homologue, with SEQ ID NO: 2 and hence to identify corresponding residues.

In particular, a pore-forming CsgG mutant monomer that comprises any one or more of the following is provided:

a W at a position corresponding to R97 in SEQ ID NO:2;

a W at a position corresponding to R93 in SEQ ID NO:2;

a Y at a position corresponding to R97 in SEQ ID NO: 2;

a Y at a position corresponding to R93 in SEQ ID NO: 2;

a Y at each of the positions corresponding to R93 and R97 in SEQ ID NO: 2;

a D at the position corresponding to R192 in SEQ ID NO:2;

deletion of the residues at the positions corresponding to V105-I107 in SEQ ID NO:2;

deletion of the residues at one or more of the positions corresponding to F193 to L199 in SEQ ID NO: 2;

deletion of the residues the positions corresponding to F195 to L199 in SEQ ID NO: 2;

deletion of the residues the positions corresponding to F193 to L199 in SEQ ID NO: 2;

a T at the position corresponding to F191 in SEQ ID NO: 2;

a Q at the position corresponding to K49 in SEQ ID NO: 2;

a N at the position corresponding to K49 in SEQ ID NO: 2;

a Q at the position corresponding to K42 in SEQ ID NO: 2;

a Q at the position corresponding to E44 in SEQ ID NO: 2;

a N at the position corresponding to E44 in SEQ ID NO: 2;

a R at the position corresponding to L90 in SEQ ID NO: 2;

a R at the position corresponding to L91 in SEQ ID NO: 2;

a R at the position corresponding to I95 in SEQ ID NO: 2;

a R at the position corresponding to A99 in SEQ ID NO: 2;

a H at the position corresponding to E101 in SEQ ID NO: 2;

a K at the position corresponding to E101 in SEQ ID NO: 2;

a N at the position corresponding to E101 in SEQ ID NO: 2;

a Q at the position corresponding to E101 in SEQ ID NO: 2;

a T at the position corresponding to E101 in SEQ ID NO: 2;

a K at the position corresponding to Q114 in SEQ ID NO: 2.

The CsgG pore-forming monomer may further comprise an A at the position corresponding to Y51 in SEQ ID NO: 2 and/or a Q at the position corresponding to F56 in SEQ ID NO: 2.

The pore-forming mutant monomer typically retains the ability to form the same 3D structure as the wild-type CsgG monomer, such as the same 3D structure as a CsgG monomer having the sequence of SEQ ID NO: 2. The 3D structure of CsgG is known in the art and is disclosed, for example, in Cao et al (2014) PNAS E5439-E5444. Any number of mutations may be made in the wild-type CsgG sequence in addition to the mutations described herein provided that the CsgG mutant monomer retains the improved properties imparted on it by the mutations.

Typically the CsgG monomer will retain the ability to form a structure comprising three alpha-helicies and five beta-sheets. The present inventors have shown in particular that mutations may be made at least in the region of CsgG which is N-terminal to the first alpha helix (which starts at S63 in SEQ ID NO:2), in the second alpha helix (from G85 to A99 of SEQ ID NO: 2), in the loop between the second alpha helix and the first beta sheet (from Q100 to N120 of SEQ ID NO: 2), in the fourth and fifth beta sheets (S173 to R192 and R198 to T107 of SEQ ID NO: 2, respectively) and in the loop between the fourth and fifth beta sheets (F193 to Q197 of SEQ ID NO: 2) without affecting the ability of the CsgG monomer to form a transmembrane pore, which transmembrane pore is capable of translocating polypeptides. Therefore, it is envisaged that further mutations may be made in any of these regions in any CsgG monomer without affecting the ability of the monomer to form a pore that can translocate polynucleotides. It is also expected that mutations may be made in other regions, such as in any of the alpha helicies (S63 to R76, G85 to A99 or V211 to L236 of SEQ ID NO: 2) or in any of the beta sheets (I121 to N133, K135 to R142, I146 to R162, S173 to R192 or R198 to T107 of SEQ ID NO: 2) without affecting the ability of the monomer to form a pore that can translocate polynucleotides. It is also expected that deletions of one or more amino acids can be made in any of the loop regions linking the alpha helicies and beta sheets and/or in the N-terminal and/or C-terminal regions of the CsgG monomer without affecting the ability of the monomer to form a pore that can translocate polynucleotides.

Amino acid substitutions may be made to the amino acid sequence of SEQ ID NO: 2 in addition to those discussed herein, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

| Hydropathy scale | |
|---|---|
| Side Chain | Hydropathy |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 or more residues may be deleted.

The monomers may be fragments of SEQ ID NO: 2, and pores and the double pores may comprise fragments of SEQ ID NO:2 or of a homologue of SEQ ID NO: 2. Such fragments retain pore forming activity. Fragments may be at least 50, at least 100, at least 150, at least 200 or at least 250 amino acids in length. Such fragments may be used to produce the pores. A fragment preferably comprises the membrane spanning domain corresponding to K135-Q153 and S183-S208 of SEQ ID NO: 2.

One or more amino acids may be alternatively or additionally added to the polypeptides described above. An extension may be provided at the amino terminal or carboxy terminal of the amino acid sequence of SEQ ID NO: 2 or variant or fragment thereof. The extension may be quite short, for example from 1 to 10 amino acids in length. Alternatively, the extension may be longer, for example up to 50 or 100 amino acids. A carrier protein may be fused to an amino acid sequence. Other fusion proteins are discussed in more detail below.

A variant of SEQ ID NO: 2 is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of CsgG, which contains a β-barrel, is provided by β-sheets in each subunit. A variant of SEQ ID NO: 2 typically comprises the regions in SEQ ID NO: 2 that form β-sheets, namely K135-Q153 and S183-S208. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its □-helices and/or loop regions.

The monomers derived from CsgG may be modified to assist their identification or purification, for example by the addition of a streptavidin tag or by the addition of a signal sequence to promote their secretion from a cell where the monomer does not naturally contain such a sequence. Other suitable tags are discussed in more detail below. The monomer may be labelled with a revealing label. The revealing label may be any suitable label which allows the monomer to be detected. Suitable labels are described below.

The monomer derived from CsgG may also be produced using D-amino acids. For instance, the monomer derived from CsgG may comprise a mixture of L-amino acids and D-amino acids. This is conventional in the art for producing such proteins or peptides.

The monomer derived from CsgG contains one or more specific modifications to facilitate nucleotide discrimination. The monomer derived from CsgG may also contain other non-specific modifications as long as they do not interfere with pore formation. A number of non-specific side chain modifications are known in the art and may be made to the side chains of the monomer derived from CsgG. Such modifications include, for example, reductive alkylation of amino acids by reaction with an aldehyde followed by reduction with $NaBH_4$, amidination with methylacetimidate or acylation with acetic anhydride.

The monomer derived from CsgG can be produced using standard methods known in the art. The monomer derived from CsgG may be made synthetically or by recombinant means. For example, the monomer may be synthesised by in vitro translation and transcription (IVTT). Suitable methods for producing pores and monomers are discussed in WO 2010/004273, WO 2010/004265 and WO 2010/086603. Methods for inserting pores into membranes are also discussed.

In some embodiments, the monomer, which may optionally be comprised in a pore or double pore is chemically modified. The mutant monomer can be chemically modified in any way and at any site. The monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The mutant monomer may be chemically modified by the attachment of any molecule. For instance, the mutant monomer may be chemically modified by attachment of a dye or a fluorophore.

In some embodiments, the monomer is chemically modified with a molecular adaptor that facilitates the interaction between a pore comprising the monomer and a target nucleotide or target polynucleotide sequence. The presence of the adaptor improves the host-guest chemistry of the pore and the nucleotide or polynucleotide sequence and thereby improves the sequencing ability of pores formed from the monomer. The principles of host-guest chemistry are well-known in the art. The adaptor has an effect on the physical or chemical properties of the pore that improves its interaction with the nucleotide or polynucleotide sequence. The adaptor may alter the charge of the barrel or channel of the pore or specifically interact with or bind to the nucleotide or polynucleotide sequence thereby facilitating its interaction with the pore.

The molecular adaptor is preferably a cyclic molecule, a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor preferably has eight-fold or nine-fold symmetry since CsgG typically has eight or nine subunits around a central axis. This is discussed in more detail below.

The adaptor typically interacts with the nucleotide or polynucleotide sequence via host-guest chemistry. The adaptor is typically capable of interacting with the nucleotide or polynucleotide sequence. The adaptor comprises one or more chemical groups that are capable of interacting with the nucleotide or polynucleotide sequence. The one or more chemical groups preferably interact with the nucleotide or polynucleotide sequence by non-covalent interactions, such as hydrophobic interactions, hydrogen bonding, Van der Waal's forces, xT-cation interactions and/or electrostatic forces. The one or more chemical groups that are capable of interacting with the nucleotide or polynucleotide sequence are preferably positively charged. The one or more chemical groups that are capable of interacting with the nucleotide or polynucleotide sequence more preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of eight amino groups. A ring of protonated amino groups may interact with negatively charged phosphate groups in the nucleotide or polynucleotide sequence.

The correct positioning of the adaptor within the pore can be facilitated by host-guest chemistry between the adaptor and the pore comprising the mutant monomer. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, xT-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide sequence can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, H-J. (1994) *J. Am. Chem. Soc.* 116, 6081-6088. The adaptor is more preferably heptakis-6-amino-β-cyclodextrin (am$_7$-βCD), 6-monodeoxy-β-monoamino-β-cyclodextrin (am$_1$-□CD) or heptakis-(6-deoxy-6-guanidino)-cyclodextrin (gu$_7$-βCD). The guanidino group in gu$_7$-βCD has a much higher pKa than the primary amines in am$_7$-βCD and so it is more positively charged. This gu$_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanoyl-β-cyclodextrin (am$_6$amPDP$_1$-βCD).

More suitable adaptors include γ-cyclodextrins, which comprise 9 sugar units (and therefore have nine-fold symmetry). The γ-cyclodextrin may contain a linker molecule or may be modified to comprise all or more of the modified sugar units used in the β-cyclodextrin examples discussed above.

The molecular adaptor is preferably covalently attached to the monomer. The adaptor can be covalently attached to the pore using any method known in the art. The adaptor is typically attached via chemical linkage. If the molecular adaptor is attached via cysteine linkage, the one or more cysteines have preferably been introduced to the mutant, for instance in the barrel, by substitution. The monomer may be chemically modified by attachment of a molecular adaptor to one or more cysteines in the monomer. The one or more cysteines may be naturally-occurring, i.e. at positions 1 and/or 215 in SEQ ID NO: 2. Alternatively, the mutant monomer may be chemically modified by attachment of a molecule to one or more cysteines introduced at other positions. The cysteine at position 215 may be removed, for instance by substitution, to ensure that the molecular adaptor does not attach to that position rather than the cysteine at position 1 or a cysteine introduced at another position.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the monomer before a linker is attached. The molecule may be attached directly to the monomer. The molecule is preferably attached to the monomer using a linker, such as a chemical crosslinker or a peptide linker.

Suitable chemical crosslinkers are well-known in the art. Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate. The most preferred crosslinker is succinimidyl 3-(2-pyridyldithio)propionate (SPDP). Typically, the molecule is covalently attached to the bifunctional crosslinker before the molecule/crosslinker complex is covalently attached to the monomer but it is also possible to covalently attach the bifunctional crosslinker to the monomer before the bifunctional crosslinker/monomer complex is attached to the molecule.

The linker is preferably resistant to dithiothreitol (DTT). Suitable linkers include, but are not limited to, iodoacetamide-based and Maleimide-based linkers.

In other embodiment, the monomer may be attached to a polynucleotide binding protein. This forms a modular sequencing system that may be used in methods of sequencing. Polynucleotide binding proteins are discussed below.

The polynucleotide binding protein is preferably covalently attached to the monomer. The protein can be covalently attached to the monomer using any method known in the art. The monomer and protein may be chemically fused or genetically fused. The monomer and protein are genetically fused if the whole construct is expressed from a single polynucleotide sequence. Genetic fusion of a monomer to a polynucleotide binding protein is discussed in WO 2010/004265.

If the polynucleotide binding protein is attached via cysteine linkage, the one or more cysteines have preferably been introduced to the mutant by substitution. The one or more cysteines are preferably introduced into loop regions which have low conservation amongst homologues indicating that mutations or insertions may be tolerated. They are therefore suitable for attaching a polynucleotide binding protein. In such embodiments, the naturally-occurring cysteine at position 251 may be removed. The reactivity of cysteine residues may be enhanced by modification as described above.

The polynucleotide binding protein may be attached directly to the monomer or via one or more linkers. The molecule may be attached to the monomer using the hybridization linkers described in WO 2010/086602. Alternatively, peptide linkers may be used. Peptide linkers are amino acid sequences. The length, flexibility and hydrophilicity of the peptide linker are typically designed such that it does not disturb the functions of the monomer and molecule. Preferred flexible peptide linkers are stretches of 2 to 20, such as 4, 6, 8, 10 or 16, serine and/or glycine amino acids. More preferred flexible linkers include (SG)$_1$, (SG)$_2$, (SG)$_3$, (SG)$_4$, (SG)$_5$ and (SG)$_8$ wherein S is serine and G is glycine. Preferred rigid linkers are stretches of 2 to 30, such as 4, 6, 8, 16 or 24, proline amino acids. More preferred rigid linkers include (P)$_{12}$ wherein P is proline.

The monomer may be chemically modified with a molecular adaptor and a polynucleotide binding protein.

The molecule (with which the monomer is chemically modified) may be attached directly to the monomer or attached via a linker as disclosed in WO 2010/004273, WO 2010/004265 or WO 2010/086603.

Any of the proteins described herein, such as the monomers and pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the protein. An example of this would be to react a gel-shift reagent to a cysteine engineered on the outside of the protein. This has been demonstrated as a method for separating hemolysin hetero-oligomers (Chem Biol. 1997 July; 4(7):497-505).

Any of the proteins described herein, such as the monomers and pores, may be labelled with a revealing label. The revealing label may be any suitable label which allows the protein to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the monomers or pores, may be made synthetically or by recombinant means. For example, the protein may be synthesised by in vitro translation and transcription (IVTT). The amino acid sequence of the protein may be modified to include non-naturally occurring amino acids or to increase the stability of the protein. When a protein is produced by synthetic means, such amino acids may be introduced during production. The protein may also be altered following either synthetic or recombinant production.

Proteins may also be produced using D-amino acids. For instance, the protein may comprise a mixture of L-amino acids and D-amino acids. This is conventional in the art for producing such proteins or peptides.

The protein may also contain other non-specific modifications as long as they do not interfere with the function of the protein. A number of non-specific side chain modifications are known in the art and may be made to the side chains of the protein(s). Such modifications include, for example, reductive alkylation of amino acids by reaction with an aldehyde followed by reduction with NaBH$_4$, amidination with methylacetimidate or acylation with acetic anhydride.

Any of the proteins described herein, including the monomers and pores, can be produced using standard methods known in the art. Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, NY.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Constructs

Also provided is a construct comprising two or more covalently attached CsgG monomers, or monomer of CsgG homologues, wherein at least one of the monomers is a modified monomer, such as a monomer of the invention. The construct retains its ability to form a pore. This may be determined as discussed above. One or more constructs may be used to form pores for characterising, such as sequencing, polynucleotides. The construct may comprise at least 2, at least 3, at least 4, at least 5, at least 6, at least 7, at least 8, at least 9 or at least 10 monomers. The construct preferably comprises two monomers. The two or more monomers may be the same or different.

At least one monomer in the construct is a modified monomer, such as a monomer of the invention. Two or more, 3 or more, 4 or more, 5 or more, 6 or more, 7 or more, 8 or more, 9 or more or 10 or more monomers in the construct may be monomers of the invention. All of the monomers in the construct are preferably monomers of the invention. The monomers may be the same or different. In a preferred embodiment, the construct comprises two monomers of the invention.

The monomers in the construct are preferably approximately the same length or are the same length. The barrels of the monomers in the construct are preferably approximately the same length or are the same length. Length may be measured in number of amino acids and/or units of length.

The construct may comprise one or more monomers which are not monomers of the invention. CsgG monomers which are non mutant monomers of the invention include monomers comprising any one of SEQ ID NOs: 2 to 23 or a variant of any one of SEQ ID NOs: 2 to 23 in which none of the amino acids/positions discussed above have been mutated. At least one monomer in the construct may comprise SEQ ID NO: 2, 3, 4, 5, 6, 7, 8, 9, 10, 11, 12, 13, 14, 15, 16, 17, 18, 19, 20, 21, 22 or 23 or a variant of the sequence shown in SEQ ID NO: 2, 3, 4, 5, 6, 7, 8, 9, 10, 11, 12, 13, 14, 15, 16, 17, 18, 19, 20, 21, 22 or 23. A variant of SEQ ID NO: 2, 3, 4, 5, 6, 7, 8, 9, 10, 11, 12, 13, 14, 15, 16, 17, 18, 19, 20, 21, 22 or 23 is at least 50% homologous to SEQ ID NO: 2, 3, 4, 5, 6, 7, 8, 9, 10, 11, 12, 13, 14, 15, 16, 17, 18, 19, 20, 21, 22 or 23 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2, 3, 4, 5, 6, 7, 8, 9, 10, 11, 12, 13, 14, 15, 16, 17, 18, 19, 20, 21, 22 or 23 over the entire sequence.

The monomers in the construct are preferably genetically fused. Monomers are genetically fused if the whole construct is expressed from a single polynucleotide sequence. The coding sequences of the monomers may be combined in any way to form a single polynucleotide sequence encoding the construct.

The monomers may be genetically fused in any configuration. The monomers may be fused via their terminal amino acids. For instance, the amino terminus of the one monomer may be fused to the carboxy terminus of another monomer. The second and subsequent monomers in the construct (in the amino to carboxy direction) may comprise a methionine at their amino terminal ends (each of which is fused to the carboxy terminus of the previous monomer). For instance, if M is a monomer (without an amino terminal methionine) and mM is a monomer with an amino terminal methionine, the construct may comprise the sequence M-mM, M-mM-mM or M-mM-mM-mM. The presences of these methionines typically results from the expression of the start codons (i.e. ATGs) at the 5' end of the polynucleotides encoding the second or subsequent monomers within the polynucleotide encoding entire construct. The first monomer in the construct (in the amino to carboxy direction) may also comprise a methionine (e.g. mM-mM, mM-mM-mM or mM-mM-mM-mM).

The two or more monomers may be genetically fused directly together. The monomers are preferably genetically fused using a linker. The linker may be designed to constrain the mobility of the monomers. Preferred linkers are amino acid sequences (i.e. peptide linkers). Any of the peptide linkers discussed above may be used.

In another preferred embodiment, the monomers are chemically fused. Two monomers are chemically fused if the two parts are chemically attached, for instance via a chemical crosslinker. Any of the chemical crosslinkers discussed above may be used. The linker may be attached to one or more cysteine residues introduced into a mutant monomer. Alternatively, the linker may be attached to a terminus of one of the monomers in the construct.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described in WO 2010/086602.

Polynucleotides

Also provided are polynucleotide sequences which encode a modified monomer, such as a monomer of the invention. The polynucleotide sequence preferably comprises a sequence at least 50%, 60%, 70%, 80%, 90% or 95% homologous based on nucleotide identity to the sequence of SEQ ID NO: 1 over the entire sequence. There may be at least 80%, for example at least 85%, 90% or 95% nucleotide identity over a stretch of 300 or more, for example 375, 450, 525 or 600 or more, contiguous nucleotides ("hard homology"). Homology may be calculated as described above. The polynucleotide sequence may comprise a sequence that differs from SEQ ID NO: 1 on the basis of the degeneracy of the genetic code.

Also provided are polynucleotide sequences which encode any of the genetically fused constructs. The polynucleotide preferably comprises two or more variants of the sequence shown in SEQ ID NO: 1. The polynucleotide sequence preferably comprises two or more sequences having at least 50%, 60%, 70%, 80%, 90% or 95% homology to SEQ ID NO: 1 based on nucleotide identity over the entire sequence. There may be at least 80%, for example at least 85%, 90% or 95% nucleotide identity over a stretch of 600 or more, for example 750, 900, 1050 or 1200 or more, contiguous nucleotides ("hard homology"). Homology may be calculated as described above.

Polynucleotide sequences may be derived and replicated using standard methods in the art. Chromosomal DNA encoding wild-type CsgG may be extracted from a pore producing organism, such as *Escherichia coli*. The gene encoding the pore subunit may be amplified using PCR involving specific primers. The amplified sequence may then undergo site-directed mutagenesis. Suitable methods of site-directed mutagenesis are known in the art and include, for example, combine chain reaction. Polynucleotides encoding a construct can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, NY.

The resulting polynucleotide sequence may then be incorporated into a recombinant replicable vector such as a cloning vector. The vector may be used to replicate the polynucleotide in a compatible host cell. Thus polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane. Alternatively, the recombinant pore produced in this manner may be removed from the host cell and inserted into another membrane. When producing pores comprising at least two different monomers or constructs, the different monomers or constructs may be expressed separately in different host cells as described above, removed from the host cells and assembled into a pore in a separate membrane, such as a rabbit cell membrane or a synthetic membrane.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\gamma_L$ promoter is typically used.

The host cell typically expresses the monomer or construct at a high level. Host cells transformed with a polynucleotide sequence will be chosen to be compatible with the expression vector used to transform the cell. The host cell is typically bacterial and preferably *Escherichia coli*. Any cell with a k DE3 lysogen, for example C41 (DE3), BL21 (DE3), JM109 (DE3), B834 (DE3), TUNER, Origami and Origami B, can express a vector comprising the T7 promoter. In addition to the conditions listed above any of the methods cited in Cao et al, 2014, PNAS, Structure of the nonameric bacterial amyloid secretion channel, doi-1411942111 and Goyal et al, 2014, Nature, 516, 250-253 structural and mechanistic insights into the bacterial amyloid secretion channel CsgG may be used to express the CsgG proteins.

The invention also comprises a method of producing a mutant monomer of the invention or a construct of the invention. The method comprises expressing a polynucleotide of the invention in a suitable host cell. The polynucleotide is preferably part of a vector and is preferably operably linked to a promoter.

Pores

The invention also provides various pores in addition to the double pores described above. The pores are ideal for characterising, such as sequencing, polynucleotide sequences because they can discriminate between different nucleotides with a high degree of sensitivity. The pores can surprisingly distinguish between the four nucleotides in DNA and RNA. The pores can even distinguish between methylated and unmethylated nucleotides. The base resolution of the pores is surprisingly high. The pores show almost complete separation of all four DNA nucleotides. The pores further discriminate between deoxycytidine monophosphate (dCMP) and methyl-dCMP based on the dwell time in the pore and the current flowing through the pore.

Provided is a pore comprising at least one monomer according to the invention or a construct according to the invention. The pore may be homooligomeric or heterooligomeric.

The pores can also discriminate between different nucleotides under a range of conditions. In particular, the pores will discriminate between nucleotides under conditions that are favourable to the characterising, such as sequencing, of nucleic acids. The extent to which the pores can discriminate between different nucleotides can be controlled by altering the applied potential, the salt concentration, the buffer, the temperature and the presence of additives, such as urea, betaine and DTT. This allows the function of the pores to be fine-tuned, particularly when sequencing. This is discussed in more detail below. The pores may also be used to identify polynucleotide polymers from the interaction with one or more monomers rather than on a nucleotide by nucleotide basis.

The pore may be isolated, substantially isolated, purified or substantially purified. A pore is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as triblock copolymers, lipids or other pores. Alternatively, the pore may be present in a membrane.

The pore may be present as an individual or single pore. Alternatively, the pore may be present in a homologous or heterologous population of two or more pores.

The use of the term pore in the present disclosure is intended to encompass both pores and double pores.

Homo-Oligomeric Pores

Also provided is a homo-oligomeric pore comprising identical monomers as disclosed herein. The homo-oligomeric pore may comprise any of the monomers of the invention. The homo-oligomeric pore is ideal for characterising, such as sequencing, polynucleotides.

The homo-oligomeric pore may contain any number of monomers. The pore typically comprises at least 7, at least 8, at least 9 or at least 10 identical mutant monomers, such as 7, 8, 9 or 10 mutant monomers. The pore preferably comprises eight or nine identical monomers. One or more, such as 2, 3, 4, 5, 6, 7, 8, 9 or 10, of the monomers may be chemically modified as discussed above.

Provided are homo-oligomeric double pores.

Hetero-Oligomeric Pores

Also provided is a hetero-oligomeric pore comprising at least one monomer as disclosed herein. The hetero-oligomeric pore of the invention is ideal for characterising, such as sequencing, polynucleotides. Hetero-oligomeric pores can be made using methods known in the art (e.g. Protein Sci. 2002 July; 11(7):1813-24).

The hetero-oligomeric pore contains sufficient monomers to form the pore. The monomers may be of any type. The pore typically comprises at least 7, at least 8, at least 9 or at least 10 monomers, such as 7, 8, 9 or 10 monomers. The pore preferably comprises eight or nine monomers.

In a preferred embodiment, all of the monomers (such as 10, 9, 8 or 7 of the monomers) are monomers of the invention and at least one of them differs from the others. In a more preferred embodiment, the pore comprises eight or nine monomers of the invention and at least one of them differs from the others. They may all differ from one another.

The monomers of the invention in the pore are preferably approximately the same length or are the same length. The barrels of the monomers of the invention in the pore are preferably approximately the same length or are the same length. Length may be measured in number of amino acids and/or units of length.

In another preferred embodiment, at least one of the monomers is not a monomer of the invention. In this embodiment, the remaining monomers are preferably monomers of the invention. Hence, the pore may comprise 9, 8, 7, 6, 5, 4, 3, 2 or 1 monomers of the invention.

Any number of the monomers in the pore may not be a monomer of the invention. The pore preferably comprises seven or eight monomers of the invention and a monomer which is not a monomer of the invention. The monomers of the invention may be the same or different.

The monomers, such as the monomers of the invention, in the pore are preferably approximately the same length or are the same length. The barrels of the monomers in the pore are preferably approximately the same length or are the same length. Length may be measured in number of amino acids and/or units of length.

The pore may comprise one or more monomers which are not monomers of the invention. CsgG monomers which are not monomers of the invention include monomers comprising SEQ ID NO: 2, 3, 4, 5, 6, 7, 8, 9, 10, 11, 12, 13, 14, 15, 16, 17, 18, 19, 20, 21, 22 or 23 or a variant of SEQ ID NO: 2, 3, 4, 5, 6, 7, 8, 9, 10, 11, 12, 13, 14, 15, 16, 17, 18, 19, 20, 21, 22 or 23 in which none of the amino acids/positions discussed above in relation to the invention have been mutated/substituted. A comparative variant of SEQ ID NO: 2, 3, 4, 5, 6, 7, 8, 9, 10, 11, 12, 13, 14, 15, 16, 17, 18, 19, 20, 21, 22 or 23 is typically at least 50% homologous to SEQ ID NO: 2, 3, 4, 5, 6, 7, 8, 9, 10, 11, 12, 13, 14, 15, 16, 17, 18, 19, 20, 21, 22 or 23 over its entire sequence based on amino acid identity. More preferably, the comparative variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2, 3, 4, 5, 6, 7, 8, 9, 10, 11, 12, 13, 14, 15, 16, 17, 18, 19, 20, 21, 22 or 23 over the entire sequence.

In all the embodiments discussed above, one or more, such as 2, 3, 4, 5, 6, 7, 8, 9 or 10, of the mutant monomers is preferably chemically modified as discussed above.

Provided are hetero-oligomeric double pores.

Construct-Containing Pores

Also provided is a pore comprising at least one construct of the invention. The pore may be a double pore. The construct comprises two or more covalently attached monomers derived from CsgG wherein at least one of the monomers is a monomer of the invention. In other words, the construct must contain more than one monomer. The pore contains sufficient constructs and, if necessary, monomers to form the pore. For instance, an octameric pore may comprise (a) four constructs each comprising two constructs, (b) two constructs each comprising four monomers or (b) one construct comprising two monomers and six monomers that do not form part of a construct. For instance, an nonameric pore may comprise (a) four constructs each comprising two constructs and one monomer that does not form part of a construct, (b) two constructs each comprising four monomers and a monomer that does not form part of a construct or (b) one construct comprising two monomers and seven monomers that do not form part of a construct. Other combinations of constructs and monomers can be envisaged by the skilled person.

At least two of the monomers in the pore may be in the form of a construct of the invention. The construct, and hence the pore, comprises at least one monomer of the invention. The pore typically comprises at least 7, at least 8, at least 9 or at least 10 monomers, such as 7, 8, 9 or 10 monomers, in total (at least two of which must be in a construct). The pore preferably comprises eight or nine monomers (at least two of which must be in a construct).

The construct containing pore may be a homo-oligomer (i.e. include identical constructs) or be a hetero-oligomer (i.e. where at least one construct differs from the others).

A pore typically contains (a) one construct comprising two monomers and (b) 5, 6, 7 or 8 monomers. The construct may be any of those discussed above. The monomers may be any of those discussed above, including monomers of the invention, monomers comprising SEQ ID NO: 2 to 23 and monomers comprising a variant of SEQ ID NO: 2 to 23.

Another typical pore comprises more than one construct, such as more than one construct of the invention, for example two, three or four constructs of the invention. If necessary, such pores further comprise sufficient additional monomers or constructs to form the pore. The additional monomer(s) may be any of those discussed above, including monomers of the invention, monomers comprising SEQ ID NO: 2 to 23 and monomers comprising a variant of SEQ ID NO: 2 to 23 as discussed above. The additional construct(s) may be any of those discussed above or may be a construct comprising two or more covalently attached CsgG monomers each comprising a monomer comprising SEQ ID NO: 2 to 23 or a variant of SEQ ID NO: 2 to 23.

A further pore comprises only constructs comprising 2 monomers, for example a pore may comprise 4, 5, 6, 7 or 8 constructs comprising 2 monomers. At least one construct in such a pore is a construct of the invention, i.e. at least one monomer in the at least one construct, and preferably each monomer in the at least one construct, is a monomer of the invention. All of the constructs comprising 2 monomers may be constructs of the invention.

A specific pore comprises four constructs of the invention each comprising two monomers, wherein at least one monomer in each construct, and preferably each monomer in each construct, is a monomer of the invention. The constructs may oligomerise into a pore with a structure such that only one monomer of each construct contributes to the channel of the pore. Typically the other monomers of the construct will be on the outside of the channel of the pore. For example, the pore may comprise 7, 8, 9 or 10 constructs comprising 2 monomers where the channel comprises 7, 8, 9 or 10 monomers.

Mutations can be introduced into the construct as described above. The mutations may be alternating, i.e. the mutations are different for each monomer within a two monomer construct and the constructs are assembled as a homo-oligomer resulting in alternating modifications. In other words, monomers comprising MutA and MutB are fused and assembled to form an A-B:A-B:A-B:A-B pore. Alternatively, the mutations may be neighbouring, i.e. identical mutations are introduced into two monomers in a construct and this is then oligomerised with different mutant monomers or constructs. In other words, monomers comprising MutA are fused follow by oligomerisation with MutB-containing monomers to form A-A:B:B:B:B:B:B.

One or more of the monomers in a construct-containing pore may be chemically-modified as discussed above.

Also provided is a method of producing a monomer according to the invention or a construct according to the invention, comprising expressing a polynucleotide according to the invention in a suitable host cell and thereby producing the monomer or the construct.

Analyte Characterization

The double pore is particularly suited for characterising, such as sequencing, polynucleotides. Double pores comprising two wild type CsgG, or two CsgG homologues, may also be used in a method of characterizing an analyte, such as a polynucleotide. Double pores have two constrictions that can function as read heads in a method of characterizing a polynucleotide, particularly when sequencing a polynucleotide. Having two read heads is particularly beneficial when sequencing homopolymeric regions of a polynucleotide.

Accordingly, provided is a method of characterising a polynucleotide using a transmembrane pore, wherein the pore is a double pore comprising a first CsgG pore, or a homologue thereof, and a second CsgG pore, or a homologue thereof. In a preferred embodiment, the polynucleotide comprises a homopolymeric region. Also provided is the use of a double pore or a pore as disclosed herein to determine the presence, absence or one or more characteristics of a target analyte.

Provided is a method of sequencing a series of identical nucleotides in a polynucleotide, which method comprises contacting the a polynucleotide with a double pore or a pore as disclosed herein, such that the target analyte moves with respect to the pore; and taking one or more measurements as the analyte moves with respect to the pore and thereby determining the identity and number of identical nucleotides in the polynucleotide.

The pore may be one that has an elongated read head (barrel constriction) compared to the CsgG pores used for sequencing in the prior art, particularly compared to a CsgG pore comprising SEQ ID NO: 2 with Y51A and F56Q substitutions. The read head may be comparable to (the same, or approximately the same length), or longer than, the constriction in a wild-type CsgG pore comprising SEQ ID NO: 2. An elongated constriction that can function as a read head is advantageous in a method of characterizing a polynucleotide, particularly when sequencing a polynucleotide. Having a longer read head is particularly beneficial when sequencing homopolymeric regions of a polynucleotide.

In the method, the double pore may be any of the double pores, or the first CsgG pore, or homologue thereof may be any homooligomer and the second CsgG pore, or homologue thereof, may be any homooligomer, including wild-type homooligomers, and the first CsgG pore, or homologue thereof, and the second CsgG pore, or homologue thereof, may be identical to one another.

Provided is a method for determining the presence, absence or one or more characteristics of a target analyte, comprising:

(a) contacting the target analyte with a double pore or a pore as disclosed herein such that the target analyte moves with respect to the pore; and (b) taking one or more measurements as the analyte moves with respect to the pore and thereby determining the presence, absence or one or more characteristics of the analyte.

In a preferred embodiment, the analyte is a polynucleotide. In a more preferred embodiment the polynucleotide is a polynucleotide comprising a homopolymeric region.

The method may comprise determining one or more characteristics selected from (i) the length of the polynucleotide, (ii) the identity of the polynucleotide, (iii) the sequence of the polynucleotide, (iv) the secondary structure of the polynucleotide and (v) whether or not the polynucleotide is modified. The one or more characteristics of the analyte are typically measured by electrical measurement and/or optical measurement.

Provided is a method of determining the presence, absence or one or more characteristics of a target analyte. The method involves contacting the target analyte with a pore as disclosed herein such that the target analyte moves with respect to, such as through, the pore and taking one or more measurements as the analyte moves with respect to the pore and thereby determining the presence, absence or one or more characteristics of the analyte. The target analyte may also be called the template analyte or the analyte of interest.

Steps (a) and (b) are preferably carried out with a potential applied across the pore. As discussed in more detail below, the applied potential typically results in the formation of a complex between the pore and a polynucleotide binding protein. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The method is for determining the presence, absence or one or more characteristics of a target analyte. The method may be for determining the presence, absence or one or more characteristics of at least one analyte. The method may concern determining the presence, absence or one or more characteristics of two or more analytes. The method may comprise determining the presence, absence or one or more characteristics of any number of analytes, such as 2, 5, 10, 15, 20, 30, 40, 50, 100 or more analytes. Any number of characteristics of the one or more analytes may be determined, such as 1, 2, 3, 4, 5, 10 or more characteristics.

The target analyte is preferably a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The method may concern determining the presence, absence or one or more characteristics of two or more analytes of the same type, such as two or more proteins, two or more nucleotides or two or more pharmaceuticals. Alternatively, the method may concern determining the presence, absence or one or more characteristics of two or more analytes of different types, such as one or more proteins, one or more nucleotides and one or more pharmaceuticals.

The target analyte can be secreted from cells. Alternatively, the target analyte can be an analyte that is present inside cells such that the analyte must be extracted from the cells.

The analyte is preferably an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. It is to be understood that the target analyte can be modified by any method available in the art.

The protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-γ, and other cytokines such as TNF-α. The protein may be a bacterial protein, a fungal protein, a virus protein or a parasite-derived protein.

The target analyte is preferably a nucleotide, an oligonucleotide or a polynucleotide. Nucleotides and polynucleotides are discussed below. Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed below, including the abasic and modified nucleotides.

The polynucleotide is preferably a polynucleotide that comprises a homopolymeric region, i.e, the polynucleotide comprises a series of repeated nucleotides such as two or more adjacent A, G, C, T or U bases, such as 3, 4, 5, 6, 7, 8, 9, 10, 20, 30, 40, 50, 100 or more consecutive As, Gs, Cs, Ts or Us. The double pores and pores, particularly the pores in which the length of the narrowest part of the pore is the same as or longer than in the wild type CsgG pore, are particularly suited for determining the sequence of such homopolymeric polynucleotide sequences.

The target analyte, such as a target polynucleotide, may be present in any suitable sample. Examples of suitable samples are discussed below.

The pore is typically present in a membrane as discussed below. The target analyte may be coupled or delivered to the membrane using of the methods discussed below.

Any of the measurements discussed below can be used to determine the presence, absence or one or more characteristics of the target analyte. The method preferably comprises contacting the target analyte with the pore such that the analyte moves with respect to, such as moves through, the pore and measuring the current passing through the pore as the analyte moves with respect to the pore and thereby determining the presence, absence or one or more characteristics of the analyte.

The target analyte is present if the current flows through the pore in a manner specific for the analyte (i.e. if a distinctive current associated with the analyte is detected flowing through the pore). The analyte is absent if the current does not flow through the pore in a manner specific for the nucleotide. Control experiments can be carried out in the presence of the analyte to determine the way in which if affects the current flowing through the pore.

The method can be used to differentiate analytes of similar structure on the basis of the different effects they have on the current passing through a pore. Individual analytes can be identified at the single molecule level from their current amplitude when they interact with the pore. The method can also be used to determine whether or not a particular analyte is present in a sample. The method can also be used to measure the concentration of a particular analyte in a sample. Analyte characterisation using pores other than CsgG is known in the art.

Characterisation, such as sequencing, of a polynucleotide using a transmembrane pore may be carried out such as disclosed in WO2013/041878. As the target polynucleotide moves with respect to, or through the pore, the analyte may be characterised from the distinctive ion current signature produced, typically by measuring the ion current flow through the pore. The level of current measured at any particular time is typically dependent on multiple polymer (for example nucleotide) units. The number of polymer units contributing to the current at any time will depend on the structure of the polymer, particularly on the structure of the barrel constriction(s). For example, from about 3 to about 20, such a 5, 6, 7, 8, 9, 10, 12, 13, 14 or 15 polymer units may influence the current level at any one time.

Analytical techniques to characterise the polynucleotide may for example involve the use of an HMM, a neural network and for example a Forwards Backwards algorithm or Viterbi algorithm to determine the likelihood of the series of measurements corresponding to a particular sequence. Alternatively the polynucleotide may be characterised by determining a feature vector and comparing the feature vector to another feature vector, which may be known, such as disclosed in WO 2013/121224. However, the analytical techniques used to characterise the polynucleotide are not necessarily restricted to the above examples.

Polynucleotide Characterisation

Provided is a method of characterising a target polynucleotide, such as sequencing a polynucleotide. There are two main strategies for characterising or sequencing polynucleotides using nanopores, namely strand characterisation/sequencing and exonuclease characterisation/sequencing. The method may concern either method.

In strand sequencing, the DNA is translocated through the nanopore either with or against an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In one embodiment, the method of characterising a target polynucleotide involves contacting the target sequence with a pore as disclosed herein and a helicase enzyme. Any helicase may be used in the method. Suitable helicases are discussed below. Helicases may work in two modes with respect to the pore. First, the method is preferably carried out using a helicase such that it controls movement of the target sequence through the pore with the field resulting from the applied voltage. In this mode the 5' end of the DNA is first captured in the pore, and the enzyme controls movement of the DNA into the pore such that the target sequence is passed through the pore with the field until it finally translocates through to the trans side of the bilayer. Alternatively, the method is preferably carried out such that a helicase enzyme controls movement of the target sequence through the pore against the field resulting from the applied voltage. In this mode the 3' end of the DNA is first captured in the pore, and the enzyme controls movement of the DNA through the pore such that the target sequence is pulled out of the pore against the applied field until finally ejected back to the cis side of the bilayer.

In exonuclease sequencing, an exonuclease releases individual nucleotides from one end of the target polynucleotide and these individual nucleotides are identified as discussed below. In another embodiment, the method of characterising a target polynucleotide involves contacting the target sequence with a pore and an exonuclease enzyme. Any of the exonuclease enzymes discussed below may be used in the method. The enzyme may be covalently attached to the pore as discussed below.

Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves contacting the polynucleotide with the exonuclease so that the nucleotides are digested from the end of the polynucleotide at a rate that allows characterisation or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used.

The rate at which the exonuclease functions is typically slower than the optimal rate of a wild-type exonuclease. A suitable rate of activity of the exonuclease in the method involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used.

In the strand characterisation embodiment, the method comprises contacting the polynucleotide with a pore as disclosed herein such that the polynucleotide moves with respect to, such as through, the pore and taking one or more measurements as the polynucleotide moves with respect to the pore, wherein the measurements are indicative of one or more characteristics of the polynucleotide, and thereby characterising the target polynucleotide.

In the exonucleotide characterisation embodiment, the method comprises contacting the polynucleotide with a pore as disclosed herein and an exonucleoase such that the exonuclease digests individual nucleotides from one end of the target polynucleotide and the individual nucleotides move with respect to, such as through, the pore and taking one or more measurements as the individual nucleotides move with respect to the pore, wherein the measurements are indicative of one or more characteristics of the individual nucleotides, and thereby characterising the target polynucleotide.

An individual nucleotide is a single nucleotide. An individual nucleotide is one which is not bound to another nucleotide or polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand. The nucleotide can be any of those discussed below.

The individual nucleotides may interact with the pore in any manner and at any site. The nucleotides preferably reversibly bind to the pore via or in conjunction with an adaptor as discussed above. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane.

During the interaction between the individual nucleotide and the pore, the nucleotide typically affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method on a test sample can then be compared with those derived from such a control experiment in order to identify a particular nucleotide in the sample or determine whether a particular nucleotide is present in the sample. The frequency at which the current flowing through the pore is affected in a manner indicative of a particular nucleotide can be used to determine the concentration of that nucleotide in the sample. The ratio of different nucleotides within a sample can also be calculated. For instance, the ratio of dCMP to methyl-dCMP can be calculated.

The method involves measuring one or more characteristics of the target polynucleotide. The target polynucleotide may also be called the template polynucleotide or the polynucleotide of interest.

This embodiment also uses a pore as disclosed herein. Any of the pores and embodiments discussed above with reference to the target analyte may be used.

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. The polynucleotide is preferably single stranded. Single stranded polynucleotide characterization is referred to as 1D in the Examples. At least a portion of the polynucleotide may be double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety. Bridged nucleic acids (BNAs) are modified RNA nucleotides. They may also be called constrained or inaccessible RNA. BNA monomers can contain a five-membered, six-membered or even a seven-membered bridged structure with a "fixed" C3'-endo sugar puckering. The bridge is synthetically incorporated at the 2', 4'-position of the ribose to produce a 2', 4'-BNA monomer.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Any number of polynucleotides can be investigated. For instance, the method may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial. For instance, the method may be used to verify the sequence of a manufactured oligonucleotide. The method is typically carried out in vitro.

Sample

The polynucleotide is typically present in any suitable sample. The method is typically carried out on a sample that is known to contain or suspected to contain the polynucleotide. Alternatively, the method may be carried out on a sample to confirm the identity of a polynucleotide whose presence in the sample is known or expected.

The sample may be a biological sample. The method may be carried out in vitro using a sample obtained from or extracted from any organism or microorganism. The organism or microorganism is typically archaeal, prokaryotic or eukaryotic and typically belongs to one of the five kingdoms: plantae, animalia, fungi, monera and protista. The method may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum.

Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the method, for example by centrifugation or by passage through a membrane that filters out unwanted molecules or cells, such as red blood cells. The may be measured immediately upon being taken. The sample may also be typically stored prior to assay, preferably below −70° C.

Characterisation

The method may involve measuring two, three, four or five or more characteristics of the polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the method, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii, iv,v}, {ii,iii,iv,v} or {i,ii,iii,iv,v}. Different combinations of (i) to (v) may be measured for the first polynucleotide compared with the second polynucleotide, including any of those combinations listed above.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., *Proc Natl Acad Sci,* 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The target polynucleotide is contacted with a pore as disclosed herein. The pore is typically present in a membrane. Suitable membranes are discussed below. The method may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The method may be carried out using the apparatus described in WO 2008/102120.

A variety of different types of measurements may be made. This includes without limitation: electrical measurements and optical measurements. Possible electrical measurements include: current measurements, impedance measurements, tunnelling measurements (Ivanov AP et al., Nano Lett. 2011 Jan. 12; 11(1):279-85), and FET measurements (WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and WO 2000/28312. Alternatively, electrical measurements may be made using a multi-channel system, for example as described in WO 2009/077734 and WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The method may involve measuring the current passing through the pore as the polynucleotide moves with respect to the pore. Therefore the apparatus used in the method may also comprise an electrical circuit capable of applying a potential and measuring an electrical signal across the membrane and pore. The methods may be carried out using a patch clamp or a voltage clamp. The methods preferably involve the use of a voltage clamp.

The method may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to –5 V, such as from +4 V to –4 V, +3 V to –3 V or +2 V to –2 V. The voltage used is typically from –600 mV to +600 mV or –400 mV to +400 mV. The voltage used is preferably in a range having a lower limit selected from –400 mV, –300 mV, –200 mV, –150 mV, –100 mV, –50 mV, –20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The method is typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The method is typically carried out in the presence of a buffer. In the exemplary apparatus discussed above, the buffer is present in the aqueous solution in the chamber. Any buffer may be used in the method. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The method may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Polynucleotide-Binding Protein

The strand characterisation method preferably comprises contacting the polynucleotide with a polynucleotide binding protein such that the protein controls the movement of the polynucleotide with respect to, such as through, the pore.

More preferably, the method comprises (a) contacting the polynucleotide with a pore as disclosed herein and a polynucleotide binding protein such that the protein controls the movement of the polynucleotide with respect to, such as through, the pore and (b) taking one or more measurements as the polynucleotide moves with respect to the pore, wherein the measurements are indicative of one or more characteristics of the polynucleotide, and thereby characterising the polynucleotide.

More preferably, the method comprises (a) contacting the polynucleotide with a pore as disclosed herein and a polynucleotide binding protein such that the protein controls the movement of the polynucleotide with respect to, such as through, the pore and (b) measuring the current through the pore as the polynucleotide moves with respect to the pore, wherein the current is indicative of one or more characteristics of the polynucleotide, and thereby characterising the polynucleotide.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The protein may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in WO 2010/086603.

Preferred enzymes are polymerases, exonucleases, helicases and topoisomerases, such as gyrases. Suitable enzymes include, but are not limited to, exonuclease I from *E. coli*, exonuclease III enzyme from *E. coli*, RecJ from *T. thermophilus* and bacteriophage lambda exonuclease, TatD exonuclease and variants thereof. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase or a variant thereof. The topoisomerase is preferably a member of any of the Moiety Classification (EC) groups 5.99.1.2 and 5.99.1.3.

The enzyme is most preferably derived from a helicase, such as Hel308 Mbu, Hel308 Csy, Hel308 Tga, Hel308 Mhu, TraI Eco, XPD Mbu or a variant thereof. Any helicase may be used. The helicase may be or be derived from a Hel308 helicase, a RecD helicase, such as TraT helicase or a TrwC helicase, a XPD helicase or a Dda helicase. The helicase may be any of the helicases, modified helicases or helicase constructs disclosed in: WO 2013/057495; WO 2013/098562; WO2013098561; WO 2014/013260; WO 2014/013259; WO 2014/013262 and WO2015/055981.

Any number of helicases may be used. For instance, 1, 2, 3, 4, 5, 6, 7, 8, 9, 10 or more helicases may be used. In some embodiments, different numbers of helicases may be used.

The method preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs are described in WO 2014/013260; WO 2014/013259; WO 2014/013262 and WO2015/055981.

A variant of a naturally occurring helicase which retains polynucleotide binding ability may be used. Polynucleotide binding ability can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below). A preferred molecular brake is TrwC Cba-Q594A. This variant does not function as a helicase (i.e. binds polynucleotides but does not move along them when provided with all the necessary components to facilitate movement, e.g. ATP and $Mg^{2+}$).

The enzyme may be covalently attached to the pore. Any method may be used to covalently attach the enzyme to the pore.

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Helicase(s) and Molecular Brake(s)

In a preferred embodiment, the method comprises providing the polynucleotide with one or more helicases and one or more molecular brakes attached to the polynucleotide; contacting the polynucleotide with a double pore or a pore as disclosed herein and applying a potential across the pore such that the one or more helicases and the one or more molecular brakes are brought together and both control the movement of the polynucleotide with respect to, such as through, the pore; and taking one or more measurements as the polynucleotide moves with respect to the pore wherein the measurements are indicative of one or more characteristics of the polynucleotide and thereby characterising the polynucleotide. This type of method is disclosed in WO2015/110777.

The one or more helicases may be any of those discussed above. The one or more molecular brakes may be any compound or molecule which binds to the polynucleotide and slows the movement of the polynucleotide through the pore. The one or more molecular brakes preferably comprise one or more compounds which bind to the polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin (am$_7$-βCD), 6-monodeoxy-6-monoamino-β-cyclodextrin or heptakis-(6-deoxy-6-guanidino)-cyclodextrin (gu$_7$-βCD).

The one or more molecular brakes are preferably one or more single stranded binding proteins (SSB). The one or more molecular brakes are more preferably a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably one of the SSBs disclosed in WO 2014/013259.

The one or more molecular brakes are preferably one or more polynucleotide binding proteins. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase which act as molecular brakes are disclosed in U.S. Pat. No. 5,576,204. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are be used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucleotide binding domain through which in at least one conformational state the polynucleotide can unbind from the helicase. This is disclosed in WO 2014/013260.

Preferred helicase constructs are described in WO 2014/013260, WO 2014/013259, WO 2014/013262 and WO2015/055981.

If the one or more helicases are used in the active mode (i.e. when the one or more helicases are provided with all the necessary components to facilitate movement, e.g. ATP and $Mg^{2+}$), the one or more molecular brakes are preferably (a) used in an inactive mode (i.e. are used in the absence of the necessary components to facilitate movement or are incapable of active movement), (b) used in an active mode where the one or more molecular brakes move in the opposite direction to the one or more helicases or (c) used in an active mode where the one or more molecular brakes move in the same direction as the one or more helicases and more slowly than the one or more helicases.

If the one or more helicases are used in the inactive mode (i.e. when the one or more helicases are not provided with all the necessary components to facilitate movement, e.g. ATP and $Mg^{2+}$ or are incapable of active movement), the one or more molecular brakes are preferably (a) used in an inactive mode (i.e. are used in the absence of the necessary components to facilitate movement or are incapable of active movement) or (b) used in an active mode where the one or more molecular brakes move along the polynucleotide in the same direction as the polynucleotide through the pore.

The one or more helicases and one or more molecular brakes may be attached to the polynucleotide at any positions so that they are brought together and both control the movement of the polynucleotide through the pore. The one or more helicases and one or more molecular brakes are at least one nucleotide apart, such as at least 5, at least 10, at least 50, at least 100, at least 500, at least 1000, at least 5000, at least 10,000, at least 50,000 nucleotides or more apart. If the method concerns characterising a double stranded polynucleotide provided with a Y adaptor at one end and a hairpin loop adaptor at the other end, the one or more helicases are preferably attached to the Y adaptor and the one or more molecular brakes are preferably attached to the hairpin loop adaptor. In this embodiment, the one or more molecular brakes are preferably one or more helicases that are modified such that they bind the polynucleotide but do not function as a helicase. The one or more helicases attached to the Y adaptor are preferably stalled at a spacer as discussed in more detail below. The one or more molecular brakes attach to the hairpin loop adaptor are preferably not stalled at a spacer. The one or more helicases and the one or more molecular brakes are preferably brought together when the one or more helicases reach the hairpin loop. The one or more helicases may be attached to the Y adaptor before the Y adaptor is attached to the polynucleotide or after the Y adaptor is attached to the polynucleotide. The one or more molecular brakes may be attached to the hairpin loop adaptor before the hairpin loop adaptor is attached to the polynucleotide or after the hairpin loop adaptor is attached to the polynucleotide.

The one or more helicases and the one or more molecular brakes are preferably not attached to one another. The one or more helicases and the one or more molecular brakes are more preferably not covalently attached to one another. The one or more helicases and the one or more molecular brakes are preferably not attached as described in WO 2014/013260, WO 2014/013259, WO 2014/013262 and WO2015/055981.

Spacers

The one or more helicases may be stalled at one or more spacers as discussed in WO2014/135838. Any configuration of one or more helicases and one or more spacers disclosed in WO2014/135838 may be used.

The one or more spacers are preferably part of the polynucleotide, for instance they interrupt(s) the polynucleotide sequence. The one or more spacers are preferably not part of one or more blocking molecules, such as speed bumps, hybridised to the polynucleotide.

There may be any number of spacers in the polynucleotide, such as 1, 2, 3, 4, 5, 6, 7, 8, 9, 10 or more spacers. There are preferably two, four or six spacers in the polynucleotide. There may be one or more spacers in different regions of the polynucleotide, such as one or more spacers in the Y adaptor and/or hairpin loop adaptor.

The one or more spacers may comprise any molecule or combination of molecules that stalls the one or more helicases. The one or more spacers may comprise any molecule or combination of molecules that prevents the one or more helicases from moving along the polynucleotide. It is straightforward to determine whether or not the one or more helicases are stalled at one or more spacers in the absence of a transmembrane pore and an applied potential. For instance, the ability of a helicase to move past a spacer and displace a complementary strand of DNA can be measured by PAGE.

The one or more spacers typically comprise a linear molecule, such as a polymer. The one or more spacers typically have a different structure from the polynucleotide. For instance, if the polynucleotide is DNA, the one or more spacers are typically not DNA. In particular, if the polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA) or a synthetic polymer with nucleotide side chains. The one or more spacers may comprise one or more nucleotides in the opposite direction from the polynucleotide. For instance, the one or more spacers may comprise one or more nucleotides in the 3' to 5' direction when the polynucleotide is in the 5' to 3' direction. The nucleotides may be any of those discussed above.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies@).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSp18 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

If linear molecule spacers are used, the polynucleotide may be provided with a double stranded region of polynucleotide adjacent to the end of each spacer past which the one or more helicases are to be moved. The double stranded region typically helps to stall the one or more helicases on the adjacent spacer. The presence of the double stranded region(s) is particularly preferred if the method is carried out at a salt concentration of about 100 mM or lower. Each double stranded region is typically at least 10, such as at least 12, nucleotides in length. If the polynucleotide is single stranded, a double stranded region may be formed by hybridising a shorter polynucleotide to a region adjacent to a spacer. The shorter polynucleotide is typically formed from the same nucleotides as the polynucleotide, but may be formed from different nucleotides. For instance, the shorter polynucleotide may be formed from LNA.

If linear molecule spacers are used, the polynucleotide may be provided with a blocking molecule at the end of each spacer opposite to the end past which the one or more helicases are to be moved. This can help to ensure that the one or more helicases remain stalled on each spacer. It may also help retain the one or more helicases on the polynucleotide in the case that it/they diffuse(s) off in solution. The blocking molecule may be any of the chemical groups discussed below which physically cause the one or more helicases to stall. The blocking molecule may be a double stranded region of polynucleotide.

The one or more spacers preferably comprise one or more chemical groups which physically cause the one or more The method is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the method is carried out in the presence of free nucleotides and a helicase cofactor as discussed below (such that the one of more helicases are in the active mode), one or more longer spacers are typically used to ensure that the one or more helicases are stalled on the polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method, the shorter the one or more spacers that are typically used and vice versa.

Preferred combinations of features are shown in the Table below.

| Polynucleotide | Spacer composition* | Spacer length (i.e. number of*) | Salt [ ] | | Free nucleotides? | Helicase cofactor? |
|---|---|---|---|---|---|---|
| DNA | iSpC3 | 4 | 1M | | Yes | Yes |
| DNA | iSp18 | 4 | 100-1000 | mM | Yes | Yes |
| DNA | iSp18 | 6 | <100-1000 | mM | Yes | Yes |
| DNA | iSp18 | 2 | 1M | | Yes | Yes |
| DNA | iSpC3 | 12 | <100-1000 | mM | Yes | Yes |
| DNA | iSpC3 | 20 | <100-1000 | mM | Yes | Yes |
| DNA | iSp9 | 6 | 100-1000 | mM | Yes | Yes |
| DNA | idSp | 4 | 1M | | Yes | Yes | helicases to stall. The one or more chemical groups are preferably one or more pendant chemical groups. The one or more chemical groups may be attached to one or more nucleobases in the polynucleotide. The one or more chemical groups may be attached to the polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

Different spacers in the polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more a basics and a fluorophore.

Suitable spacers can be designed depending on the type of polynucleotide and the conditions under which the method is carried out. Most helicases bind and move along DNA and so may be stalled using anything that is not DNA. Suitable molecules are discussed above.

The method may involve moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 4 above may be increased 1.5 fold, 2 fold, 2.5 fold or 3 fold.

Membrane

The double pore or pore as disclosed herein may be present in a membrane. In the method, the polynucleotide is typically contacted with the double pore or pore in a membrane. Any membrane may be used. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. WO2014/064443 or WO2014/064444.

The amphiphilic molecules may be chemically-modified or functionalised to facilitate coupling of the polynucleotide. The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s-1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in WO 2008/102121, WO 2009/077734 and WO 2006/100484.

Methods for forming lipid bilayers are known in the art. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. WO 2009/077734. Advantageously in this method, the lipid bilayer is formed from dried lipids. In a most preferred embodiment, the lipid bilayer is formed across an opening as described in WO2009/077734.

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconoic acid), palmitic acid (n-Hexadecanoic acid), stearic acid (n-Octadecanoic) and arachidic (n-Eicosanoic); unsaturated hydrocarbon chains, such as oleic acid (cis-9-Octade-canoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phospho-ethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoetha-nolamine-N-(Biotinyl). Suitable lipids whose tail groups have been chemically-modified include, but are not limited to, polymerisable lipids, such as 1,2-bis(10,12-tri-cosadiynoyl)-sn-Glycero-3-Phosphocholine; fluorinated lipids, such as 1-Palmitoyl-2-(16-Fluoropalmitoyl)-sn-Glyc-ero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-

Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lyso-phospholipids, such as 1-Acyl-2-Hydroxy-sn-Glycero-3-Phosphocholine; and ceramides.

In another preferred embodiment, the membrane comprises a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO 2009/035647. If the membrane comprises a solid state layer, the pore is typically present in an amphiphilic membrane or layer contained within the solid state layer, for instance within a hole, well, gap, channel, trench or slit within the solid state layer. The skilled person can prepare suitable solid state/amphiphilic hybrid systems. Suitable systems are disclosed in WO 2009/020682 and WO 2012/005857. Any of the amphiphilic membranes or layers discussed above may be used.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method is typically carried out in vitro.

Coupling

The polynucleotide is preferably coupled to the membrane comprising the pore. The method may comprise coupling the polynucleotide to the membrane comprising the pore. The polynucleotide is preferably coupled to the membrane using one or more anchors. The polynucleotide may be coupled to the membrane using any known method.

Each anchor comprises a group which couples (or binds) to the polynucleotide and a group which couples (or binds) to the membrane. Each anchor may covalently couple (or bind) to the polynucleotide and/or the membrane. If a Y adaptor and/or a hairpin loop adaptors are used, the polynucleotide is preferably coupled to the membrane using the adaptor(s).

The polynucleotide may be coupled to the membrane using any number of anchors, such as 2, 3, 4 or more anchors. For instance, a polynucleotide may be coupled to the membrane using two anchors each of which separately couples (or binds) to both the polynucleotide and membrane.

The one or more anchors may comprise the one or more helicases and/or the one or more molecular brakes.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut to broken down, such as a restriction site or a photolabile group.

Functionalised linkers and the ways in which they can couple molecules are known in the art. For instance, linkers functionalised with maleimide groups will react with and attach to cysteine residues in proteins. In the present context, the protein may be present in the membrane or may be used to couple (or bind) to the polynucleotide. This is discussed in more detail below.

Crosslinkage of polynucleotides can be avoided using a "lock and key" arrangement. Only one end of each linker may react together to form a longer linker and the other ends of the linker each react with the polynucleotide or membrane respectively. Such linkers are described in WO 2010/086602.

The use of a linker is preferred in the sequencing embodiments discussed below. If a polynucleotide is permanently coupled directly to the membrane in the sense that it does not uncouple when interacting with the pore (i.e. does not uncouple in step (b) or (e)), then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

For certain applications, such as aptamer detection, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 5 below.

TABLE 5

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucleotides to lipid membrane assemblies." *J Am Chem Soc* 126(33): 10224-5 |
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxy-nucleotidyl transferase." *Anal Biochem* 169(2): 376-82). Streptavidin/biotin and/or streptavidin/desthiobiotin coupling may be used for any other polynucleotide. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the polynucleotide to the membrane via hybridisation. Hybridisation in the one or more anchors allows coupling in a transient manner as discussed above. The hybridisation may be present in any part of the one or more anchors, such as between the one or more anchors and the polynucleotide, within the one or more anchors or between the one or more anchors and the membrane. For instance, a linker may comprise two or more polynucleotides, such as 3, 4 or 5 polynucleotides, hybridised together. The one or more anchors may hybridise to the polynucleotide. The one or more anchors may hybridise directly to the polynucleotide or directly to a Y adaptor and/or leader sequence attached to the polynucleotide or directly to a hairpin loop adaptor attached to the polynucleotide (as discussed below). Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a hairpin loop adaptor attached to the polynucleotide (as discussed below).

The one or more anchors may comprise a single stranded or double stranded polynucleotide. One part of the anchor may be ligated to a single stranded or double stranded polynucleotide. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the a double stranded polynucleotide, this can be achieved using T4 RNA ligase I as for ligation to other regions of single stranded polynucleotide. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a polynucleotide binding protein or a chemical group, to the membrane and allowing the one or more anchors to interact with the polynucleotide or by functionalising the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before contacting with the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein), Ni-NTA (for binding to poly-histidine or poly-histidine tagged proteins) or a peptides (such as an antigen).

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Double Stranded Polynucleotide

The polynucleotide may be double stranded. If the polynucleotide is double stranded, the method preferably further comprises before the contacting step ligating a bridging moiety, such as a hairpin loop, to one end of the polynucleotide. The two strands of the polynucleotide may then be separated as or before the polynucleotide is contacted with the pore. The two strands may be separated as the polynucleotide movement through the pore is controlled by a polynucleotide binding protein, such as a helicase, or molecular brake.

Linking and interrogating both strands on a double stranded construct in this way increases the efficiency and accuracy of characterisation.

The bridging moiety is capable of linking the two strands of the target polynucleotide. The bridging moiety typically covalently links the two strands of the target polynucleotide. The bridging moiety can be anything that is capable of linking the two strands of the target polynucleotide, provided that the bridging moiety does not interfere with movement of the single stranded polynucleotide through the transmembrane pore.

The bridging moiety may be linked to the target polynucleotide by any suitable means known in the art. The bridging moiety may be synthesised separately and chemically attached or enzymatically ligated to the target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the target polynucleotide Suitable bridging moieties include, but are not limited to a polymeric linker, a chemical linker, a polynucleotide or a polypeptide. Preferably, the bridging moiety comprises DNA, RNA, modified DNA (such as abasic DNA), RNA, PNA, LNA or PEG. The bridging moiety is more preferably DNA or RNA.

The bridging moiety is most preferably a hairpin loop or a hairpin loop adaptor. Suitable hairpin adaptors can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin adaptor may be ligated to either end of the first and/or second polynucleotide, i.e. the 5' or the 3' end. The hairpin adaptor may be ligated to the first and/or second polynucleotide using any method known in the art. The hairpin adaptor may be ligated using a ligase, such as T4 DNA ligase, E. coli DNA ligase, Taq DNA ligase, Tma DNA ligase and 9°N DNA ligase.

The two strands of the polynucleotide may be separated using any method known in the art. For instance, they may be separated by a polynucleotide binding protein or using conditions which favour dehybridisation (examples of conditions which favour dehybridisation include, but are not limited to, high temperature, high pH and the addition of agents that can disrupt hydrogen bonding or base pairing, such as formamide and urea).

The hairpin adaptor preferably comprises a selectable binding moiety. This allows the first and/or second polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used. In preferred embodiments, the moiety binds to a surface to which no other moiety binds.

Suitable selective binding moieties are known in the art. Preferred selective binding moieties include, but are not limited to, biotin, a polynucleotide sequence, antibodies, antibody fragments, such as Fab and scFv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologous sequences. Alternatively, selectable polynucleotide sequences specifically bind to a surface coated with polynucleotide binding proteins.

The hairpin adaptor and/or the selectable binding moiety may comprise a region that can be cut, nicked, cleaved or hydrolysed. Such a region can be designed to allow the first and/or second polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The double stranded target polynucleotide preferably comprises a leader sequence at the opposite end of the bridging moiety, such as a hairpin loop or hairpin loop adaptor. Leader sequences are discussed in more detail below.

Round the Corner Sequencing

In a preferred embodiment, a target double stranded polynucleotide is provided with a bridging moiety, such as a hairpin loop or hairpin loop adaptor, at one end and the method comprises contacting the polynucleotide with the pore such that both strands of the polynucleotide move through the pore and taking one or more measurements as the both strands of the polynucleotide move with respect to the pore wherein the measurements are indicative of one or more characteristics of the strands of the polynucleotide and thereby characterising the target double stranded polynucleotide. In another preferred embodiment, a target double stranded polynucleotide is provided with a bridging moiety, such as a hairpin loop or hairpin loop adaptor, at one end and the method comprises contacting the polynucleotide with the pore and exonuclease such that both strands of the polynucleotide are digested to form individual nucleotides. Any of the embodiments discussed above equally apply to this embodiment.

Leader Sequence

Before the contacting step in the strand characterisation/sequencing method, the method preferably comprises attaching to the polynucleotide a leader sequence which preferentially threads into the pore. The leader sequence facilitates the method. The leader sequence is designed to preferentially thread into the pore and thereby facilitate the movement of polynucleotide through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The leader sequence is preferably part of a Y adaptor as defined below.

Double Coupling

The method may involve double coupling of a double stranded polynucleotide. In a preferred embodiment, the method comprises:

(a) providing the double stranded polynucleotide with a Y adaptor at one end and a bridging moiety adaptor, such as a hairpin loop adaptor, at the other end, wherein the Y adaptor comprises one or more first anchors for coupling the polynucleotide to the membrane, wherein the bridging moiety adaptor comprises one or more second anchors for coupling the polynucleotide to the membrane and wherein the strength of coupling of the bridging moiety adaptor to the membrane is greater than the strength of coupling of the Y adaptor to the membrane;

(b) contacting the polynucleotide provided in step (a) with a pore, for example a double pore, as disclosed herein such that the polynucleotide moves with respect to, such as through, the pore; and (c) taking one or more measurements as the polynucleotide moves with respect to the pore, wherein the measurements are indicative of one or more characteristics of the polynucleotide, and thereby characterising the target polynucleotide.

This type of method is discussed in detail in the UK Application No. 1406147.7.

The double stranded polynucleotide is provided with a Y adaptor at one end and a bridging moiety adaptor at the other end. The Y adaptor and/or the bridging moiety adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail above.

The Y adaptor preferably comprises a leader sequence which preferentially threads into the pore. This is discussed above.

The bridging moiety adaptor preferably comprises a selectable binding moiety as discussed above. The bridging moiety adaptor and/or the selectable binding moiety may comprise a region that can be cut, nicked, cleaved or hydrolysed as discussed above.

If one or more helicases and one or more molecular brakes are used as discussed above, the Y adaptor preferably comprises the one or more helicases and the bridging moiety adaptor preferably comprises the one or more molecular brakes.

The Y adaptor and/or the bridging moiety adaptor may be ligated to the polynucleotide using any method known in the art. One or both of the adaptors may be ligated using a ligase, such as T4 DNA ligase, *E. coli* DNA ligase, Taq DNA ligase, Tma DNA ligase and 9°N DNA ligase. Alternatively, the adaptors may be added to the polynucleotide using the methods discussed below.

In a preferred embodiment, step a) of the method comprises modifying the double stranded polynucleotide so that it comprises the Y adaptor at one end and the bridging moiety adaptor at the other end. Any manner of modification can be used. The method preferably comprises modifying the double stranded polynucleotide. This is discussed in more detail below. The methods of modification and characterisation may be combined in any way.

The strength of coupling (or binding) of the bridging moiety adaptor to the membrane is greater than the strength of coupling (or binding) of the Y adaptor to the membrane. This can be measured in any way. A suitable method for measuring the strength of coupling (or binding) is disclosed in the Examples of the UK Application No. 1406147.7.

The strength of coupling (or binding) of the bridging moiety adaptor is preferably at least 1.5 times the strength of coupling (or binding) of the Y adaptor, such as at least twice, at least three times, at least four times, at least five or at least ten times the strength of coupling (or binding) of the anchor adaptor. The affinity constant (Kd) of the bridging moiety adaptor for the membrane is preferably at least 1.5 times the affinity constant of the Y adaptor, such as at least twice, at least three times, at least four times, at least five or at least ten times the strength of coupling of the Y adaptor.

There are several ways in which the bridging moiety adaptor couples (or binds) more strongly to the membrane than the Y adaptor. For instance, the bridging moiety adaptor may comprise more anchors than the Y adaptor. For instance, the bridging moiety adaptor may comprise 2, 3 or more second anchors whereas the Y adaptor may comprise one first anchor.

The strength of coupling (or binding) of the one or more second anchors to the membrane may be greater than the strength of coupling (or binding) of the one or more first anchors to the membrane. The strength of coupling (or binding) of the one or more second anchors to the bridging moiety adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used. Strength of coupling (or binding) may be measure using known techniques in the art.

The one or more second anchors preferably comprise one or more groups which couple(s) (or bind(s)) to the membrane with a greater strength than the one or more groups in the one or more first anchors which couple(s) (or bind(s)) to the membrane. In preferred embodiments, the bridging moiety adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the bridging moiety adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine.

Adding Hairpin Loops and Leader Sequences

Before provision, a double stranded polynucleotide may be contacted with a MuA transposase and a population of double stranded MuA substrates, wherein a proportion of the substrates in the population are Y adaptors comprising the leader sequence and wherein a proportion of the substrates in the population are hairpin loop adaptors. The transposase fragments the double stranded polynucleotide analyte and ligates MuA substrates to one or both ends of the fragments. This produces a plurality of modified double stranded polynucleotides comprising the leader sequence at one end and the hairpin loop at the other. The modified double stranded polynucleotides may then be investigated using the method.

Each substrate in the population preferably comprises at least one overhang of universal nucleotides such that the transposase fragments the template polynucleotide and ligates a substrate to one or both ends of the double stranded fragments and thereby produces a plurality of fragment/substrate constructs and wherein the method further comprises ligating the overhangs to the fragments in the constructs and thereby producing a plurality of modified double stranded polynucleotides. Suitable universal nucleotides are discussed above. The overhang is preferably five nucleotides in length.

Alternatively, each substrate in population preferably comprises (i) at least one overhang and (ii) at least one nucleotide in the same strand as the at least one overhang which comprises a nucleoside that is not present in the template polynucleotide such that the transposase fragments the template polynucleotide and ligates a substrate to one or both ends of the double stranded fragments and thereby produces a plurality of fragment/substrate constructs, and wherein the method further comprises (a) removing the overhangs from the constructs by selectively removing the at least one nucleotide and thereby producing a plurality of double stranded constructs comprising single stranded gaps and (b) repairing the single stranded gaps in the constructs and thereby producing a plurality of modified double stranded polynucleotides. The polynucleotide typically comprises the nucleosides deoxyadenosine (dA), deoxyuridine (dU) and/or thymidine (dT), deoxyguanosine (dG) and deoxycytidine (dC). The nucleoside that is not present in the polynucleotide is preferably abasic, adenosine (A), uridine (U), 5-methyluridine (m⁵U), cytidine (C) or guanosine (G) or comprises urea, 5, 6 dihydroxythymine, thymine glycol, 5-hydroxy-5 methylhydanton, uracil glycol, 6-hydroxy-5, 6-dihdrothimine, methyltartronylurea, 7, 8-dihydro-8-oxoguanine (8-oxoguanine), 8-oxoadenine, fapy-guanine, methyfapy-guanine, fapy-adenine, aflatoxin B1-fapy-guanine, 5-hydroxy-cytosine, 5-hydroxy-uracil, 3-methyladenine, 7-methylguanine, 1,N6-ethenoadenine, hypoxanthine, 5-hydroxyuracil, 5-hydroxymethyluracil, 5-formyluracil or a cis-syn-cyclobutane pyrimidine dimer. The at least one nucleotide preferably is 10 nucleotides or fewer from the overhang. The at least one nucleotide is the first nucleotide in the overhang. All of the nucleotides in the overhang preferably comprise a nucleoside that is not present in the template polynucleotide.

These MuA based methods are disclosed in International Application No. PCT/GB2014/052505. They are also discussed in detail in the UK Application No. 1406147.7.

One or more helicases may be attached to the MuA substrate Y adaptors before they are contacted with the double stranded polynucleotide and MuA transposase. Alternatively, one or more helicases may be attached to the MuA substrate Y adaptors before they are contacted with the double stranded polynucleotide and MuA transposase.

One or more molecular brakes may be attached to the MuA substrate hairpin loop adaptors before they are contacted with the double stranded polynucleotide and MuA transposase. Alternatively, one or more molecular brakes may be attached to the MuA substrate hairpin loop adaptors before they are contacted with the double stranded polynucleotide and MuA transposase.

Uncoupling

The method may involve characterising multiple target polynucleotides and uncoupling of the at least the first target polynucleotide.

In a preferred embodiment, the method involves characterising two or more target polynucleotides. The method comprises:

(a) providing a first polynucleotide in a first sample;

(b) providing a second polynucleotide in a second sample;

(c) coupling the first polynucleotide in the first sample to a membrane using one or more anchors;

(d) contacting the first polynucleotide with a pore as disclosed herein such that the polynucleotide moves with respect to, such as through, the pore;

(e) taking one or more measurements as the first polynucleotide moves with respect to the pore wherein the measurements are indicative of one or more characteristics of the first polynucleotide and thereby characterising the first polynucleotide;

(f) uncoupling the first polynucleotide from the membrane;

(g) coupling the second polynucleotide in the second sample to the membrane using one or more anchors;

(h) contacting the second polynucleotide with the pore as disclosed herein such that the second polynucleotide moves with respect to, such as through, the pore; and (i) taking one or more measurements as the second polynucleotide moves with respect to the pore wherein the measurements are indicative of one or more characteristics of the second polynucleotide and thereby characterising the second polynucleotide.

This type of method is discussed in detail in the UK Application No. 1406155.0.

Step (f) (i.e. uncoupling of the first polynucleotide) may be performed before step (g) (i.e. before coupling the second polynucleotide to the membrane). Step (g) may be performed before step (f). If the second polynucleotide is coupled to the membrane before the first polynucleotide is uncoupled, step (f) preferably comprises selectively uncoupling the first polynucleotide from the membrane (i.e. uncoupling the first polynucleotide but not the second polynucleotide from the membrane). A skilled person can design a system in which selective uncoupling is achieved. Steps (f) and (g) may be performed at the same time. This is discussed in more detail below.

In step (f), at least 10% of the first polynucleotide is preferably uncoupled from the membrane. For instance, at least 20%, at least 30%, at least 40%, at least 50%, at least 60%, at least 70%, at least 80%, at least 90% or at least 95% of the first polynucleotide may be uncoupled from the membrane. Preferably, all of the first polynucleotide is uncoupled from the membrane. The amount of the first polynucleotide uncoupled from the membrane can be determined using the pore. This is disclosed in the Examples.

The first polynucleotide and second polynucleotide may be different from one another. Alternatively, the first and second polynucleotides may be different polynucleotides. In such instances, there may be no need to remove at least part of the first sample before adding the second polynucleotide. This is discussed in more detail below. If the method concerns investigating three or more polynucleotides, they may all be different from one another or some of them may be different from one another.

The first polynucleotide and the second polynucleotide may be two instances of the same polynucleotide. The first polynucleotide may be identical to the second polynucleotide. This allows proof reading. If the method concerns investigating three or more polynucleotides, they may all be three or more instances of the same polynucleotide or some of them may be separate instances of the same polynucleotide.

The first sample and second sample may be different from one another. For instance, the first sample may be derived from a human and the second sample may be derived from a virus. If the first and second samples are different from one another, they may contain or be suspected of containing the same first and second polynucleotides. If the method concerns investigating three or more samples, they may all be different from one another or some of them may be different from one another.

The first sample and the second sample are preferably two instances of the same sample. The first sample is preferably identical to the second sample. This allows proof reading. If the method concerns investigating three or more samples, they may all be three or more instances of the same sample or some of them may be separate instances of the same sample.

Any number of polynucleotides can be investigated. For instance, the method may concern characterising 3, 4, 5, 6, 7, 8, 9, 10, 20, 30, 50, 100 or more polynucleotides. If three or more polynucleotides are investigated using the method, the second polynucleotide is also uncoupled from the membrane and the requisite number of steps are added for the third polynucleotide. The same is true for four or more polynucleotides.

The method involves uncoupling the first polynucleotide from the membrane. The method may involve uncoupling the second polynucleotide from the membrane if three or more polynucleotides are being investigated.

The first polynucleotide can be uncoupled from the membrane using any known method. The first polynucleotide is preferably not uncoupled from the membrane in step (f) using the transmembrane pore. The first polynucleotide is preferably not uncoupled from the membrane using a voltage or an applied potential.

Step (f) preferably comprises uncoupling the first polynucleotide from the membrane by removing the one or more anchors from the membrane. If the anchors are removed, the second polynucleotide is coupled to the membrane using other (or separate) anchors. The anchors used to couple the second polynucleotide may be the same type of anchors used to couple the first polynucleotide or different type of anchors.

Step (f) more preferably comprises contacting the one or more anchors with an agent which has a higher affinity for the one or more anchors than the anchors have for the membrane. A variety of protocols for competitive binding or immunoradiometric assays to determine the specific binding capability of molecules are well known in the art (see for example Maddox et al, J. Exp. Med. 158, 1211-1226, 1993). The agent removes the anchor(s) from the membrane and thereby uncouples the first polynucleotide. The agent is preferably a sugar. Any sugar which binds to the one or more anchors with a higher affinity than the one or more anchors have for the membrane may be used. The sugar may be a cyclodextrin or derivative thereof as discussed below.

If one or more anchors comprise a hydrophobic anchor, such as cholesterol, the agent is preferably a cyclodextrin or a derivative thereof or a lipid. The cyclodextrin or derivative thereof may be any of those disclosed in Eliseev, A. V., and Schneider, H-J. (1994) J. Am. Chem. Soc. 116, 6081-6088. The agent is more preferably heptakis-6-amino-β-cyclodextrin (am$_7$-βCD), 6-monodeoxy-6-monoamino-β-cyclodextrin (am$_1$-βCD) or heptakis-(6-deoxy-6-guanidino)-cyclodextrin (gu$_7$-PCD). Any of the lipids disclosed herein may be used.

If an anchor comprise(s) streptavidin, biotin or desthiobiotin, the agent is preferably biotin, desthiobiotin or streptavidin. Both biotin and desthiobiotin bind to streptavidin with a higher affinity than streptavidin binds to the membrane and vice versa. Biotin has a stronger affinity for streptavidin than desthiobiotin. An anchor comprising streptavidin may therefore be removed from the membrane using biotin or streptavidin and vice versa.

If an anchor comprises a protein, the agent is preferably an antibody or fragment thereof which specifically binds to the protein. An antibody specifically binds to a protein if it binds to the protein with preferential or high affinity, but does not bind or binds with only low affinity to other or different proteins. An antibody binds with preferential or high affinity if it binds with a Kd of $1\times10^{-6}$ M or less, more preferably $1\times10^{-7}$ M or less, $5\times10^{-8}$ M or less, more preferably $1\times10^{-8}$ M or less or more preferably $5\times10^{-9}$ M or less. An antibody binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more. Any method may be used to detect binding or specific binding. Methods of quantitatively measuring the binding of an antibody to a protein are well known in the art. The antibody may be a monoclonal antibody or a polyclonal antibody. Suitable fragments of antibodies include, but are not limited to, Fv, F(ab') and F(ab')$_2$ fragments, as well as single chain antibodies. Furthermore, the antibody or fragment thereof may be a chimeric antibody or fragment thereof, a CDR-grafted antibody or fragment thereof or a humanised antibody or fragment thereof.

Step (f) preferably comprises contacting the one or more anchors with an agent which reduces ability of the one or more anchors to couple to the membrane. For instance, the agent could interfere with the structure and/or hydrophobicity of the one or more anchors and thereby reduce their ability to couple to the membrane. If an anchor comprises cholesterol, the agent is preferably cholesterol dehydrogenase. If an anchor comprises a lipid, the agent is preferably a phospholipase. If an anchor comprises a protein, the agent is preferably a proteinase or urea. Other combination of suitable anchors and agents will be clear to a person skilled in the art.

Step (f) preferably comprises uncoupling the first polynucleotide from the membrane by separating the first polynucleotide from the one or more anchors. This can be done in any manner. For instance, the linker could be cut in an anchor comprising a linker. This embodiment is particularly applicable to anchors which involve linkage via hybridisation. Such anchors are discussed above.

Step (f) more preferably comprises uncoupling the first polynucleotide from the membrane by contacting the first polynucleotide and the one or more anchors with an agent which competes with the first polynucleotide for binding to one or more anchors. Methods for determining and measuring competitive binding are known in the art. The agent is preferably a polynucleotide which competes with the first polynucleotide for hybridisation to the one or more anchors. For instance, if the first polynucleotide is coupled to the membrane using one or more anchors which involve hybridisation, the polynucleotide can be uncoupled by contacting the one or more anchors with a polynucleotide which also hybridises to the site of hybridisation. The polynucleotide agent is typically added at a concentration that is higher than the concentration of the first polynucleotide and one or more anchors. Alternatively, the polynucleotide agent may hybridise more strongly to the one or more anchors than the first polynucleotide.

Step (f) more preferably comprises (i) contacting the first polynucleotide and the one or more anchors with urea, tris(2-carboxyethyl)phosphine (TCEP), dithiothreitol (DTT), streptavidin or biotin, UV light, an enzyme or a binding agent; (ii) heating the first polynucleotide and the one or more anchors; or (iii) altering the pH. Urea, tris(2-carboxyethyl)phosphine (TCEP) or dithiothreitol (DTT) are capable of disrupting anchors and separating the first polynucleotide from the membrane. If an anchor comprises a streptavidin-biotin link, then a streptavidin agent will compete for binding to the biotin. If an anchor comprises a streptavidin-desthiobiotin link, then a biotin agent will compete for binding to the streptavidin. UV light can be used to breakdown photolabile groups. Enzymes and binding agents can be used to cut, breakdown or unravel the anchor. Preferred enzymes include, but are not limited to, an exonuclease, an endonuclease or a helicase. Preferred binding agents include, but are not limited to, an enzyme, an antibody or a fragment thereof or a single-stranded binding protein (SSB). Any of the enzymes discussed below or antibodies discussed above may be used. Heat and pH can be used to disrupt hybridisation and other linkages.

If the first polynucleotide is uncoupled from the membrane by separating the first polynucleotide from the one or more anchors, the one or more anchors will remain in the membrane. Step (g) preferably comprises coupling the second polynucleotide to the membrane using the one or more anchors that was separated from the first polynucleotide. For instance, the second polynucleotide may also be provided with one or more polynucleotides which hybridise(s) to the one or more anchors that remain in the membrane. Alternatively, step (g) preferably comprises coupling the second polynucleotide to the membrane using one or more separate anchors from the ones separated from the first polynucleotide (i.e. one or more other anchors). The one or more separate anchors may be the same type of anchors used to couple the first polynucleotide to the membrane or may be different types of anchors. Step (g) preferably comprises coupling the second polynucleotide to the membrane using one or more different anchors from the one or more anchors separated from the first polynucleotide.

In a preferred embodiment, steps (f) and (g) comprise uncoupling the first polynucleotide from the membrane by contacting the membrane with the second polynucleotide such that the second polynucleotide competes with the first polynucleotide for binding to the one or more anchors and replaces the first polynucleotide. For instance, if the first polynucleotide is coupled to the membrane using one or more anchors which involve hybridisation, the first polynucleotide can be uncoupled by contacting the anchors with the second polynucleotide attached to polynucleotides which also hybridise to the sites of hybridisation in the one or more anchors. The second polynucleotide is typically added at a concentration that is higher than the concentration of the first polynucleotide and the one or more anchors. Alternatively, the second polynucleotide may hybridise more strongly to the one or more anchors than the first polynucleotide.

Removal or Washing

Although the first polynucleotide is uncoupled from the membrane in step (f), it is not necessarily removed or washed away. If the second polynucleotide can be easily distinguished from the first polynucleotide, there is no need to remove the first polynucleotide.

Between steps (f) and (g), the method preferably further comprises removing at least some of the first sample from the membrane. At least 10% of the first sample may be removed, such as at least 20%, at least 30%, at least 40%, at least 50%, at least 60%, at least 70%, at least 80% or at least 90% of the first sample may be removed.

The method more preferably further comprises removing all of the first sample from the membrane. This can be done in any way. For instance, the membrane can be washed with a buffer after the first polynucleotide has been uncoupled. Suitable buffers are discussed below.

Modified Polynucleotides

Before characterisation, a target polynucleotide may be modified by contacting the polynucleotide with a polymerase and a population of free nucleotides under conditions in which the polymerase forms a modified polynucleotide using the target polynucleotide as a template, wherein the polymerase replaces one or more of the nucleotide species in the target polynucleotide with a different nucleotide species when forming the modified polynucleotide. The modified polynucleotide may then be provided with one or more helicases attached to the polynucleotide and one or more molecular brakes attached to the polynucleotide. This type of modification is described in UK Application No. 1403096.9. Any of the polymerases discussed above may be used. The polymerase is preferably Klenow or 9o North.

The template polynucleotide is contacted with the polymerase under conditions in which the polymerase forms a modified polynucleotide using the template polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 9o North. A primer or a 3' hairpin is typically used as the nucleation point for polymerase extension.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the target polynucleotide with different nucleotide species in the modified polynucleotide, the modified polynucleotide contains k-mers which differ from those in the target polynucleotide. The different k-mers in the modified polynucleotide are capable of producing different current measurements from the k-mers in the target polynucleotide and so the modified polynucleotide provides different information from the target polynucleotide. The additional information from the modified polynucleotide can make it easier to characterise the target polynucleotide. In some instances, the modified polynucleotide itself may be easier to characterise. For instance, the modified polynucleotide may be designed to include k-mers with an increased separation or a clear separation between their current measurements or k-mers which have a decreased noise.

The polymerase preferably replaces two or more of the nucleotide species in the target polynucleotide with different nucleotide species when forming the modified polynucleotide. The polymerase may replace each of the two or more nucleotide species in the target polynucleotide with a distinct nucleotide species. The polymerase may replace each of the two or more nucleotide species in the target polynucleotide with the same nucleotide species.

If the target polynucleotide is DNA, the different nucleotide species in the modified typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the target polynucleotide is RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcyti-dine. The different nucleotide species may be any of the universal nucleotides discussed above.

The polymerase may replace the one or more nucleotide species with a different nucleotide species which comprises a chemical group or atom absent from the one or more nucleotide species. The chemical group may be a propynyl group, a thio group, an oxo group, a methyl group, a hydroxymethyl group, a formyl group, a carboxy group, a carbonyl group, a benzyl group, a propargyl group or a propargylamine group.

The polymerase may replace the one or more nucleotide species with a different nucleotide species which lacks a chemical group or atom present in the one or more nucleotide species. The polymerase may replace the one or more of the nucleotide species with a different nucleotide species having an altered electronegativity. The different nucleotide species having an altered electronegativity preferably comprises a halogen atom.

The method preferably further comprises selectively removing the nucleobases from the one or more different nucleotides species in the modified polynucleotide.

Analyte Delivery

The target analyte is preferably attached to a microparticle which delivers the analyte towards the membrane. This type of delivery is disclosed in UK Application No. 1418469.1. Any type of microparticle and attachment method may be used.

Other Characterisation Method

In another embodiment, a polynucleotide is characterised by detecting labelled species that are added to the target polynucleotide by a polymerase and then released. The polymerase uses the polynucleotide as a template. Each labelled species is specific for each nucleotide. The poly-nucleotide is contacted with a pore as disclosed herein, such as a double pore, a polymerase and labelled nucleotides such that phosphate labelled species are sequentially added to the polynucleotide by the polymerase, wherein the phosphate species contain a label specific for each nucleotide. The labelled species may be detected using the pore before they are released from the nucleotides (i.e. as they are added to the target polynucleotide) or after they are released from the nucleotides.

The polymerase may be any of those discussed above. The phosphate labelled species are detected using the pore and thereby characterising the polynucleotide. This type of method is disclosed in EP-A-2682460. Any of the embodiments discussed above equally apply to this method.

Examples of labelled species include, but are not limited to, polymers, polyethylene gycols, sugars, cyclodextrins, fluorophores, drugs, metabolites, peptides. A non-limiting example of such tags can be found in the work of Kumar et al. Sci Rep. 2012; 2:684. Epub 2012 Sep. 21.

Methods of Forming Sensors

Also provided is a method of forming a sensor for characterising a target polynucleotide. The method comprises forming a complex between a pore as disclosed herein and a polynucleotide binding protein, such as a helicase or an exonuclease. The complex may be formed by contacting the pore and the protein in the presence of the target polynucleotide and then applying a potential across the pore. The applied potential may be a chemical potential or a voltage potential as described above. Alternatively, the complex may be formed by covalently attaching the pore to the protein. Methods for covalent attachment are known in the art and disclosed, for example, in WO 2010/004265 and WO 2010/086603. The complex is a sensor for characterising the target polynucleotide. The method preferably comprises forming a complex between a pore as disclosed herein and a helicase. Any of the embodiments discussed above equally apply to this method.

Also provided is a sensor for characterising a target polynucleotide. The sensor comprises a complex between a pore as disclosed herein and a polynucleotide binding protein. Any of the embodiments discussed above equally apply to the sensor.

Kits

Also provided is a kit for characterising a target poly-nucleotide. The kit comprises a double pore and/or a pore as disclosed herein and the components of a membrane. The membrane is preferably formed from the components. The pore is preferably present in the membrane. The kit may comprise components of any of the membranes disclosed above, such as an amphiphilic layer or a triblock copolymer membrane.

The kit may further comprise a polynucleotide binding protein. Any of the polynucleotide binding proteins discussed above may be used.

The kit may further comprise one or more anchors for coupling the polynucleotide to the membrane.

The kit is preferably for characterising a double stranded polynucleotide and preferably comprises a Y adaptor and a hairpin loop adaptor. The Y adaptor preferably has one or more helicases attached and the hairpin loop adaptor preferably has one or more molecular brakes attached. The Y adaptor preferably comprises one or more first anchors for coupling the polynucleotide to the membrane, the hairpin loop adaptor preferably comprises one or more second anchors for coupling the polynucleotide to the membrane and the strength of coupling of the hairpin loop adaptor to the membrane is preferably greater than the strength of coupling of the Y adaptor to the membrane.

The kit may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides or voltage or patch clamp apparatus. Reagents may be present in the kit in a dry state such that a fluid sample resuspends the reagents. The kit may also, optionally, comprise instructions to enable the kit to be used in the method as disclosed herein or details regarding for which organism the method may be used.

Apparatus

Also provided is an apparatus for characterising a target analyte, such as a target polynucleotide. The apparatus comprises a plurality of the pores as disclosed herein and a plurality of membranes. The plurality of pores are preferably present in the plurality of membranes. The number of pores and membranes is preferably equal. Preferably, a single pore is present in each membrane.

The apparatus for characterising target analytes, may comprise or an array of pores as disclosed herein, for example an array of double pores, in a plurality of membranes.

The apparatus preferably further comprises instructions for carrying out the method. The apparatus may be any conventional apparatus for analyte analysis, such as an array or a chip. Any of the embodiments discussed above with reference to the methods are equally applicable to the apparatus of the invention. The apparatus may further comprise any of the features present in the kit as disclosed herein.

The apparatus is preferably set up to carry out a method as disclosed herein.

The apparatus preferably comprises:

a sensor device that is capable of supporting the plurality of pores and membranes and being operable to perform analyte characterisation using the pores and membranes; and at least one port for delivery of the material for performing the characterisation.

Alternatively, the apparatus preferably comprises:

a sensor device that is capable of supporting the plurality of pores and membranes being operable to perform analyte characterisation using the pores and membranes; and at least one reservoir for holding material for performing the characterisation.

The apparatus more preferably comprises:

a sensor device that is capable of supporting the membrane and plurality of pores and membranes and being operable to perform analyte characterising using the pores and membranes;

at least one reservoir for holding material for performing the characterising;

a fluidics system configured to controllably supply material from the at least one reservoir to the sensor device; and one or more containers for receiving respective samples, the fluidics system being configured to supply the samples selectively from one or more containers to the sensor device.

The apparatus may be any of those described in WO 2009/077734, WO 2010/122293, WO 2011/067559 or WO 00/28312.

Example 1: Double Pore Production

DNA (SEQ ID NO: 25) encoding the polypeptide Pro-CP1-Eco-(Mutant-StrepII(C)) (SEQ ID NO: 26) was cloned into a pT7 vector containing ampicillin resistance gene. Concentration of DNA solution was adjusted to 400 µg/uL. 1 µl of DNA was used to transform the cell line ONT001 which is Lemo BL21 DE3 cell line in which the gene coding for CsgG protein is replaced with DNA responsible for kanamycin resistance. Cells were then plated out on LB agar containing ampicillin (0.1 mg/ml) and kanamycin (0.03 mg/ml) and incubated for approximately 16 hours at 37° C.

Bacterial colonies grown on LB plates containing ampicillin and kanamycin can be assumed to have incorporated the CP1 plasmid with no endogenous production. One such colony was used to inoculate a starter culture of LB media (100 mL) containing both carbenicillin (0.1 mg/ml) and kanamycin (0.03 mg/ml). The starter culture was grown at 37° C. with agitation, until OD600 was reached to 1.0-1.2. The starter culture was used to inoculate a fresh 500 ml culture to and OD600 of 0.1. LB media containing the following additives—carbenicillin (0.1 mg/ml), kanamycin (0.03 mg/ml), 500 µM Rhamnose, 15 mM MgSO4 and 3 mM ATP. The culture was grown at 37° C. with agitation until stationary phase was entered and held for a further hour—stationary phase ascertained by plateau of measured OD600. Temperature of the culture was then adjusted to 18° C. and glucose was added to a final concentration of 0.2%. Once culture was stable at 18° C. induction was initiated by the addition of lactose to a final concentration of 1%. Induction was carried out for approximately 18 hours with agitation at 18° C.

Following induction, the culture was pelleted by centrifugation at 6,000 g for 30 minutes. The pellet was resuspended in 50 mM Tris, 300 mM NaCl, containing Protease Inhibitors (Merck Millipore 539138), Benzonase Nuclease (Sigma E1014),1× Bugbuster (Merck Millipore 70921) and 0.1% Brij 58 pH8.0 (approximately 10 ml of buffer per gram of pellet). The suspension was mixed well until it is fully homogeneous, sample was then transferred to roller mixer at 4° C. for approximately 5 hours. Lysate was pelleted by centrifugation at 20,000 g for 45 minutes and the supernatant was filtered through 0.22 µM PES syringe filter. Supernatant which contains CP1 was taken forward for purification by column chromatography.

Sample was applied to a 5 ml Strep Trap column (GE Healthcare). Column was washed with 25 mM Tris, 150 mM NaCl, 2 mM EDTA, 0.1% Brij 58 pH8 until a stable baseline of 10 column volumes was maintained. Column was then washed with 25 mM Tris, 2M NaCl, 2 mM EDTA, 0.1% Brij 58 pH8 before being returned to 150 mM buffer. Elution was carried out with 10 mM desthiobiotin. Elution peak was pooled and carried forward for ion exchange purification on a 1 ml Q HP column (GE Healthcare) using 25 mM Tris, 150 mM NaCl, 2 mM EDTA, 0.1% Brij 58 pH8 as the binding buffer and 25 mM Tris, 500 mM NaCl, 2 mM EDTA, 0.1% Brij 58 pH8 as the elution buffer. Flowthrough peak was observed to contain both dimer and monomer protein, elution peak at approx. 400 ms/see was observed to contain monomeric pore. Flowthrough peak was concentrated via vivaspin column (100 kd MWCO) and carried forward for size exclusion chromatography on 24 ml S200 increase column (GE Healthcare) with the buffer 25 mM Tris, 150 mM NaCl, 2 mM EDTA, 0.1% Brij 58, 0.1% SDS pH8. Dimeric (double) pore eluted at 9 ml while the monomeric pore eluted at 10.5 ml.

Example 2: Elongation of the Constriction (Read Head) in a CsgG Pore

Materials and Methods

Electrical measurements were acquired from a variety of single CsgG nanopores inserted in block co-polymer in buffer (25 mM K Phosphate buffer, 150 mM Potassium Ferrocyanide(II), 150 mM Potassium Ferricyanide(III), pH 8.0). After achieving a single pore inserted in the block co-polymer, buffer (1 mL 25 mM K Phosphate buffer, 150 mM Potassium Ferrocyanide(II), 150 mM Potassium Ferricyanide(III), pH 8.0) was flowed through the system to remove any excess CsgG nanopores. A platform QC was then run to determine the number of channels containing single nanopores. To do this 1 mL of buffer (25 mM K Phosphate buffer, 150 mM Potassium Ferrocyanide(II), 150 mM Potassium Ferricyanide(III), pH 8.0) containing 240 nM TBA was flown through the inlet. Whilst platform QC was in progress, RBF1 (940 mM KCL, 50 mM HEPES, 20 mM MgCl2 and 22 mM ATP) was diluted to 1× using nuclease free water. 800 µl of 1×RBF1 was then flushed through the inlet. After 10 minutes the SpotON valve was opened and 200 µL of 1×RBF1 was flown through the inlet. The system was now ready for sequencing.

Meanwhile, DNA sample was prepared for sequencing using the following method: 1 µg of DNA analyte was incubated with the 40 nM of adapter mix (containing a T4 Dda helicase enzyme prebound to the adapter) and blunt TA ligase for 10 minutes. The ligation mixture was then purified to remove unligated free adapter using Spri purification. The final ligated mixture was eluted in 25 µL elution buffer containing 40 mM CAPS at pH10, 40 mM KCl and 400 nM cholesterol tether. For each chip, 1241 of DNA-adpater ligated mix was mixed with 37.5 µL RBF1 and 25.5 µL water (final volume of 75 µL) and added to Flow Cell via the SpotON port for sequencing. The experiment was then run for 6 hours at −180 mV.

Results

A list of squiggles was assembled for each pore mutant, and using these squiggles a Hidden Markov Model (HMM) model was made that describes the signal characteristics of all sequence contexts observed in the DNA analyte. Using these models, we were able to gain insight into the length and shape of the read head. The left-hand plots in FIGS. 6 to 9 show the current levels versus read head position grouped by base. For example, at read head position 3, the median current of all sequence contexts with either an A or C or G or T at the $3^{rd}$ position are averaged. The right-hand plots in FIGS. 6 to 9 show discrimination versus read head position, where discrimination is defined as the variance in the current attributable to variation in the base at that position, averaged over all sequence contexts.

Figure 6A:
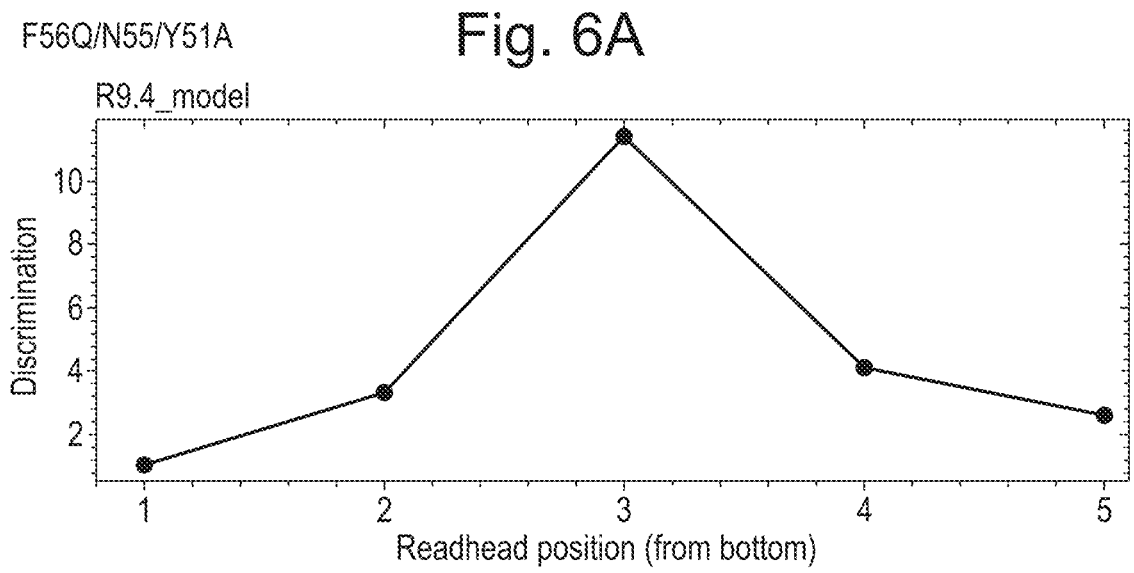
FIGS. 6A-6C show results obtained with the sharpened reader head of a baseline pore comprising monomers having the sequence shown in SEQ ID NO: 2 in which the following substitutions have been made: Y51A; F56Q; K94Q; R97W; and R192D, and in which V105 to I107 have been deleted. The Y51A and F56Q sharpen the reader head.
Figure 6B:
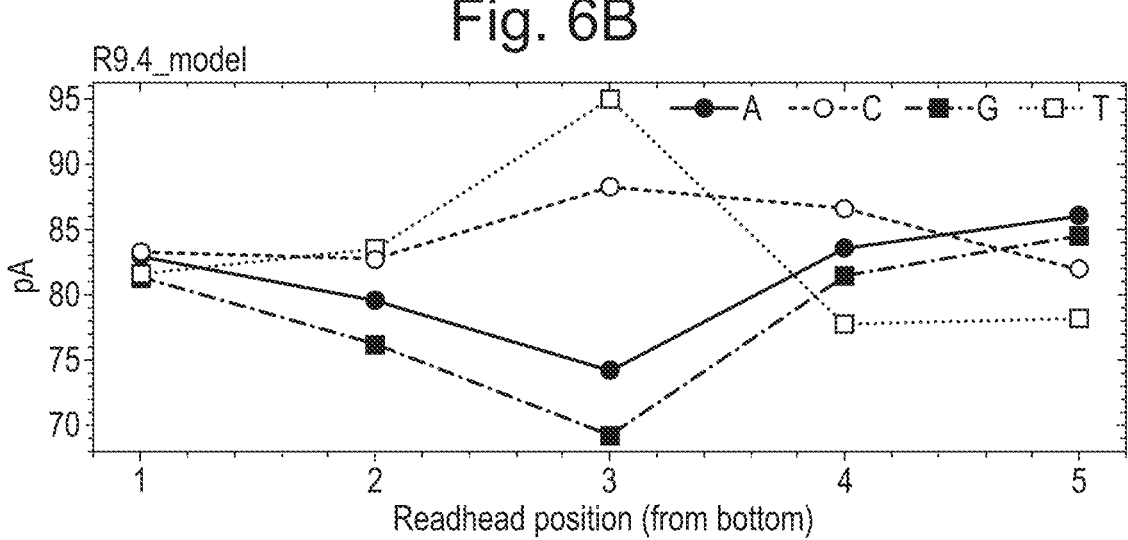
Figure 6C:
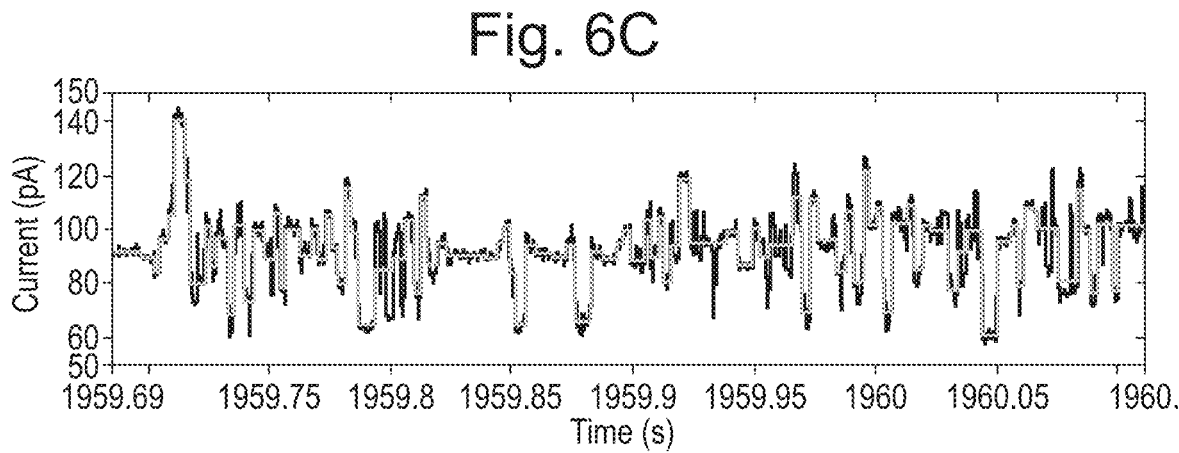
Figure 7A:
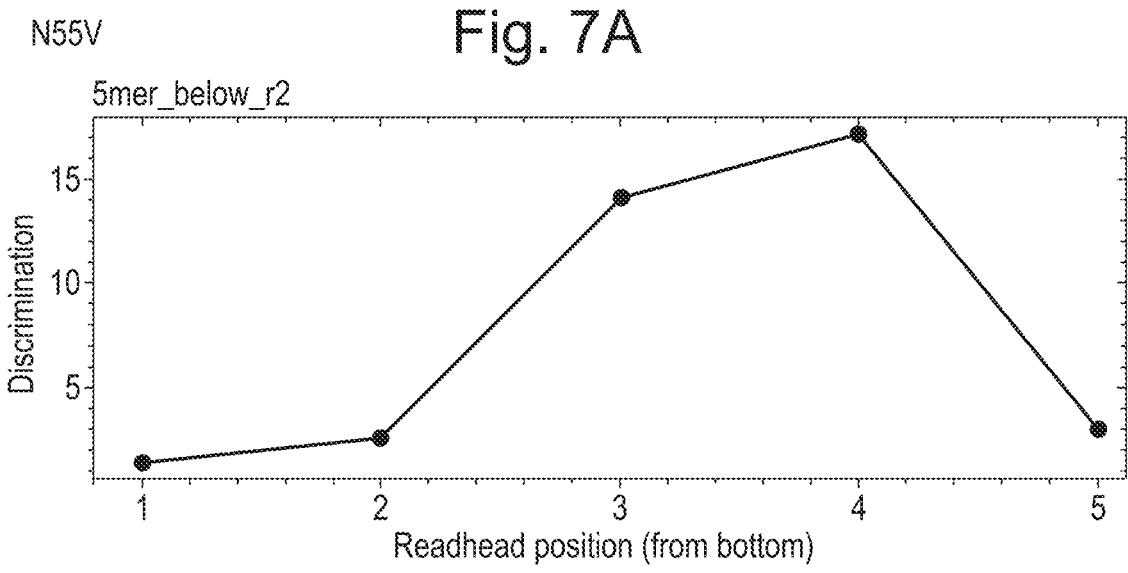
FIGS. 7A-7C show results obtained with the broader reader head of the baseline pore containing an additional N55V substitution.
Figure 7B:
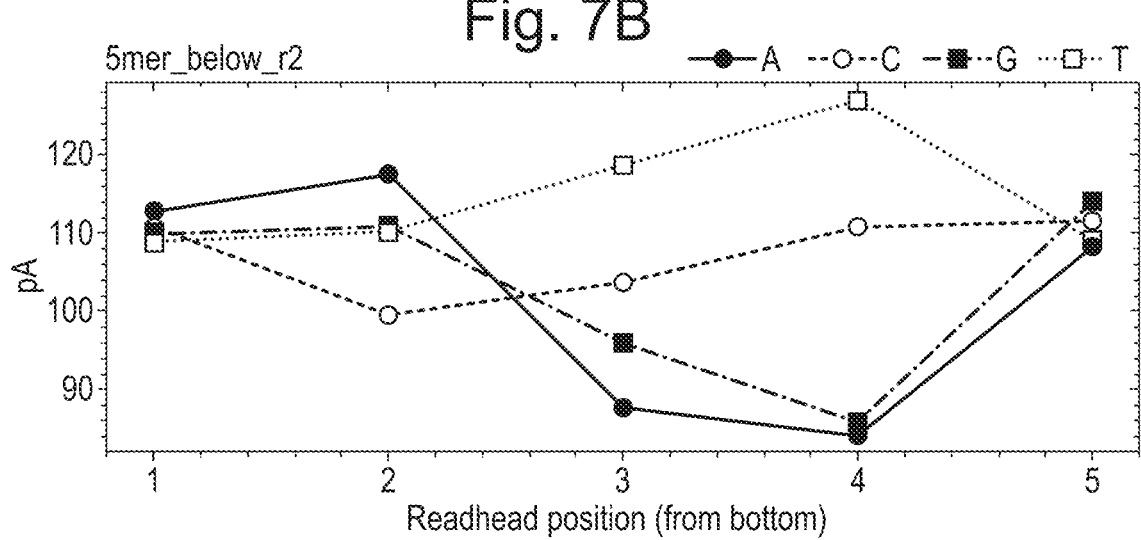
Figure 7C:
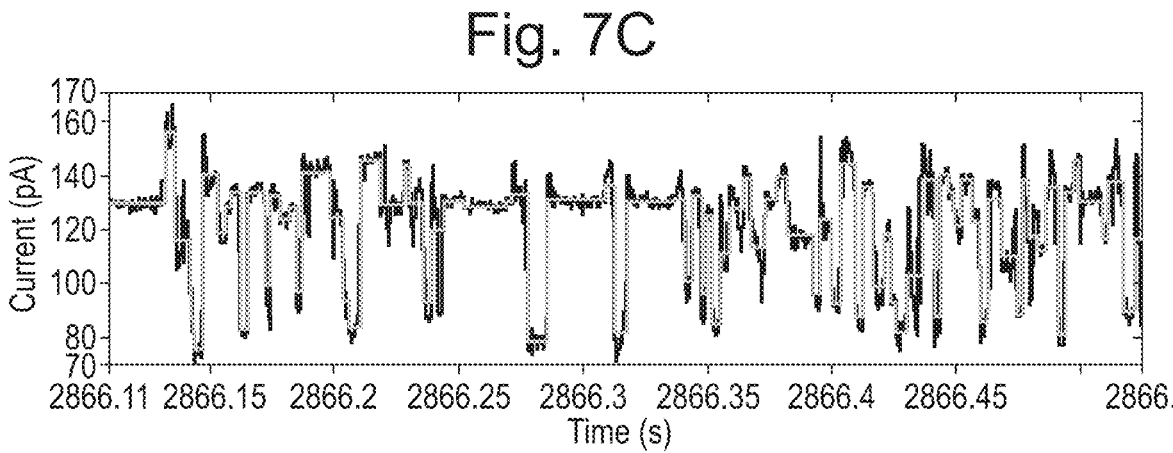
Figure 8A:
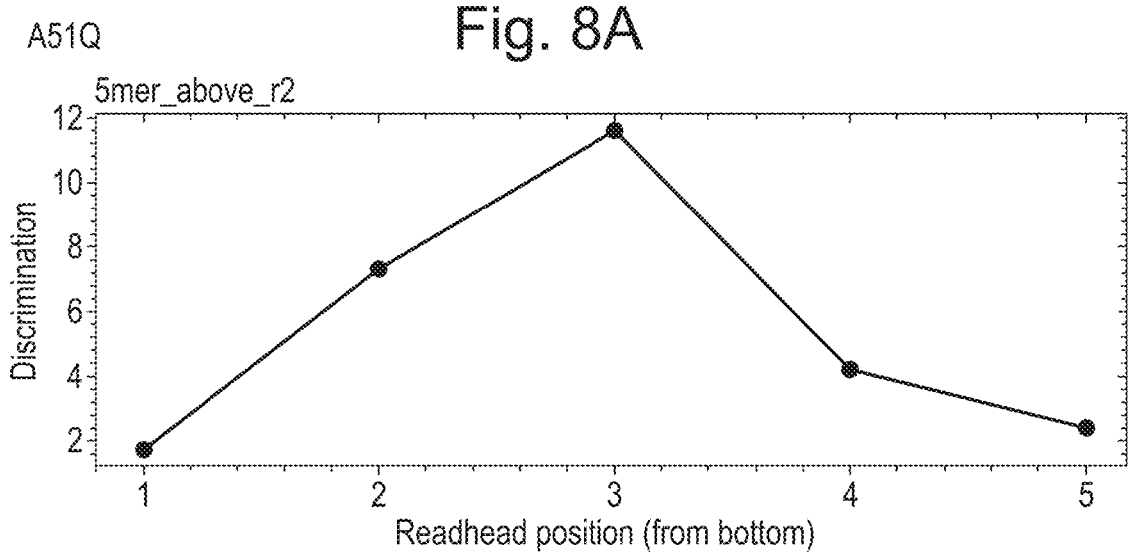
FIGS. 8A-8C show results obtained with the broader reader head of the baseline pore containing an A51Q substitution.
Figure 8B:
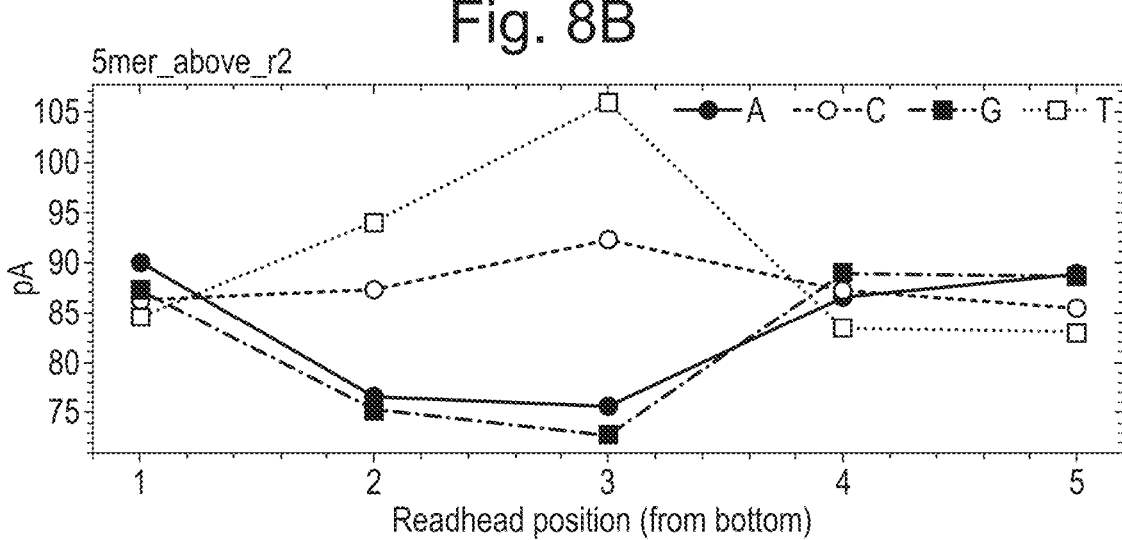
Figure 8C:
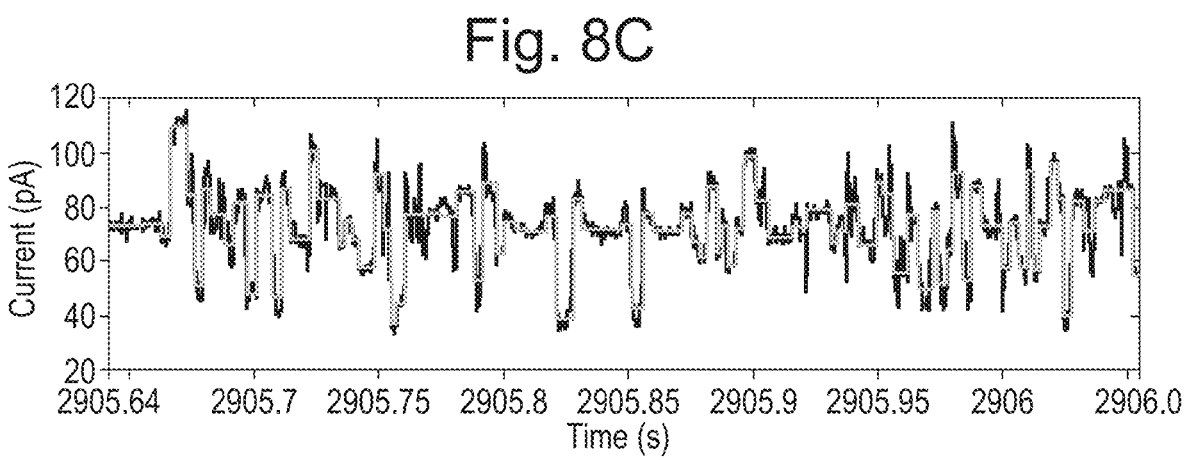
Figure 9A:
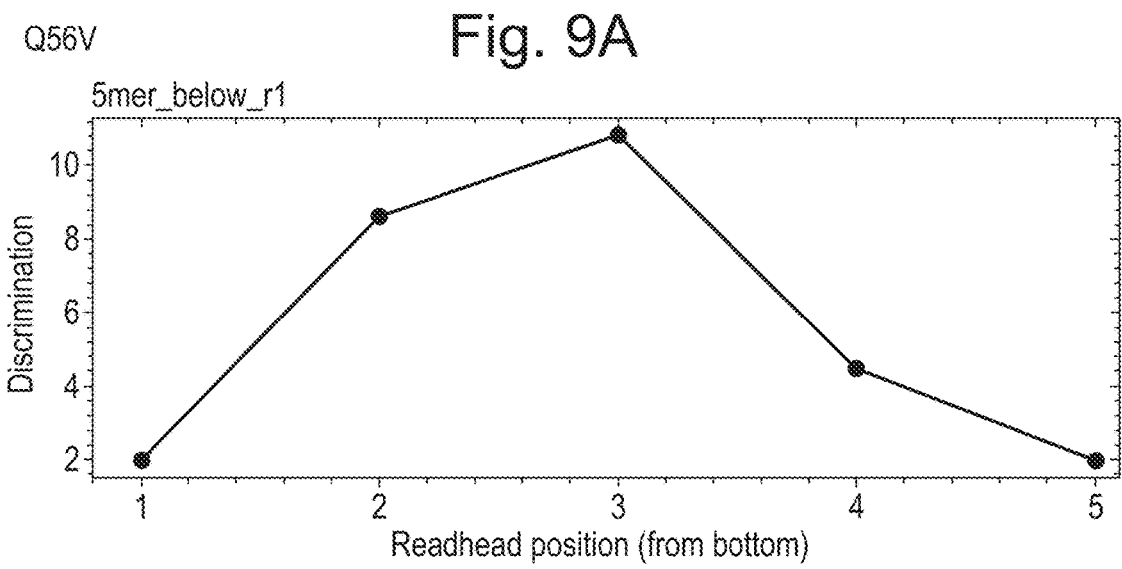
FIGS. 9A-9C show results obtained with the broader reader head of the baseline pore containing a Q56V substitution.
Figure 9B:
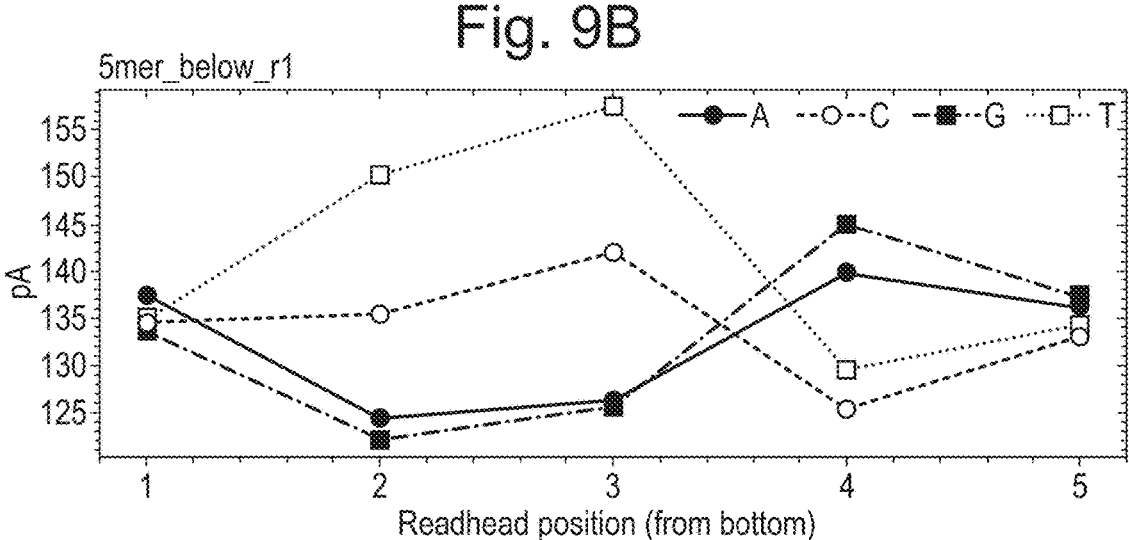
Figure 9C:
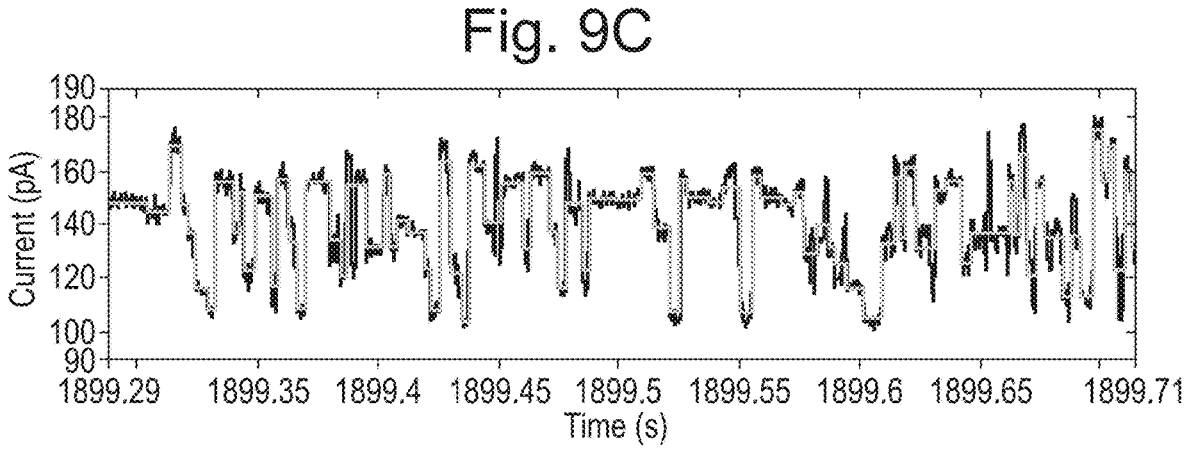
Figure 10A:
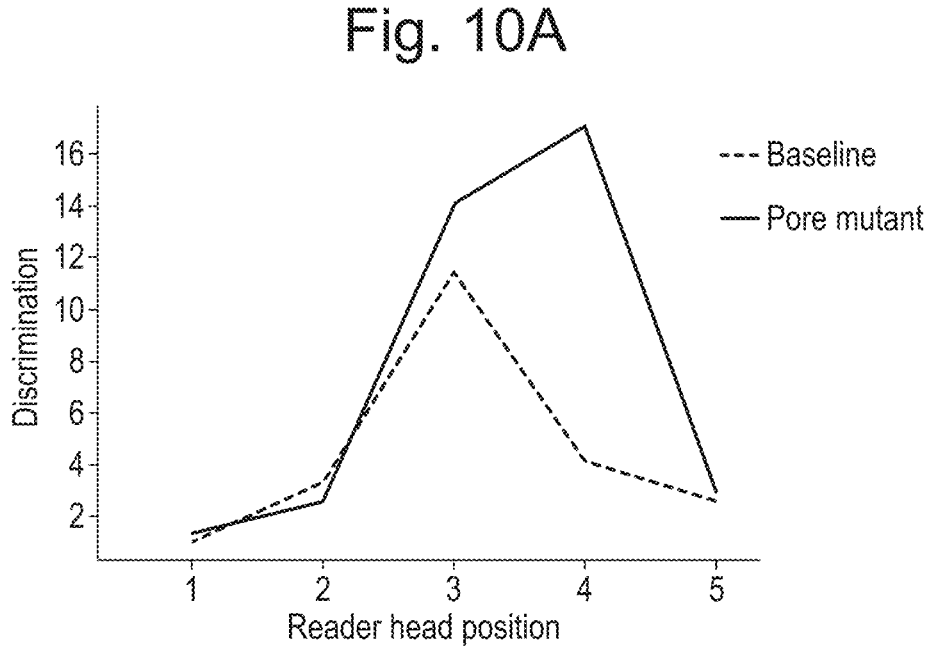
FIG. 10A is a comparison of the discrimination of bases against the reader head position between the baseline pore (FIGS. 6A-6C) and the N55V pore (FIGS. 7A-7C).
Figure 10B:
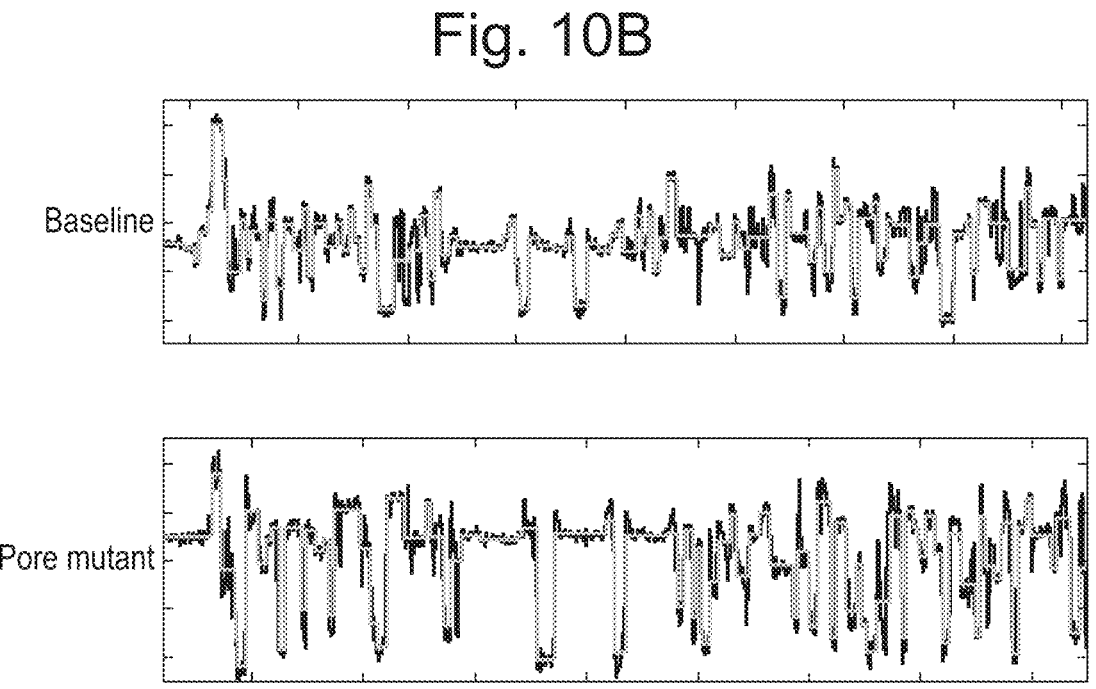
FIG. 10B is a comparison of the example squiggles produced using the baseline pore (FIGS. 6A-6C) and the N55V pore (FIGS. 7A-7C) and shows that mutants give different squiggles to baseline.
Figure 11C:
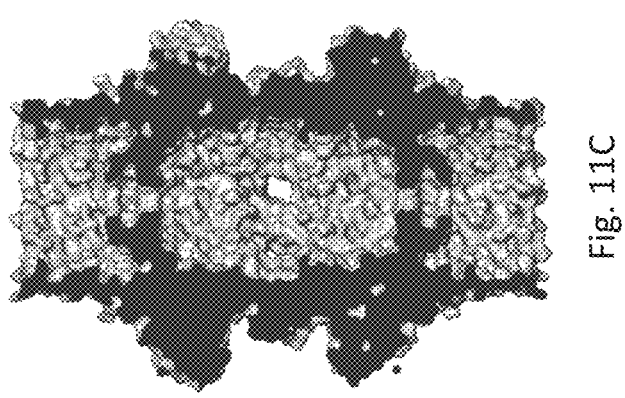
FIGS. 11A-11C show the structures and reader heads of the baseline CsgG pore used in the Examples (FIG. 11A), a CsgG pore with an elongated reader head (FIG. 11B) and a double CsgG pore (FIG. 11C). Homopolymer basecalling is improved compared to the baseline when the elongated reader head pore or the double pore is used.
Figure 11B:
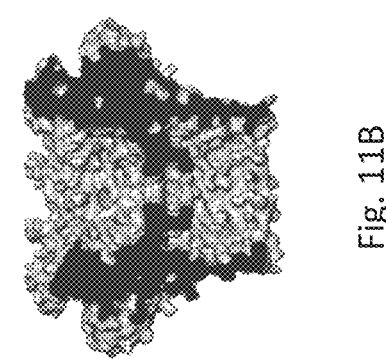
Figure 11A:
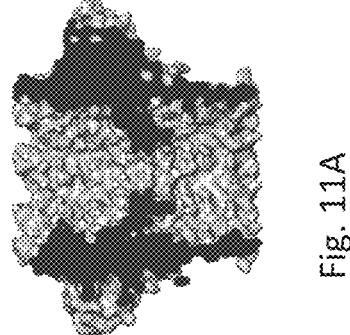
Figure 12A:
FIGS. 12A-12B show sequence alignments of the 21 CsgG homologues having the amino acid sequences shown in SEQ ID Nos 2 to 7 and 9 to 23. The C-terminal serine (S) of each of SEQ ID NOs: 2, 3, 5, 6, 7, 9 and 10 is not included in the alignment.
Figure 12B:
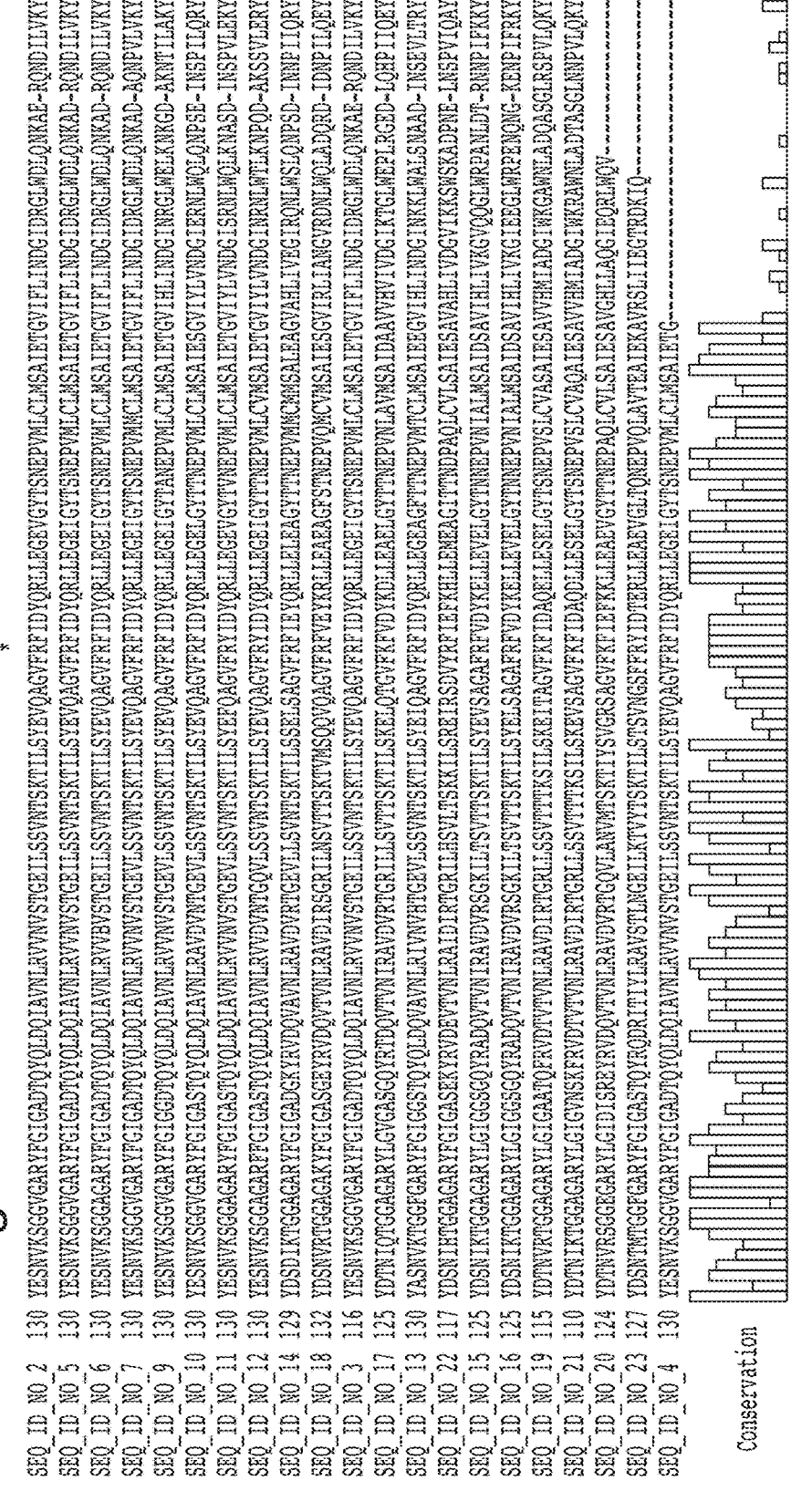
Figure 13A:
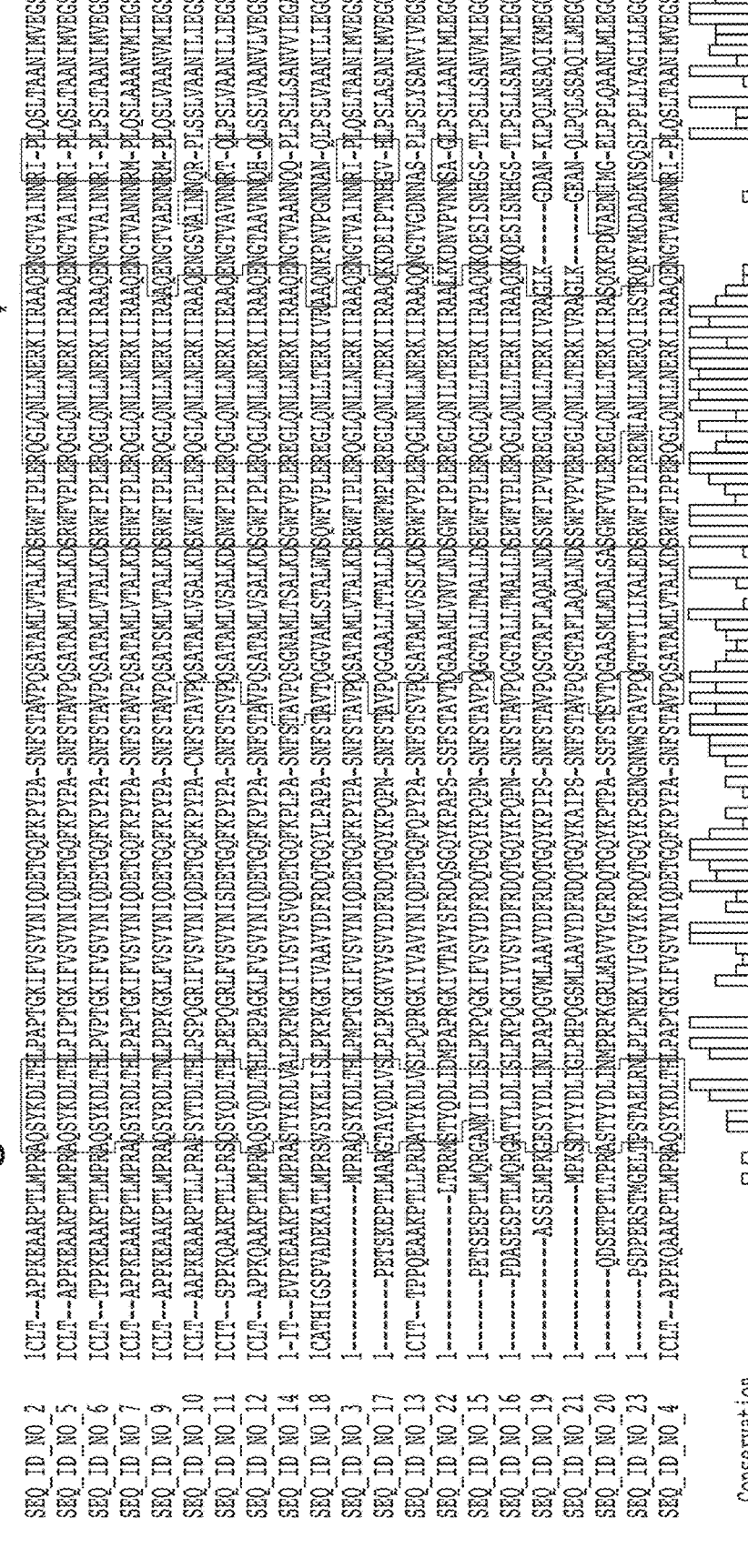
FIGS. 13A-13B show the same relative sequence alignments as FIGS. 12A-12B with predicted alpha helical secondary structure regions additionally shaded.
Figure 13B:
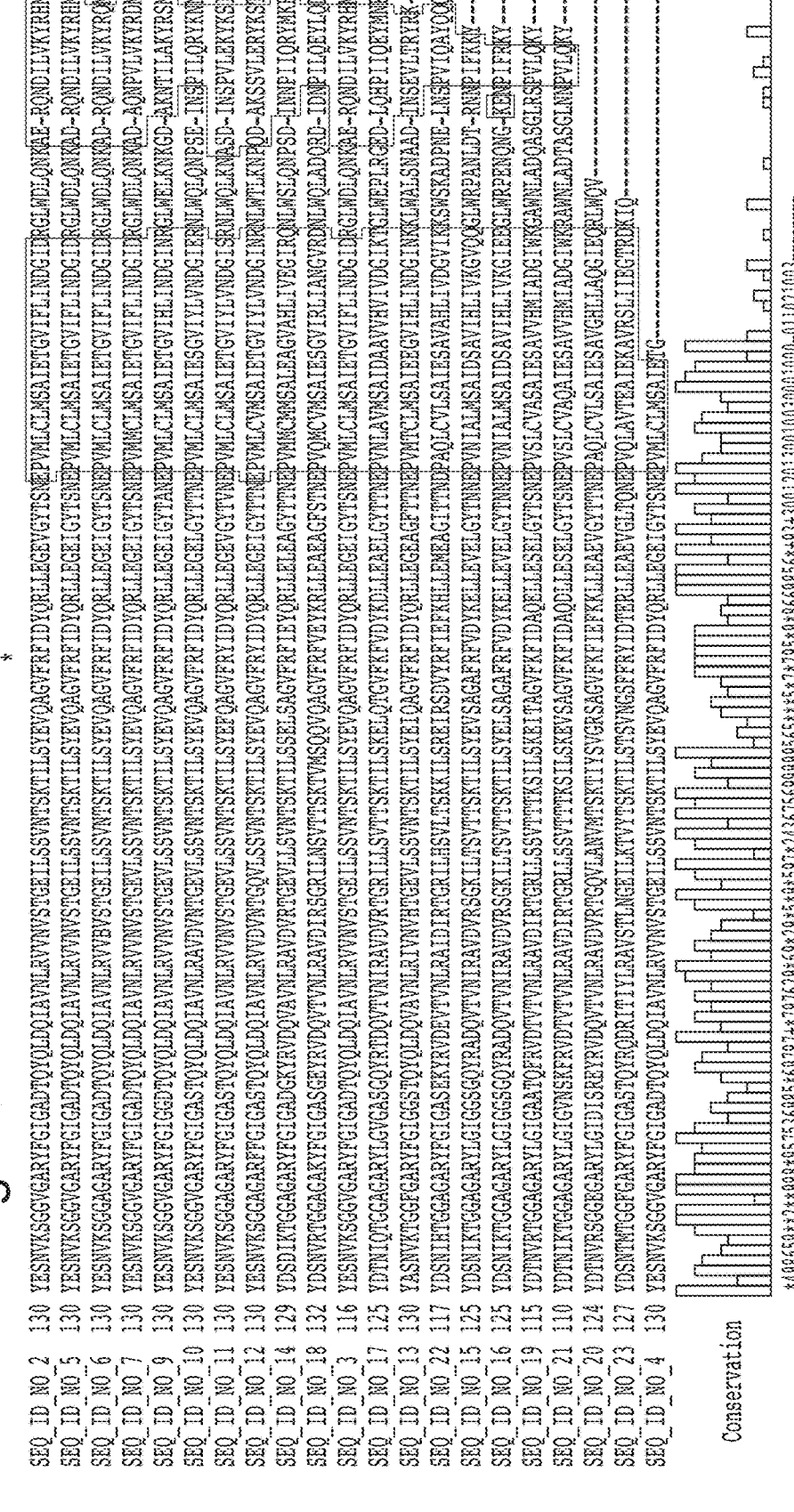
Figure 14A:
FIGS. 14A-14B shows the same relative sequence alignments as FIGS. 12A-12B with predicted beta sheet secondary structure regions additionally shaded.
Figure 14A:
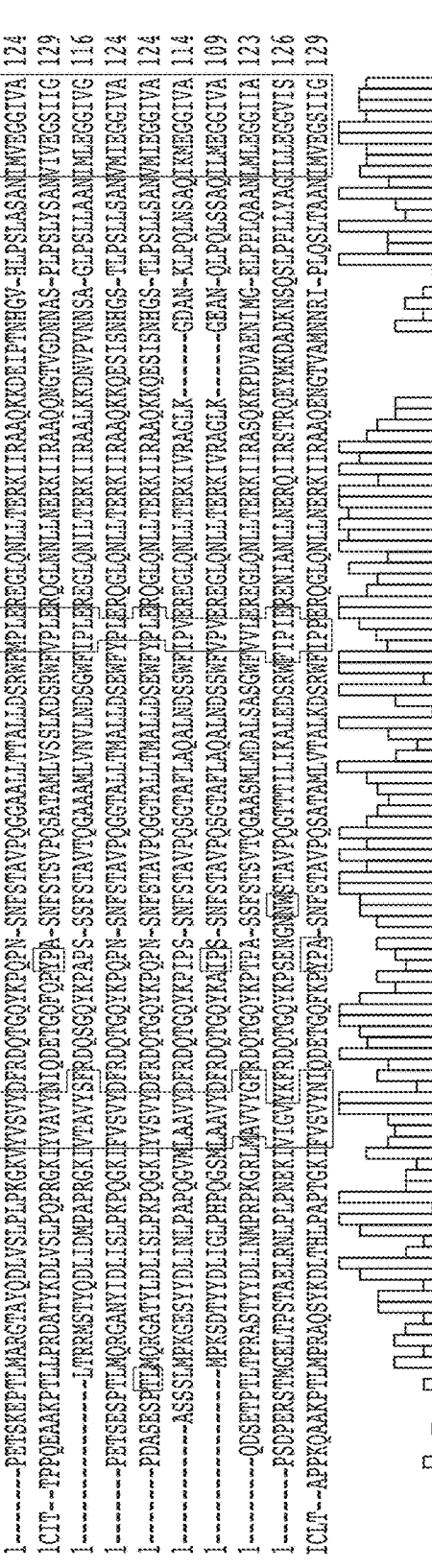
Figure 14B:

FIG. 6 shows the discrimination profile for a baseline pore comprising monomers having the sequence shown in SEQ ID NO: 2 in which the following substitutions have been made: Y51A; F56Q; K94Q; R97W; and R192D, and in which V105 to 1107 have been deleted. This pore has one dominant position in the read head at the $3^{rd}$ position when 5 bases are present in the pore read head at a given time. FIGS. 7 to 9 show the discrimination profile for pores comprising the above baseline pore mutations in SEQ ID NO: 2 and one of the following additional substitutions: N55V, A51Q and Q56V. These mutants all demonstrate an elongation of the read head compared to the baseline pore, with two positions in the read head now contributing to the signal.

The invention claimed is:

1. A transmembrane double pore forming a channel through a membrane, comprising a first CsgG pore, or a homologue thereof, whose tail is associated with the tail of a second CsgG pore, or a homologue thereof, wherein:

(i) the first CsgG pore, or homologue thereof, is a homooligomer and the second CsgG pore, or homologue thereof, is a homooligomer, and the first CsgG pore, or homologue thereof, comprises monomers that have a different amino acid sequence from the monomers of which the second CsgG pore, or homologue thereof, is comprised;

(ii) the first CsgG pore, or homologue thereof, is a homooligomer and the second CsgG pore, or homologue thereof, is a homooligomer, and the first CsgG pore, or homologue thereof, and/or the second CsgG pore, or homologue thereof is not a wild-type pore;

(iii) the first CsgG pore, or homologue thereof, is a heterooligomer and the second CsgG pore, or homologue thereof, is a homooligomer;

(iv) the first CsgG pore, or homologue thereof, is a homooligomer and the second CsgG pore, or homologue thereof, is a heterooligomer; or (v) the first CsgG pore, or homologue thereof, is a heterooligomer and the second CsgG pore, or homologue thereof, is a heterooligomer, and wherein at least one residue at the interface between the first CsgG pore, or homologue thereof, and the second CsgG pore, or homologue thereof, is bulkier than the residue present at the corresponding position in a wild type CsgG pore monomer.

2. The transmembrane double pore according to claim 1, wherein the first CsgG pore, or homologue thereof, and the second CsgG pore, or homologue thereof are identical.

3. The transmembrane double pore according to claim 1, wherein the first CsgG pore, or homologue thereof, and the second CsgG pore, or homologue thereof, are different.

4. The transmembrane double pore according to claim 1, wherein the first CsgG pore, or homologue thereof, is attached to the second CsgG pore, or homologue thereof, by hydrophobic interactions and/or by one or more disulphide bond.

5. The transmembrane double pore according to claim 4, wherein at least one monomer in the first CsgG pore, or homologue thereof, and/or at least one monomer in the second CsgG pore, or homologue thereof, comprises at least one cysteine residue at the interface between the first and second pores, which cysteine residue is not present in the wild type CsgG monomer, or the wild type CsgG homologue monomer.

6. The transmembrane double pore according to claim 4, wherein at least one monomer in the first CsgG pore, or homologue thereof, and/or at least one monomer in the second CsgG pore, or homologue thereof, comprises at least one residue at the interface between the first and second pores, which residue is more hydrophobic than the residue present at the corresponding position in the wild type CsgG monomer, or the wild type CsgG homologue monomer.

7. The transmembrane double pore according to claim 1, wherein at least one monomer in the first CsgG pore, or homologue thereof, and/or at least one monomer in the second CsgG pore, or homologue thereof, comprises at least one residue in the barrel region of the pore, which residue has less negative charge than the residue present at the corresponding position in the wild type CsgG monomer, or the wild type CsgG homologue monomer.

8. The transmembrane double pore according to claim 1, wherein at least one monomer in the first CsgG pore, or homologue thereof, comprises at least one residue in the constriction of the barrel region of the first pore, which residue decreases, maintains or increases the length of the constriction compared to the wild type CsgG pore, or the wild type CsgG homologue pore, and/or at least one monomer in the second CsgG pore, or homologue thereof, comprises at least one residue in the constriction of the barrel region of the second pore, which residue decreases, maintains or increases the length of the constriction compared to the wild type CsgG pore, or the wild type CsgG homologue pore.

9. The transmembrane double pore according to claim 8, wherein the at least one residue in the constriction of the barrel region of the pore is a residue that is additional to the residues present in the constriction of the wild type CsgG pore, or the wild type CsgG homologue pore.

10. The transmembrane double pore according to claim 9, wherein the at least one residue is S, G, SG, SGG, SGS, GS, GSS and/or GSG.

11. A method for determining the presence, absence or one or more characteristics of a target analyte, comprising:

(a) contacting the target analyte with the transmembrane double pore according to claim 1 such that the target analyte moves with respect to the transmembrane double pore; and (b) taking one or more measurements as the analyte moves with respect to the transmembrane double pore and thereby determining the presence, absence or one or more characteristics of the analyte.

12. A kit for characterising a target analyte comprising (a) the transmembrane double pore according to claim 1 and (b) the components of a membrane.

13. An apparatus for characterising target analytes in a sample, comprising an array of transmembrane double pores according to claim 1 in a plurality of membranes.

14. The transmembrane double pore of claim 1, the at least one residue at the interface between the first CsgG pore, or homologue thereof, and the second CsgG pore, or homologue thereof, is at a position corresponding to A98, A99, T104, V105, L113, Q114 or S115 of SEQ ID NO: 2.

15. The transmembrane double pore of claim 14, wherein the at least one residue at the interface between the first CsgG pore, or homologue thereof, and the second CsgG pore, or homologue thereof is:

(i) I, L, V, M, F, W, Y, N, Q, S or T where the residue present at the corresponding position in the wild type CsgG monomer, or the wild type CsgG homologue monomer is A;

(ii) L, M, F, W, Y, N, Q, R, D or E where the residue present at the corresponding position in the wild type CsgG monomer, or the wild type CsgG homologue monomer is T;

(iii) I, L, M, F, W, Y, N, Q where the residue present at the corresponding position in the wild type CsgG monomer, or the wild type CsgG homologue monomer is V;

(iv) M, F, W, Y, N, Q, R, D or E where the residue present at the corresponding position in the wild type CsgG monomer, or the wild type CsgG homologue monomer is L;

(v) F, W, Y where the residue present at the corresponding position in the wild type CsgG monomer, or the wild type CsgG homologue monomer is Q; and/or (vi) M, F, W, Y, N, Q, E or R where the residue present at the corresponding position in the wild type CsgG monomer, or the wild type CsgG homologue monomer is S.

\* \* \* \* \*

```
                        SEQUENCE LISTING

Sequence total quantity: 26
SEQ ID NO: 1            moltype = DNA   length = 786
FEATURE                Location/Qualifiers
source                 1..786
                       mol_type = genomic DNA
                       organism = Escherichia coli
SEQUENCE: 1
tgtctgaccg caccgccgaa agaagcggca cgtccgaccc tgatgccgcg tgcacagtct   60
tataaagatc tgacccatct gccggctccg acgggcaaga tttttgttag cgtctataac  120
atccaggacg aaaccggtca atttaaaccg tacccggcga gtaatttctc cacggccgtt  180
ccgcagagtg caaccgctat gctggtcacg gcactgaaag attcccgttg gttcattccg  240
ctggaacgcc agggcctgca aaacctgctg aatgaacgta aaattatccg cgcagctcag  300
gaaaacggta ccgtggccat taacaatcgt attccgctgc aaagcctgac cgccgcaaac  360
atcatggttg aaggctctat catcggttac gaatcaaacg tcaaatcggg cggtgtgggc  420
gcacgttatt ttggcattgg tgctgatacc cagtaccaac tggaccagat cgcagttaac  480
ctgcgcgtgg ttaatgtcag caccggcgaa attctgagct ctgtgaatac cagcaaaacg  540
atcctgtctt acgaagtgca ggctggtgtt tttcgtttca ttgattatca acgcctgctg  600
gaaggcgaag tcggttacac ctcaaacgaa ccggtgatgc tgtgtctgat gtcggcgatt  660
gaaacggggtg ttattttcct gatcaatgat ggcatcgacc gtggtctgtg ggatctgcag  720
aacaaagccg aacgtcaaaa tgacattctg gtgaaatacc gccacatgag tgttccgccg  780
gaatcc                                                            786

SEQ ID NO: 2            moltype = AA   length = 262
FEATURE                Location/Qualifiers
source                 1..262
                       mol_type = protein
                       organism = Escherichia coli
SEQUENCE: 2
CLTAPPKEAA RPTLMPRAQS YKDLTHLPAP TGKIFVSVYN IQDETGQFKP YPASNFSTAV   60
PQSATAMLVT ALKDSRWFIP LERQGLQNLL NERKIIRAAQ ENGTVAINNR IPLQSLTAAN  120
IMVEGSIIGY ESNVKSGGVG ARYFGIGADT QYQLDQIAVN LRVVNVSTGE ILSSVNTSKT  180
ILSYEVQAGV FRFIDYQRLL EGEVGYTSNE PVMLCLMSAI ETGVIFLIND GIDRGLWDLQ  240
NKAERQNDIL VKYRHMSVPP ES                                           262

SEQ ID NO: 3            moltype = AA   length = 248
FEATURE                Location/Qualifiers
source                 1..248
                       mol_type = protein
                       organism = Citrobacter koseri
SEQUENCE: 3
MPRAQSYKDL THLPMPTGKI FVSVYNIQDE TGQFKPYPAS NFSTAVPQSA TAMLVTALKD   60
SRWFIPLERQ GLQNLLNERK IIRAAQENGT VAINNRIPLQ SLTAANIMVE GSIIGYESNV  120
KSGGVGARYF GIGADTQYQL DQIAVNLRVV NVSTGEILSS VNTSKTILSY EVQAGVFRFI  180
DYQRLLEGEI GYTSNEPVML CLMSAIETGV IFLINDGIDR GLWDLQNKAE RQNDILVKYR  240
HMSVPPES                                                           248

SEQ ID NO: 4            moltype = AA   length = 223
FEATURE                Location/Qualifiers
source                 1..223
                       mol_type = protein
                       organism = Salmonella enterica
SEQUENCE: 4
CLTAPPKQAA KPTLMPRAQS YKDLTHLPAP TGKIFVSVYN IQDETGQFKP YPASNFSTAV   60
```

```
PQSATAMLVT ALKDSRWFIP LERQGLQNLL NERKIIRAAQ ENGTVAMNNR IPLQSLTAAN   120
IMVEGSIIGY ESNVKSGGVG ARYFGIGADT QYQLDQIAVN LRVVNVSTGE ILSSVNTSKT   180
ILSYEVQAGV FRFIDYQRLL EGEIGYTSNE PVMLCLMSAI ETG                     223

SEQ ID NO: 5            moltype = AA  length = 262
FEATURE                 Location/Qualifiers
source                  1..262
                        mol_type = protein
                        organism = Citrobacter amalonaticus
SEQUENCE: 5
CLTAPPKEAA KPTLMPRAQS YKDLTHLPIP TGKIFVSVYN IQDETGQFKP YPASNFSTAV   60
PQSATAMLVT ALKDSRWFVP LERQGLQNLL NERKIIRAAQ ENGTVAINNR IPLQSLTAAN   120
IMVEGSIIGY ESNVKSGGVG ARYFGIGADT QYQLDQIAVN LRVVNVSTGE ILSSVNTSKT   180
ILSYEVQAGV FRFIDYQRLL EGEIGYTSNE PVMLCLMSAI ETGVIFLIND GIDRGLWDLQ   240
NKADRQNDIL VKYRHMSVPP ES                                            262

SEQ ID NO: 6            moltype = AA  length = 262
FEATURE                 Location/Qualifiers
source                  1..262
                        mol_type = protein
                        organism = Citrobacter rodentium
SEQUENCE: 6
CLTTPPKEAA KPTLMPRAQS YKDLTHLPVP TGKIFVSVYN IQDETGQFKP YPASNFSTAV   60
PQSATAMLVT ALKDSRWFIP LERQGLQNLL NERKIIRAAQ ENGTVAINNR IPLPSLTAAN   120
IMVEGSIIGY ESNVKSGGAG ARYFGIGADT QYQLDQIAVN LRVVNVSTGE ILSSVNTSKT   180
ILSYEVQAGV FRFIDYQRLL EGEIGYTSNE PVMLCLMSAI ETGVIFLIND GIDRGLWDLQ   240
NKADRQNDIL VKYRQMSVPP ES                                            262

SEQ ID NO: 7            moltype = AA  length = 262
FEATURE                 Location/Qualifiers
source                  1..262
                        mol_type = protein
                        organism = Enterobacter asburiae
SEQUENCE: 7
CLTAPPKEAA KPTLMPRAQS YRDLTHLPAP TGKIFVSVYN IQDETGQFKP YPASNFSTAV   60
PQSATAMLVT ALKDSHWFIP LERQGLQNLL NERKIIRAAQ ENGTVANNNR MPLQSLAAAN   120
VMIEGSIIGY ESNVKSGGVG ARYFGIGADT QYQLDQIAVN LRVVNVSTGE VLSSVNTSKT   180
ILSYEVQAGV FRFIDYQRLL EGEIGYTSNE PVMMCLMSAI ETGVIFLIND GIDRGLWDLQ   240
NKADAQNPVL VKYRDMSVPP ES                                            262

SEQ ID NO: 8            moltype = AA  length = 262
FEATURE                 Location/Qualifiers
source                  1..262
                        mol_type = protein
                        organism = Yokenella regensburgei
SEQUENCE: 8
CLTAPPKEAA KPTLMPRAQS YRDLTHLPLP SGKVFVSVYN IQDETGQFKP YPASNFSTAV   60
PQSATAMLVT ALKDSRWFVP LERQGLQNLL NERKIIRAAQ ENGTVADNNR IPLQSLTAAN   120
VMIEGSIIGY ESNVKSGGVG ARYFGIGADT QYQLDQIAVN LRVVNVSTGE VLSSVNTSKT   180
ILSYEVQAGV FRFVDYQRLL EGEIGYTSNE PVMLCLMSAI ETGVIYLIND GIERGLWDLQ   240
QKADVDNPIL ARYRNMSAPP ES                                            262

SEQ ID NO: 9            moltype = AA  length = 262
FEATURE                 Location/Qualifiers
source                  1..262
                        mol_type = protein
                        note = Cronobacter pulveris
                        organism = unidentified
SEQUENCE: 9
CLTAPPKEAA KPTLMPRAQS YRDLTNLPDP KGKLFVSVYN IQDETGQFKP YPASNFSTAV   60
PQSATSMLVT ALKDSRWFIP LERQGLQNLL NERKIIRAAQ ENGTVAENNR MPLQSLVAAN   120
VMIEGSIIGY ESNVKSGGVG ARYFGIGGDT QYQLDQIAVN LRVVNVSTGE VLSSVNTSKT   180
ILSYEVQAGV FRFIDYQRLL EGEIGYTANE PVMLCLMSAI ETGVIHLIND GINRGLWELK   240
NKGDAKNTIL AKYRSMAVPP ES                                            262

SEQ ID NO: 10           moltype = AA  length = 262
FEATURE                 Location/Qualifiers
source                  1..262
                        mol_type = protein
                        organism = Rahnella aquatilis
SEQUENCE: 10
CLTAAPKEAA RPTLLPRAPS YTDLTHLPSP QGRIFVSVYN IQDETGQFKP YPACNFSTAV   60
PQSATAMLVS ALKDSKWFIP LERQGLQNLL NERKIIRAAQ ENGSVAINNQ RPLSSLVAAN   120
ILIEGSIIGY ESNVKSGGVG ARYFGIGAST QYQLDQIAVN LRAVDVNTGE VLSSVNTSKT   180
ILSYEVQAGV FRFIDYQRLL EGELGYTTNE PVMLCLMSAI ESGVIYLVND GIERNLWQLQ   240
NPSEINSPIL QRYKNNIVPA ES                                            262

SEQ ID NO: 11           moltype = AA  length = 259
FEATURE                 Location/Qualifiers
```

-continued

```
source                   1..259
                         mol_type = protein
                         organism = Kluyvera ascorbata
SEQUENCE: 11
CITSPPKQAA KPTLLPRSQS YQDLTHLPEP QGRLFVSVYN ISDETGQFKP YPASNFSTSV   60
PQSATAMLVS ALKDSNWFIP LERQGLQNLL NERKIIRAAQ ENGTVAVNNR TQLPSLVAAN   120
ILIEGSIIGY ESNVKSGGAG ARYFGIGAST QYQLDQIAVN LRVVNVSTGE VLSSVNTSKT   180
ILSYEFQAGV FRYIDYQRLL EGEVGYTVNE PVMLCLMSAI ETGVIYLVND GISRNLWQLK   240
NASDINSPVL EKYKSIIVP                                               259

SEQ ID NO: 12           moltype = AA   length = 259
FEATURE                 Location/Qualifiers
source                  1..259
                        mol_type = protein
                        organism = Hafnia alvei
SEQUENCE: 12
CLTAPPKQAA KPTLMPRAQS YQDLTHLPEP AGKLFVSVYN IQDETGQFKP YPASNFSTAV   60
PQSATAMLVS ALKDSGWFIP LERQGLQNLL NERKIIRAAQ ENGTAAVNNQ HQLSSLVAAN   120
VLVEGSIIGY ESNVKSGGAG ARFFGIGAST QYQLDQIAVN LRVVDVNTGQ VLSSVNTSKT   180
ILSYEVQAGV FRYIDYQRLL EGEIGYTTNE PVMLCVMSAI ETGVIYLVND GINRNLWTLK   240
NPQDAKSSVL ERYKSTIVP                                               259

SEQ ID NO: 13           moltype = AA   length = 255
FEATURE                 Location/Qualifiers
source                  1..255
                        mol_type = protein
                        note = Enterobacteriaceae bacterium strain FGI 57
                        organism = unidentified
SEQUENCE: 13
CITTPPQEAA KPTLLPRDAT YKDLVSLPQP RGKIYVAVYN IQDETGQFQP YPASNFSTSV   60
PQSATAMLVS SLKDSRWFVP LERQGLNNLL NERKIIRAAQ QNGTVGDNNA SPLPSLYSAN   120
VIVEGSIIGY ASNVKTGGFG ARYFGIGGST QYQLDQVAVN LRIVNVHTGE VLSSVNTSKT   180
ILSYEIQAGV FRFIDYQRLL EGEAGFTTNE PVMTCLMSAI EEGVIHLIND GINKKLWALS   240
NAADINSEVL TRYRK                                                   255

SEQ ID NO: 14           moltype = AA   length = 258
FEATURE                 Location/Qualifiers
source                  1..258
                        mol_type = protein
                        organism = Plesiomonas shigelloides
SEQUENCE: 14
ITEVPKEAAK PTLMPRASTY KDLVALPKPN GKIIVSVYSV QDETGQFKPL PASNFSTAVP   60
QSGNAMLTSA LKDSGWFVPL EREGLQNLLN ERKIIRAAQE NGTVAANNQQ PLPSLLSANV   120
VIEGAIIGYD SDIKTGGAGA RYFGIGADGK YRVDQVAVNL RAVDVRTGEV LLSVNTSKTI   180
LSSELSAGVF RFIEYQRLLE LEAGYTTNEP VMMCMMSALE AGVAHLIVEG IRQNLWSLQN   240
PSDINNPIIQ RYMKEDVP                                                258

SEQ ID NO: 15           moltype = AA   length = 248
FEATURE                 Location/Qualifiers
source                  1..248
                        mol_type = protein
                        note = Vibrio fischeri
                        organism = unidentified
SEQUENCE: 15
PETSESPTLM QRGANYIDLI SLPKPQGKIF VSVYDFRDQT GQYKPQPNSN FSTAVPQGGT   60
ALLTMALLDS EWFYPLERQG LQNLLTERKI IRAAQKKQES ISNHGSTLPS LLSANVMIEG   120
GIVAYDSNIK TGGAGARYLG IGGSGQYRAD QVTVNIRAVD VRSGKILTSV TTSKTILSYE   180
VSAGAFRFVD YKELLEVELG YTNNEPVNIA LMSAIDSAVI HLIVKGVQQG LWRPANLDTR   240
NNPIFKKY                                                           248

SEQ ID NO: 16           moltype = AA   length = 248
FEATURE                 Location/Qualifiers
source                  1..248
                        mol_type = protein
                        organism = Aliivibrio logei
SEQUENCE: 16
PDASESPTLM QRGATYLDLI SLPKPQGKIY VSVYDFRDQT GQYKPQPNSN FSTAVPQGGT   60
ALLTMALLDS EWFYPLERQG LQNLLTERKI IRAAQKKQES ISNHGSTLPS LLSANVMIEG   120
GIVAYDSNIK TGGAGARYLG IGGSGQYRAD QVTVNIRAVD VRSGKILTSV TTSKTILSYE   180
LSAGAFRFVD YKELLEVELG YTNNEPVNIA LMSAIDSAVI HLIVKGIEEG LWRPENQNGK   240
ENPIFRKY                                                           248

SEQ ID NO: 17           moltype = AA   length = 254
FEATURE                 Location/Qualifiers
source                  1..254
                        mol_type = protein
                        note = Photobacterium sp. AK15
                        organism = unidentified
SEQUENCE: 17
```

```
PETSKEPTLM ARGTAYQDLV SLPLPKGKVY VSVYDFRDQT GQYKPQPNSN FSTAVPQGGA    60
ALLTTALLDS RWFMPLEREG LQNLLTERKI IRAAQKKDEI PTNHGVHLPS LASANIMVEG   120
GIVAYDTNIQ TGGAGARYLG VGASGQYRTD QVTVNIRAVD VRTGRILLSV TTSKTILSKE   180
LQTGVFKFVD YKDLLEAELG YTTNEPVNLA VMSAIDAAVV HVIVDGIKTG LWEPLRGEDL   240
QHPIIQEYMN RSKP                                                    254

SEQ ID NO: 18           moltype = AA  length = 261
FEATURE                 Location/Qualifiers
source                  1..261
                        mol_type = protein
                        organism = Aeromonas veronii
SEQUENCE: 18
CATHIGSPVA DEKATLMPRS VSYKELISLP KPKGKIVAAV YDFRDQTGQY LPAPASNFST    60
AVTQGGVAML STALWDSQWF VPLEREGLQN LLTERKIVRA AQNKPNVPGN NANQLPSLVA   120
ANILIEGGIV AYDSNVRTGG AGAKYFGIGA SGEYRVDQVT VNLRAVDIRS GRILNSVTTS   180
KTVMSQQVQA GVFRFVEYKR LLEAEAGFST NEPVQMCVMS AIESGVIRLI ANGVRDNLWQ   240
LADQRDIDNP ILQEYLQDNA P                                            261

SEQ ID NO: 19           moltype = AA  length = 239
FEATURE                 Location/Qualifiers
source                  1..239
                        mol_type = protein
                        note = Shewanella sp. ECSMB14101
                        organism = unidentified
SEQUENCE: 19
ASSSLMPKGE SYYDLINLPA PQGVMLAAVY DFRDQTGQYK PIPSSNFSTA VPQSGTAFLA    60
QALNDSSWFI PVEREGLQNL LTERKIVRAG LKGDANKLPQ LNSAQILMEG GIVAYDTNVR   120
TGGAGARYLG IGAATQFRVD TVTVNLRAVD IRTGRLLSSV TTTKSILSKE ITAGVFKFID   180
AQELLESELG YTSNEPVSLC VASAIESAVV HMIADGIWKG AWNLADQASG LRSPVLQKY    239

SEQ ID NO: 20           moltype = AA  length = 233
FEATURE                 Location/Qualifiers
source                  1..233
                        mol_type = protein
                        organism = Pseudomonas putida
SEQUENCE: 20
QDSETPTLTP RASTYYDLIN MPRPKGRLMA VVYGFRDQTG QYKPTPASSF STSVTQGAAS    60
MLMDALSASG WFVVLEREGL QNLLTERKII RASQKKPDVA ENIMGELPPL QAANLMLEGG   120
IIAYDTNVRS GGEGARYLGI DISREYRVDQ VTVNLRAVDV RTGQVLANVM TSKTIYSVGR   180
SAGVFKFIEF KKLLEAEVGY TTNEPAQLCV LSAIESAVGH LLAQGIEQRL WQV          233

SEQ ID NO: 21           moltype = AA  length = 234
FEATURE                 Location/Qualifiers
source                  1..234
                        mol_type = protein
                        organism = Shewanella violacea
SEQUENCE: 21
MPKSDTYYDL IGLPHPQGSM LAAVYDFRDQ TGQYKAIPSS NFSTAVPQSG TAFLAQALND    60
SSWFVPVERE GLQNLLTERK IVRAGLKGEA NQLPQLSSAQ ILMEGGIVAY DTNIKTGGAG   120
ARYLGIGVNS KFRVDTVTVN LRAVDIRTGR LLSSVTTTKS ILSKEVSAGV FKFIDAQDLL   180
ESELGYTSNE PVSLCVAQAI ESAVVHMIAD GIWKRAWNLA DTASGLNNPV LQKY         234

SEQ ID NO: 22           moltype = AA  length = 245
FEATURE                 Location/Qualifiers
source                  1..245
                        mol_type = protein
                        organism = Marinobacterium jannaschii
SEQUENCE: 22
LTRRMSTYQD LIDMPAPRGK IVTAVYSFRD QSGQYKPAPS SSFSTAVTQG AAAMLVNVLN    60
DSGWFIPLER EGLQNILTER KIIRAALKKD NVPVNNSAGL PSLLAANIML EGGIVGYDSN   120
IHTGGAGARY FGIGASEKYR VDEVTVNLRA IDIRTGRILH SVLTSKKILS REIRSDVYRF   180
IEFKHLLEME AGITTNDPAQ LCVLSAIESA VAHLIVDGVI KKSWSLADPN ELNSPVIQAY   240
QQQRI                                                              245

SEQ ID NO: 23           moltype = AA  length = 234
FEATURE                 Location/Qualifiers
source                  1..234
                        mol_type = protein
                        note = Chryseobacterium oranimense G311
                        organism = unidentified
SEQUENCE: 23
PSDPERSTMG ELTPSTAELR NLPLPNEKIV IGVYKFRDQT GQYKPSENGN NWSTAVPQGT    60
TTILIKALED SRWFIPIERE NIANLLNERQ IIRSTRQEYM KDADKNSQSL PPLLYAGILL   120
EGGVISYDSN TMTGGFGARY FGIGASTQYR QDRITIYLRA VSTLNGEILK TVYTSKTILS   180
TSVNGSFFRY IDTERLLEAE VGLTQNEPVQ LAVTEAIEKA VRSLIIEGTR DKIW         234

SEQ ID NO: 24           moltype = AA  length = 10
FEATURE                 Location/Qualifiers
REGION                  1..10
```

-continued

```
                        note = StrepII(C)
source                  1..10
                        mol_type = protein
                        organism = synthetic construct
SEQUENCE: 24
SAWSHPQFEK                                                            10

SEQ ID NO: 25           moltype = DNA   length = 861
FEATURE                 Location/Qualifiers
misc_feature            1..861
                        note = DNA sequence encoding
                         Pro-CP1-Eco-(WT-Y51A/F56Q/D149N/E185N/E201N/E203N-StrepII(C
                         ))
source                  1..861
                        mol_type = other DNA
                        organism = synthetic construct
SEQUENCE: 25
atgcagcgtc tgtttctgct ggtcgcggtg atgctgctga gcggttgtct gaccgcaccg    60
ccgaaagaag cggcacgtcc gaccctgatg ccgcgtgcac agagctataa agatctgacc   120
catctgccgg ctccgacggg caaaatcttc gtttctgtct acaacatcca ggacgaaacc   180
ggtcaattta aaccagctcc tgcgtcaaat caatcgactg ccgttccgca gtcagcaacc   240
gctatgctgg tcacggcact gaaagattcg cgttggttca ttccgctgga acgccagggc   300
ctgcaaaacc tgctgaatga acgtaaaatt atccgcgcag ctcaggaaaa cggtaccgtg   360
gccattaaca atcgcatccc gctgcaaagt ctgacggcgg ccaacatcat ggttgaaggc   420
tccattatcg gttatgaaag caatgtcaaa tctggcggtg tgggcgcacg ttatttcggc   480
attggtgcta atacccagta ccaactggac cagatcgcag ttaacctgcg cgtggttaat   540
gtcagcaccg gcgaaattct gagctctgtg aataccagta aaacgatcct gtcctacaac   600
gtgcaggctg gtgtttttcg tttcattgat tatcaacgcc tgctgaatgg caacgtcggt   660
tacaccagca acgaaccggt gatgctgtgt ctgatgtctg cgattgaaac gggtgttatt   720
tttctgatca atgatggcat cgaccgtggt ctgtgggatc tgcagaacaa agcggaacgt   780
caaaatgaca ttctggtgaa ataccgccac atgtcagttc cgccggaaag ttccgcatgg   840
agccacccgc agttcgaaaa a                                              861

SEQ ID NO: 26           moltype = AA   length = 287
FEATURE                 Location/Qualifiers
REGION                  1..287
                        note = Amino acid sequence of
                         Pro-CP1-Eco-(WT-Y51A/F56Q/D149N/E185N/E201N/E203N-StrepII(C
                         ))
source                  1..287
                        mol_type = protein
                        organism = synthetic construct
SEQUENCE: 26
MQRLFLLVAV MLLSGCLTAP PKEAARPTLM PRAQSYKDLT HLPAPTGKIF VSVYNIQDET     60
GQFKPAPASN QSTAVPQSAT AMLVTALKDS RWFIPLERQG LQNLLNERKI IRAAQENGTV    120
AINNRIPLQS LTAANIMVEG SIIGYESNVK SGGVGARYFG IGANTQYQLD QIAVNLRVVN    180
VSTGEILSSV NTSKTILSYN VQAGVFRFID YQRLLNGNVG YTSNEPVMLC LMSAIETGVI    240
FLINDGIDRG LWDLQNKAER QNDILVKYRH MSVPPESSAW SHPQFEK                  287
```